United States Patent
Hostetler et al.

(10) Patent No.: US 8,846,643 B2
(45) Date of Patent: Sep. 30, 2014

(54) PHOSPHONATES WITH REDUCED TOXICITY FOR TREATMENT OF VIRAL INFECTIONS

(71) Applicant: The Regents of the University of California, Oakland, CA (US)

(72) Inventors: Karl Y. Hostetler, Del Mar, CA (US); James R. Beadle, San Diego, CA (US); Nadejda Valiaeva, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/649,671

(22) Filed: Oct. 11, 2012

(65) Prior Publication Data

US 2013/0029940 A1     Jan. 31, 2013

Related U.S. Application Data

(63) Continuation of application No. PCT/US2011/032558, filed on Apr. 14, 2011.

(60) Provisional application No. 61/324,224, filed on Apr. 14, 2010.

(51) Int. Cl.
| | |
|---|---|
| *A61K 31/675* | (2006.01) |
| *C07D 239/70* | (2006.01) |
| *C07F 9/6561* | (2006.01) |
| *A61K 31/522* | (2006.01) |
| *A61K 31/52* | (2006.01) |
| *C07F 9/6512* | (2006.01) |

(52) U.S. Cl.
CPC ........... *C07F 9/65616* (2013.01); *A61K 31/675* (2013.01); *A61K 31/522* (2013.01); *A61K 31/52* (2013.01); *C07F 9/65121* (2013.01)
USPC ............................... 514/81; 514/86; 544/244

(58) Field of Classification Search
None
See application file for complete search history.

(56) References Cited

U.S. PATENT DOCUMENTS

| | | | |
|---|---|---|---|
| 6,716,825 | B2 | 4/2004 | Hostetler et al. |
| 7,034,014 | B2 | 4/2006 | Hostetler et al. |
| 7,094,772 | B2 | 8/2006 | Hostetler et al. |
| 7,098,197 | B2 | 8/2006 | Hostetler et al. |
| 7,452,898 | B2 | 11/2008 | Hostetler et al. |
| 7,687,480 | B2 | 3/2010 | Hostetler et al. |

FOREIGN PATENT DOCUMENTS

| | | | |
|---|---|---|---|
| WO | WO2005/087788 | A2 | 9/2005 |
| WO | WO2006/066074 | A2 | 6/2006 |
| WO | WO2010/135520 | A1 | 11/2010 |
| WO | WO 2010135520 | A1 * | 11/2010 |

OTHER PUBLICATIONS

CAS Registry. American Chemical Society. STN CAS Registry Database.*
Aldern, K.A., et al. "Synthesis and antiviral evaluation of alkoxyalkyl esters of acyclic purine and pyrimidine nucleoside phosphonates against HIV-1 in vitro." Antiviral Research. (2006), vol. 72, pp. 10-19.*
Figlerowicz, M., et al. "Genetic Variability: The Key Problem in the Prevention and Therapy of RNA-Based Virus Infections." Medicinal Research Reviews. (2003), vol. 23, No. 4, pp. 488-518, Available at: < http://onlinelibrary.wiley.com/doi/10.1002/med.10045/pdf >.*
Mayo Clinic. "Smallpox." Available at: < http://www.mayoclinic.com/health/smallpox/DS00424/METHOD=print&DSECTION=all >.*
Wikipedia. "Progressive multifocal leukoencephalopathy." Available at: < http://en.wikipedia.org/wiki/Progressive_multifocal_leukoencephalopathy#Treatment >.*
Dietze, K., et al. "African Swine Fever (ASF) recent developments — timely updates." Empres Emergency Prevention System. Available at: < http://www.fao.org/docrep/016/ap372e/ap372e.pdf >.*
Merta, et al. "Phosphorylation of 9-(2-phosphonomethoxyethyl)adenine and 9-(S)-(3-hydroxy-2-phosphonomethoxypropyl)adenine by AMP(dAMP) kinase from L1210 cells." Biochemical Pharmacology. (1992), vol. 44 pp. 2067-2077, IDS of Nov. 12, 2013. (10).*
Pomeisl, K et al. "Pyrimidine acyclic nucleoside phosphonates and phosphorylated analogs (part 2): syntheses and investigation of their inhibitory effects towards." Nucleic Acids Symposium Series. (2008), 52(1), pp. 657-658.*
Balzarini, J., et al. "9-[(2RS)-3-Fluoro-2-phosphonylmethoxypropyl] derivatives of purines: A class of highly selective antiretroviral agents in vitro and in vivo." Proc. Natl. Acad. Sci. (1991), vol. 88, pp. 4961-4965.*
Beadle et al., "Alkoxyalkyl Esters of Cidofovir and Cyclic Cidofovir Exhibit Multiple-Log Enhancement of Antiviral Activity against Cytomegalovirus and Herpesvirus Replication In Vitro", *Antimicrobial Agents and Chemotherapy*, 46(8):2381-2386 (2002).
Beadle et al., "Synthesis and Antiviral Evaluation of Alkoxyalkyl Derivatives of 9-(S)-(3-Hydroxy-2-phosphonomethoxypropyl)adenine against Cytomegalovirus and Orthopoxviruses", *Journal of Medicinal Chemistry*, 49(6):2010-2015 (2006).
Brown, "Progress towards improving antiviral therapy for hepatitis C with hepatitis C virus polymerase inhibitors. Part 1: Nucleoside analogues", *Expert Opinion on Investigational Drugs*, 18(6):709-725 (2009).

(Continued)

*Primary Examiner* — Andrew D Kosar
*Assistant Examiner* — John S Kenyon
(74) *Attorney, Agent, or Firm* — Kilpatrick Townsend & Stockton LLP

(57) ABSTRACT

There are provided, inter alia, acyclic nucleoside phosphonate compounds having reduced toxicity and enhanced antiviral activity, and pharmaceutically accepted salts and solvates thereof. There are also provided methods of using the disclosed compounds for inhibiting viral RNA-dependent RNA polymerase, inhibiting viral reverse transcriptase, inhibiting replication of virus, including hepatitis C virus or a human retrovirus, and treating a subject infected with a virus, including hepatitis C virus or a human retrovirus.

17 Claims, No Drawings

(56) References Cited

OTHER PUBLICATIONS

Database Caplus [Online] Chemical Abstracts Service, Columbus, Ohio, US; Otmar, Miroslav et al: "An alternative synthesis of HPMPC and HPMPA diphosphoryl derivatives", retrieved from STN Database accession No. 2000:234286; & Otmar, Miroslav et al: "An alternative synthesis of HPMPC and HPMPA diphosphoryl derivatives", Collection Symposium Series, 2(Chemistry of Nucleic Acid Components), 252-254 Coden: CSYSFN, 1999.
Database Caplus [Online] Chemical Abstracts Service, Columbus, Ohio, US; Votruba, Ivan et al: "Inhibition of human purine nucleoside phosphorylase by tenofovir phosphate congeners", retrieved from STN Database accession No. 2010:1628491 ; & Votruba, Ivan et al: "Inhibition of human purine nucleoside phosphorylase by tenofovir phosphate congeners", Collection of Czechoslovak Chemical Communications, 75(12), 1249-1257 Coden: CCCCAK; ISSN: 0010-0765, 2010.
De Clercq, "Acyclic nucleoside phosphonates: Past, present and future Bridging chemistry to HIV, HBV, HCV, HPV, adeno-, herpes-, and poxvirus infections : The phosphonate bridge", *Biochemical Pharmacology*, 73:911-922 (2007).
Extended European Search Report dated Oct. 10, 2013 for European Application No. EP11769615.3, 13 pages.
Holý, "Antiviral acyclic nucleoside phosphonates structure activity studies", *Antiviral Research, ELSEVIER*, 71:248-253 (2006).
Hostetler et al., "Aikoxyalkyl Esters of (S)-9-[3-Hydroxy-2-(Phosphonomethoxy)propyl]Adenine Are Potent Inhibitors of the Replication of Wild-Type and Drug-Resistant Human Immunodeficiency Virus Type 1 In Vitro", *Antimicrobial Agents and Chemotherapy, American Society for Microbiology*, 50(8):2857-2859 (2006).
International Preliminary Report on Patentability and Written Opinion dated Oct. 16, 2012 for International Application No. PCT/US2011/032558, 7 pages.
International Search report dated Jan. 18, 2012 for International Application No. PCT/US2011/032558, 5 pages.
Kern et al., "Enhanced Inhibition of Orthopoxvirus Replication In Vitro by Alkoxyalkyl Esters of Cidofovir and Cyclic Cidofovir", *Antimicrobial Agents and Chemotherapy*, 46(4):991-995(2002).
Koh et al., "Design, Synthesis and Antiviral Activity of Adenosine 5'-Phosphonate Analogues as Chain Terminators against Hepatitis C Virus", *Journal of Medicinal Chemistry* 48(8):2867-2875 (2005).
Magee et al., "Mechanism of Inhibition of Vaccinia Virus DNA Polymerase by Cidofovir Diphosphate", *Antimicrobial Agents and Chemotherapy, American Society for Microbiology*, 49(8):3153-3162 (2005).
Merta et al., "Phosphorylation of 9-(2-phosphonomethoxyethyl) adenine and 9-(S)-(3-hydroxy-2-phosphonomethoxypropyl)adenine by AMP (dAMP) kinase from L1210 cells", *Biochemical Pharmacology, ELSEVIER*, 44(10):2067-2077 (1992).
Pomeisl et al., "Pyrimidine Acyclic Nucleoside Phosphonates and Phosphorylated Analogs (Part 2): Syntheses and Investigation of Their Inhibitory Effects Towards Human Thymidine Phosphorylase", *Nucleic Acids Symposium Series*, 52(1): 657-658 (2008).
Prichard et al., "Inhibition of Herpesvirus Replication by Hexadecyloxypropyl Esters of Purine-and Pyrimidine-Based Phosphonomethoxyethyl Nucleoside Phosphonates", *Antimicrobial Agents and Chemotherapy*, 52:4326-4330 (2008).
Rosenberg et al., "Phosphonylmethoxyalkyl and Phosphonylalkyl Derivatives of Adenine*", *Collection Czechoslovak Chem. Commun.*, 53:2753-2777 (1988).
Sheng et al., "Discovery of novel phosphonate derivatives as hepatitis C virus NS3 protease inhibitors", *Bioorganic & Medicinal Chemistry Letters, ELSEVIER*, 19:3453-3457 (2009).
Valiaeva et al., "Synthesis and antiviral evaluation of alkoxyalkyl esters of acyclic purine and pyrimidine nucleoside phosphonates against HIV-1 in vitro", *Antiviral Research, ELSEVIER*, 72(1):10-19 (2006).
Wyles et al., "The Octadecyloxyethyl Ester of (S)-9-[3-Hydroxy-2-(Phosphonomethoxy)Propyl]Adenine Is a Potent and Selective Inhibitor of Hepatitus C Virus Replication in Genotype 1A, 1B, and 2A Replicons", *Antimicrobial Agents and Chemotherapy, American Society for Microbiology*, 53:2660-2662 (2009).
Yokota et al., "Inhibitory effects of acyclic nucleoside phosphonate analogs on hepatitis B virus DNA synthesis in HB611 cells", *Antiviral Chemistry and Chemotherapy*, 5(2):57-63 (1994).

* cited by examiner

PHOSPHONATES WITH REDUCED TOXICITY FOR TREATMENT OF VIRAL INFECTIONS

CROSS-REFERENCES TO RELATED APPLICATIONS

This application is a continuation of PCT/US2011/032558, filed Apr. 14, 2011, which claims the benefit of U.S. Provisional Application No. 61/324,224, filed Apr. 14, 2010, each of which is incorporated herein in its entirety and for all purposes.

STATEMENT AS TO RIGHTS TO INVENTIONS MADE UNDER FEDERALLY SPONSORED RESEARCH OR DEVELOPMENT

This invention was made with government support under grant numbers AI-071803, AI-076558 and AI-074057 awarded by the National Institutes of Health. The Government has certain rights in the invention.

BACKGROUND OF THE INVENTION

The hepatitis C virus (HCV) is the leading cause of chronic liver disease worldwide, infecting an estimated 170 million persons. Antiviral research directed toward the development of improved treatment methods for chronic HCV infections has focused mainly on inhibitors of the NS5B polymerase. See e.g., Brown, N. A., 2009, *Expert Opin. Investig. Drugs* 18:709-725. Indeed, treatment of hepatitis C virus (HCV) infection remains an important unmet medical need due to the inadequacies of current interferon-based therapy. See e.g., Falck-Ytter, Y., et al., 2003, *Ann. Intern. Med.,* 136:288-292. In the United States there are 3 to 4 million persons with chronic HCV infection. See e.g., Armstrong, G. L., et al., 2006, *Ann. Intern. Med.,* 144:705-714. A number of agents are currently in clinical development for HCV including NS3 protease inhibitors and NS5B antiviral nucleosides and non-nucleoside polymerase inhibitors. See e.g., Sarrazin, C. & Zeuzem, S., 2010, *Gastroenterology,* 138:447-462. Clinical and in vitro data indicate that resistance develops readily with protease and non-nucleoside polymerase inhibitors. See e.g., Sarrazin, C, et al., 2007, *Gastroenterology,* 132:1767-1777; McCown, M. F., et al., 2009, *Antimicrob. Agents Chemother.,* 53:2129-2132; Howe, A. Y. M, et al., 2008, *Antimicrob. Agents Chemother.,* 52:3327-3338. Nucleoside inhibitors which target the catalytic site of the NS5B RNA dependent RNA polymerase have been shown to be active across different HCV genotypes. See e.g., McCown M. F., et al., 2008, *Antimicrob. Agents Chemother.,* 52:1604-1612.

A current therapy for chronic hepatitis C includes combination treatment with weekly injections of pegylated alpha-IFN (pegIFN) and daily oral ribavirin (RBV) administration. PegIFN/RBV treatment is effective in >75% of patients infected with HCV genotype-2 (HCV-2) and genotype-3 (HCV-3), but most patients in North America, Europe and Japan are infected with HCV genotype-1 (HCV-1) and only about 40-50% of HCV-1 patients respond to therapy with pegIFN/RBV.

There are currently only a few anti-HCV nucleosides in clinical studies. See Table A.

TABLE A

Selected HCV polymerase and protease inhibitors in development taken from (Brown, N. A., *Expert Opin. Investig. Drugs* 18: 709-725 (2009)).

| Compound Nucleoside HCV NS5B Polymerase Inhibitors (NIs) | Sponsor | Development phase | Comment |
|---|---|---|---|
| NM283 (valopicitabine) | Idenix-Novartis | IIb | Development discontinued 2007 |
| R1626 | Roche | IIa | Prodrug of R1479; development discontinued 2008 |
| R7128 | Pharmasset-Roche | IIa | Prodrug of PSI-6130 |
| IDX184 | Idenix | Ib | Phase Ia data in healthy volunteers |
| MK-0608 | Merck | Late preclinical | |
| PSI-7851 | Pharmasset | Ia | Preclinical data |
| ≥3 others | Various sponsors | Preclinical | No data available |

Some acyclic nucleoside phosphonates (ANPs) are antiviral agents with activity against double stranded DNA (dsDNA) viruses, or viruses which rely on reverse transcription such as HBV and HIV-1. See e.g., Hostetler K. Y., 2009, *Antiviral Res.,* 82:A84-98; Morrey, J. D. 2009, *Antimicrob. Agents Chemother.,* 53:2865-2870; Hostetler, K. Y., et al., 2006, *Antimicrob. Agents Chemother.,* 50:2857-2859. We previously reported that octadecyloxyethyl 9-(S)-[3-hydroxy-2-(phosphonomethoxy)propyl]adenine (ODE-(S)-HPMPA, 1) exhibited antiviral activity against genotype 1b and 2a HCV replicons. See e.g., Wyles, D. L., et al., 2009, *Antimicrob. Agents Chemother.,* 53:2660-2662. Some acyclic nucleoside phosphonates of this class (i.e., HPMP series) are broad spectrum anti-DNA virus agents. See e.g., De Clercq, E., 2007, *Biochem. Pharmacol.* 73:911-922. Some compounds of this class have been reported to be inactive against RNA viruses, including HCV. See e.g., Holý, A., 2006, *Antiviral Res.* 71:248-253. ODE-(S)-HPMPA has shown cytotoxicity. See e.g., Wyles et al., 2009, Id.; Beadle, J. R., et al., 2006, *J. Med. Chem.,* 49:2010-2015.

Koh et al. prepared 2'-C-methyl phosphonate analogs of adenosine (Koh, Y., et al., 2005, *J. Med. Chem.* 48:2867). Others have reported phosphonates with weak anti-HCV activity. See e.g., Mackman, "Synthesis and antiviral activity of 4'-modified carbocyclic nucleoside phosphonates (CNPs)," *Collection Symposium Series* 10:191 (2008); Sheng, X. C. et al., 2009, *Bioorg. Med. Chem. Lett.* 19:3453-3457.

There is a need for improved anti-HCV therapeutic agents, i.e. drugs having improved antiviral and pharmacokinetic properties with enhanced activity against development of HCV resistance, improved oral bioavailability, greater efficacy and fewer undesirable side effects. The present invention provides solutions for these and other needs in the art. For example, we have found, inter alia, that derivatives of ODE-(S)-HPMPA modified by alkylation of the acyclic side chain hydroxyl are surprisingly potent inhibitors of HCV replication in vitro and importantly are much less toxic than ODE-(S)-HPMPA both in vitro and in vivo in mice.

BRIEF SUMMARY OF THE INVENTION

There are provided, inter alia, phosphonate ester compounds having biological activity, e.g., antiviral activity. There are also provided, inter alia, compounds having inhibitory activity for viruses, e.g., inhibition of hepatitis C virus replication. In some embodiments, the compounds are substantially less toxic than previously known antiviral phosphonates, e.g., anti-HCV phosphonates, while retaining excellent antiviral inhibitory activity, e.g., inhibition of HCV. There are also provided, inter alia, improved anti-HCV therapeutic agents.

In a first aspect, there is provided a compound having the structure of Formula (I), or pharmaceutically accepted salt or solvate thereof:

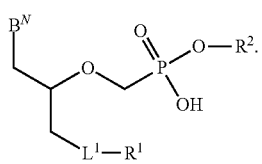

With reference to Formula (I), $B^N$ is a substituted or unsubstituted nucleobase. $L^1$ is a bond or —O—. $R^1$ is halogen, —$CF_3$, substituted or unsubstituted alkyl, substituted or unsubstituted cycloalkyl, or substituted or unsubstituted aryl. In some embodiments, if $L^1$ is a bond, then $R^1$ is halogen. In certain embodiments, if $L^1$ is —O—, then $R^1$ is —$CF_3$, substituted or unsubstituted alkyl, substituted or unsubstituted cycloalkyl, or substituted or unsubstituted aryl. $R^2$ is a permeability enhancing moiety, a phosphate, or a diphosphate.

In another aspect, there is provided a pharmaceutical composition which includes a compound of Formula (I) and a pharmaceutically acceptable excipient.

In another aspect, there is provided a method of inhibiting a viral RNA-dependent RNA polymerase. The method includes contacting a cell which includes a viral RNA-dependent RNA polymerase with an effective amount of a compound of Formula (I) thereby inhibiting the viral RNA-dependent RNA polymerase.

In another aspect, there is provided a method of inhibiting a viral RNA-dependent RNA polymerase. The method includes contacting a viral RNA-dependent RNA polymerase with an effective amount of a compound of Formula (I) thereby inhibiting the viral RNA-dependent RNA polymerase.

In another aspect, there is provided a method of inhibiting a viral reverse transcriptase. The method includes contacting a cell comprising a viral reverse transcriptase with an effective amount of a compound of Formula (I) thereby inhibiting the viral RNA-dependent RNA polymerase.

In another aspect, there is provided a method of inhibiting a viral reverse transcriptase. The method includes contacting a viral reverse transcriptase with an effective amount of a compound of Formula (I) thereby inhibiting the viral RNA-dependent RNA polymerase.

In another aspect, there is provided a method of inhibiting replication of an RNA virus (e.g. a hepatitis C virus or a human retrovirus). The method includes contacting a compound of Formula (I) with a cell infected with an RNA virus thereby inhibiting replication of the RNA virus.

In another aspect, there is provided a method of treating a subject infected with an RNA virus (e.g. a hepatitis C virus or a human retrovirus). The method includes administering to a subject in need thereof an effective amount of a compound of Formula (I) thereby treating the subject.

BRIEF DESCRIPTION OF THE DRAWINGS

Not applicable.

DETAILED DESCRIPTION OF THE INVENTION

I. Definitions

The abbreviations used herein have their conventional meaning within the chemical and biological arts.

Where moieties are specified by their conventional chemical formulae, written from left to right, they equally encompass the chemically identical moieties that would result from writing the structure from right to left, e.g., —$CH_2O$— is equivalent to —$OCH_2$—.

The term "alkyl," by itself or as part of another substituent, means, unless otherwise stated, a straight (i.e. unbranched) or branched chain, or cyclic hydrocarbon radical, or combination thereof, which may be fully saturated, mono- or polyunsaturated and can include di- and ultivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butyryl, and the higher homologs and isomers.

The term "alkylene" by itself or as part of another substituent means a divalent radical derived from an alkyl, as exemplified, but not limited, by —$CH_2CH_2CH_2CH_2$—. Typically, an alkyl (or alkylene) group will have from 1 to 24 carbon atoms, including those groups having 10 or fewer carbon atoms. A "lower alkyl" or "lower alkylene" is a shorter chain alkyl or alkylene group, generally having eight or fewer carbon atoms.

The terms "alkoxy," "alkylamino," and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and a heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituent moieties for each of the above noted aryl and heteroaryl ring systems may be selected from the group of acceptable substituent moieties described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo" as used herein means an oxygen that is double bonded to a carbon atom.

Each of the above terms (e.g., "alkyl," "heteroalkyl," "aryl" and "heteroaryl") are meant to include both substituted and unsubstituted forms of the indicated radical. Preferred substituent moieties for each type of radical are provided below.

Substituent moieties for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O) NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituent moieties, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituent moieties described for the alkyl radical, substituent moieties for the aryl and heteroaryl groups are varied and may be selected from, for example: halogen, —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R—)=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$) alkoxy, and fluoro($C_1$-$C_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituent moieties on adjacent atoms of the aryl or heteroaryl ring may optionally form a ring of the formula -Q'-C(O)—(CRR')$_q$-Q"-, wherein Q' and Q" are independently —NR—, —O—, —CRR'— or a single bond, and q is an integer of from 0 to 3. Alternatively, two of the substituent moieties on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)₂—, —S(O)₂NR'— or a single bond, and r is an integer of from 1 to 4. One of the single bonds of the new ring so formed may optionally be replaced with a double bond. Alternatively, two of the substituent moieties on adjacent atoms of the aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)₂—, or —S(O)₂NR'—. The substituent moieties R, R', R" and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

The term "pharmaceutically acceptable salts" is meant to include salts of the active compounds which are prepared with relatively nontoxic acids or bases, depending on the particular substituent moieties found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, tautomers, geometric isomers and individual isomers are encompassed within the scope of the present invention. The compounds of the present invention do not include those which are known in the art to be too unstable to synthesize and/or isolate.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

In some embodiments, each substituted aryl and/or heterocycloalkyl is substituted with a substituent group, a size limited substituent group, or a lower substituent group. A "substituent group," as used herein, means a group selected from the following moieties:

(A) —OH, —NH₂, —SH, —CN, —CF₃, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:
  (i) oxy, —OH, —NH₂, —SH, —CN, —CF₃, halogen, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, and heteroaryl, substituted with at least one substituent selected from:
    (a) oxy, —OH, —NH₂, —SH, —CN, —CF₃, halogen, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, or heteroaryl, substituted with at least one substituent selected from oxy, —OH, —NH₂, —SH, —CN, —CF₃, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The term "treating" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being, and the like. The treatment or amelioration of symptoms can be based on objective or subjective parameters; including the results of a physical examination, laboratory tests, and the like. For example, the methods described herein may be used to treat the symptoms of a viral infection.

As used herein, "nucleic acid" means single stranded DNA, RNA and derivative thereof Modifications include, but are not limited to, those which provide other chemical groups that incorporate additional charge, polarizability, hydrogen bonding, electrostatic interaction, and functionality to the nucleic acid ligand bases or to the nucleic acid ligand as a whole. Such modifications include, but are not limited to, phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping moieties. A 2'-deoxy nucleic acid linker is a divalent nucleic acid compound of any appropriate length and/or internucleotide linkage wherein the nucleotides are 2'-deoxy nucleotides.

Solid and dashed wedge bonds indicate stereochemistry as customary in the art. A "squiggle" bond (i.e., "∿∿∿") indicates either R- or S-stereochemistry.

II. Compositions

In a first aspect, there is provided a compound having the structure of Formula (I), or pharmaceutically accepted salt or solvate thereof:

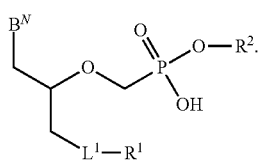

(I)

With reference to Formula (I), $B^N$ is a substituted or unsubstituted nucleobase. $L^1$ is a bond or —O—. $R^1$ is halogen, —$CF_3$, substituted or unsubstituted alkyl, substituted or unsubstituted cycloalkyl, or substituted or unsubstituted aryl. In some embodiments, if $L^1$ is a bond, then $R^1$ is halogen. In some embodiments, if $L^1$ is —O—, then $R^1$ is —$CF_3$, substituted or unsubstituted alkyl, substituted or unsubstituted cycloalkyl, or substituted or unsubstituted aryl. $R^2$ is a permeability enhancing moiety, a phosphate, or a diphosphate.

As used herein, the term "nucleobase" refers to a moiety as generally known in the nucleic acid arts which can function as the base portion of a nucleic acid. A nucleobase is a portion of a nucleic acid involved in hybridization (base pairing), and includes, but is not limited to nitrogenous bases such as adenine, guanine, thymine, uracil, cytosine, 2,6-diaminopurine, and the like. The term "hybridization" is used herein in its conventional sense and refers generally to the pairing of complementary strands of nucleic acids, including triple-stranded nucleic acid hybridization.

In some embodiments, $B^N$ is substituted or unsubstituted thymine, substituted or unsubstituted guanine, substituted or unsubstituted cytosine, substituted or unsubstituted uracil, substituted or unsubstituted 2,6 diaminopurine, substituted or unsubstituted, substituted or unsubstituted methoxypurine, or substituted or unsubstituted 6-O-methylguanine A person of ordinary skill in the art will immediately understand that, when referring to a nucleobase ($B^N$), such as guanine, that the nucleobase is attached to the remainder of the molecule of Formula I (or embodiments thereof) and, therefore, exists as a monovalent moiety. In some embodiments, $B^N$ is unsubstituted adenine, unsubstituted thymine, unsubstituted guanine, unsubstituted cytosine, or unsubstituted uracil.

In some embodiments, $B^N$ is substituted adenine, substituted thymine, substituted guanine, substituted cytosine, or substituted uracil. In some embodiments, $B^N$ is 2,6-diaminopurine. In some embodiments, $B^N$ is 6-methoxypurine. In some embodiments, $B^N$ is 6-O-methylguanine.

In some embodiments, the compound of Formula (I) has the structure of Formula (Ia) following (wherein $L^1$ is —O— according to Formula (I)). In some embodiments of Formula (Ia), $R^1$ is —$CF_3$, substituted or unsubstituted alkyl, substituted or unsubstituted cycloalkyl, or substituted or unsubstituted aryl.

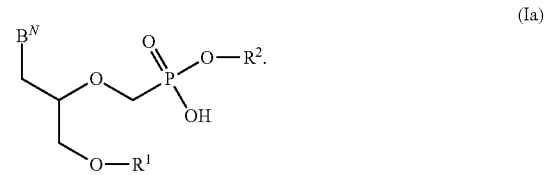

(Ia)

In some embodiments of Formulae (I) or (Ia), $R^1$ is unsubstituted alkyl. In some embodiments, $R^1$ is $R^4$-substituted alkyl. $R^4$ is —CN, —$NH_2$, —COOH, —$CF_3$, —OH, —SH, —$CONH_2$, halogen, $R^5$-substituted or unsubstituted alkyl, $R^5$-substituted or unsubstituted heteroalkyl, $R^5$-substituted or unsubstituted cycloalkyl, $R^5$-substituted or unsubstituted heterocycloalkyl, $R^5$-substituted or unsubstituted aryl, or $R^5$-substituted or unsubstituted heteroaryl. In some embodiments $R^4$ is unsubstituted alkyl, unsubstituted heteroalkyl, unsubstituted cycloalkyl, unsubstituted heterocycloalkyl, unsubstituted aryl, or unsubstituted heteroaryl. In some embodiments $R^4$ is $R^5$-substituted alkyl, $R^5$-substituted heteroalkyl, $R^5$-substituted cycloalkyl, $R^5$-substituted heterocycloalkyl, $R^5$-substituted aryl, or $R^5$-substituted heteroaryl. $R^5$ is —CN, —$NH_2$, —COOH, —$CF_3$, —OH, —SH, —$CONH_2$, halogen, $R^6$-substituted or unsubstituted alkyl, $R^6$-substituted or unsubstituted heteroalkyl, $R^6$-substituted or unsubstituted cycloalkyl, $R^6$-substituted or unsubstituted heterocycloalkyl, $R^6$-substituted or unsubstituted aryl, or $R^6$-substituted or unsubstituted heteroaryl. In some embodiments, $R^5$ is unsubstituted alkyl, unsubstituted heteroalkyl, unsubstituted cycloalkyl, unsubstituted heterocycloalkyl, unsubstituted aryl, or unsubstituted heteroaryl. In some embodiments, $R^5$ is $R^6$-substituted alkyl, $R^6$-substituted heteroalkyl, $R^6$-substituted cycloalkyl, $R^6$-substituted heterocycloalkyl, $R^6$-substituted aryl, or $R^6$-substituted heteroaryl. $R^6$ is —CN, —NH$_2$, —COOH, —CF$_3$, —OH, —SH, —CONH$_2$, halogen, unsubstituted alkyl, unsubstituted heteroalkyl, unsubstituted cycloalkyl, unsubstituted heterocycloalkyl, unsubstituted aryl, or unsubstituted heteroaryl.

In some embodiments, $R^1$ is unsubstituted cycloalkyl. In some embodiments, $R^1$ is $R^7$-substituted cycloalkyl. $R^7$ is —CN, —NH$_2$, —COOH, —CF$_3$, —OH, —SH, —CONH$_2$, halogen, $R^8$-substituted or unsubstituted alkyl, $R^8$-substituted or unsubstituted heteroalkyl, $R^8$-substituted or unsubstituted cycloalkyl, $R^8$-substituted or unsubstituted heterocycloalkyl, $R^8$-substituted or unsubstituted aryl, or $R^8$-substituted or unsubstituted heteroaryl. In some embodiments $R^7$ is unsubstituted alkyl, unsubstituted heteroalkyl, unsubstituted cycloalkyl, unsubstituted heterocycloalkyl, unsubstituted aryl, or unsubstituted heteroaryl. In some embodiments $R^7$ is $R^8$-substituted alkyl, $R^8$-substituted heteroalkyl, $R^8$-substituted cycloalkyl, $R^8$-substituted heterocycloalkyl, $R^8$-substituted aryl, or $R^8$-substituted heteroaryl. $R^8$ is —CN, —NH$_2$, —COOH, —CF$_3$, —OH, —SH, —CONH$_2$, halogen, $R^9$-substituted or unsubstituted alkyl, $R^9$-substituted or unsubstituted heteroalkyl, $R^9$-substituted or unsubstituted cycloalkyl, $R^9$-substituted or unsubstituted heterocycloalkyl, $R^9$-substituted or unsubstituted aryl, or $R^9$-substituted or unsubstituted heteroaryl. In some embodiments, $R^8$ is unsubstituted alkyl, unsubstituted heteroalkyl, unsubstituted cycloalkyl, unsubstituted heterocycloalkyl, unsubstituted aryl, or unsubstituted heteroaryl. In some embodiments, $R^8$ is $R^9$-substituted alkyl, $R^9$-substituted heteroalkyl, $R^9$-substituted cycloalkyl, $R^9$-substituted heterocycloalkyl, $R^9$-substituted aryl, or $R^9$-substituted heteroaryl. $R^9$ is —CN, —NH$_2$, —COOH, —CF$_3$, —OH, —SH, —CONH$_2$, halogen, unsubstituted alkyl, unsubstituted heteroalkyl, unsubstituted cycloalkyl, unsubstituted heterocycloalkyl, unsubstituted aryl, or unsubstituted heteroaryl.

In some embodiments, $R^1$ is unsubstituted aryl. In some embodiments, $R^1$ is $R^{10}$-substituted aryl. $R^{10}$ is —CN, —NH$_2$, —COOH, —CF$_3$, —OH, —SH, —CONH$_2$, halogen, $R^{11}$-substituted or unsubstituted alkyl, $R^{11}$-substituted or unsubstituted heteroalkyl, $R^{11}$-substituted or unsubstituted cycloalkyl, $R^{11}$-substituted or unsubstituted heterocycloalkyl, $R^{11}$-substituted or unsubstituted aryl, or $R^{11}$-substituted or unsubstituted heteroaryl. In some embodiments $R^{10}$ is unsubstituted alkyl, unsubstituted heteroalkyl, unsubstituted cycloalkyl, unsubstituted heterocycloalkyl, unsubstituted aryl, or unsubstituted heteroaryl. In some embodiments $R^{10}$ is $R^{11}$-substituted alkyl, $R^{11}$-substituted heteroalkyl, $R^{11}$-substituted cycloalkyl, $R^{11}$-substituted heterocycloalkyl, $R^{11}$-substituted aryl, or $R^{11}$-substituted heteroaryl. $R^{11}$ is —CN, —NH$_2$, —COOH, —CF$_3$, —OH, —SH, —CONH$_2$, halogen, $R^{12}$-substituted or unsubstituted alkyl, $R^{12}$-substituted or unsubstituted heteroalkyl, $R^{12}$-substituted or unsubstituted cycloalkyl, $R^{12}$-substituted or unsubstituted heterocycloalkyl, $R^{12}$-substituted or unsubstituted aryl, or $R^{12}$-substituted or unsubstituted heteroaryl. In some embodiments, $R^{11}$ is unsubstituted alkyl, unsubstituted heteroalkyl, unsubstituted cycloalkyl, unsubstituted heterocycloalkyl, unsubstituted aryl, or unsubstituted heteroaryl. In some embodiments, $R^{11}$ is $R^{12}$-substituted substituted alkyl, $R^{12}$-substituted heteroalkyl, $R^{12}$-substituted cycloalkyl, $R^{12}$-substituted heterocycloalkyl, $R^{12}$-substituted aryl, or $R^{12}$-substituted heteroaryl. $R^{12}$ is —CN, —NH$_2$, —COOH, —CF$_3$, —OH, —SH, —CONH$_2$, halogen, unsubstituted alkyl, unsubstituted heteroalkyl, unsubstituted cycloalkyl, unsubstituted heterocycloalkyl, unsubstituted aryl, or unsubstituted heteroaryl.

Further to the compound of Formulae (I) or (Ia), in some embodiments, $R^1$ is substituted (e.g., $R^4$-substituted) or unsubstituted $C_1$-$C_{24}$ (e.g., $C_1$-$C_{10}$ or $C_1$-$C_3$) alkyl. In some embodiments, $R^1$ is $C_1$-$C_{24}$ unsubstituted alkyl. In some embodiments, $R^1$ is $C_1$-$C_{16}$ unsubstituted alkyl. In some embodiments, $R^1$ is $C_1$-$C_{12}$ unsubstituted alkyl. In some embodiments, $R^1$ is $C_1$-$C_{10}$ unsubstituted alkyl. In some embodiments, $R^1$ is $C_1$-$C_3$ unsubstituted alkyl. In some embodiments, $R^1$ is methyl, ethyl or isopropyl. In some embodiments, $R^1$ is methyl. In some embodiments, $R^1$ is ethyl. In some embodiments, $R^1$ is isopropyl.

Further to the compound of Formulae (I) or (Ia), in some embodiments, $R^1$ is substituted (e.g., $R^7$-substituted) or unsubstituted $C_3$-$C_8$ cycloalkyl. In some embodiments, $R^1$ is $C_3$-$C_8$ unsubstituted cycloalkyl.

Further to the compound of Formulae (I) or (Ia), in some embodiments, $R^1$ is unsubstituted aryl. In some embodiments, $R^1$ is substituted (e.g., $R^{10}$-substituted) or unsubstituted phenyl.

Further to the compound of Formulae (I) or (Ia), in some embodiments, $R^1$ is substituted alkyl. In some embodiments, $R^1$ is substituted $C_1$-$C_{10}$ alkyl. In some embodiments, $R^1$ is haloalkyl. In some embodiments, $R^1$ is monohaloalkyl. In some embodiments, $R^1$ is dihaloalkyl. In some embodiments, $R^1$ is trihaloalkyl. In some embodiments, $R^1$ is —CF$_3$.

In some embodiments of the compound of Formulae (I) or (Ia) wherein $R^1$ is substituted alkyl, substituted $C_1$-$C_{10}$ alkyl, substituted cycloalkyl, or substituted aryl, $R^1$ is alkyl substituted with substituted or unsubstituted aryl. In some embodiments, $R^1$ is benzyl.

In some embodiments of the compound of Formulae (I) or (Ia) wherein $R^1$ is substituted alkyl, substituted cycloalkyl, or substituted aryl, $R^1$ is substituted cycloalkyl. In some embodiments, $R^1$ is substituted $C_3$-$C_8$ cycloalkyl.

In some embodiments of the compound of Formulae (I) or (Ia) wherein $R^1$ is substituted alkyl, substituted cycloalkyl, or substituted aryl, $R^1$ is substituted aryl. In some embodiments, $R^1$ is substituted phenyl.

In some embodiments, the compound of Formula (I) has the structure of Formula (Ib) (i.e., where $L^1$ is a bond). In some embodiments, $R^1$ is halogen:

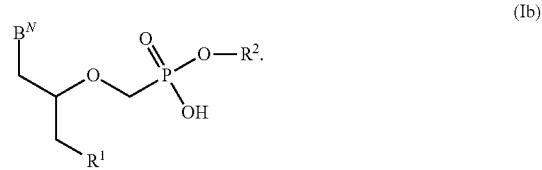

(Ib)

In some embodiments of the compound of Formulae (I) or (Ib), $R^1$ is fluoro. In Formula (Ib), $B^N$ and $R^2$ are as defined above in Formulae (I) and (IA).

Further to the compound with the structure of any of Formulae (I), (Ia) or (Ib), in some embodiments, $R^2$ has the structure of Formula (II) following,

(II)

wherein $L^2$ is a substituted or unsubstituted alkylene, substituted or unsubstituted cycloalkylene, or substituted or unsubstituted arylene. $R^3$ is substituted or unsubstituted alkyl, substituted or unsubstituted cycloalkyl, or substituted or unsubstituted aryl.

In some embodiments, $R^3$ is unsubstituted alkyl. In some embodiments, $R^3$ is substituted (e.g., $R^{13}$-substituted) or unsubstituted $C_1$-$C_{24}$ (e.g., $C_{16}$-$C_{24}$ or $C_8$-$C_{16}$) alkyl. In some embodiments, $R^3$ is unsubstituted $C_1$-$C_{24}$ alkyl. In some embodiments, $R^3$ is unsubstituted $C_8$-$C_{24}$ alkyl. In some embodiments, $R^3$ is unsubstituted $C_{16}$-$C_{24}$ alkyl. In some embodiments, $R^3$ is unsubstituted $C_8$-$C_{16}$ alkyl. In some embodiments, $R^3$ is unsubstituted $C_8$-$C_{18}$ alkyl. In some embodiments, $R^3$ is substituted (e.g., $R^{13}$-substituted) or unsubstituted $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl.

In some embodiments, $R^3$ is $R^{13}$-substituted alkyl. $R^{13}$ is —CN, —NH$_2$, —COOH, —CF$_3$, —OH, —SH, —CONH$_2$, halogen, $R^{14}$-substituted or unsubstituted alkyl, $R^{14}$-substituted or unsubstituted heteroalkyl, $R^{14}$-substituted or unsubstituted cycloalkyl, $R^{14}$-substituted or unsubstituted heterocycloalkyl, $R^{14}$-substituted or unsubstituted aryl, or $R^{14}$-substituted or unsubstituted heteroaryl. In some embodiments, $R^{13}$ is unsubstituted alkyl, unsubstituted heteroalkyl, unsubstituted cycloalkyl, unsubstituted heterocycloalkyl, unsubstituted aryl, or unsubstituted heteroaryl. In some embodiments, $R^{13}$ is —CN, —NH$_2$, —COOH, —CF$_3$, —OH, —SH, —CONH$_2$, halogen, $R^{14}$-substituted alkyl, $R^{14}$-substituted heteroalkyl, $R^{14}$-substituted cycloalkyl, $R^{14}$-substituted heterocycloalkyl, $R^{14}$-substituted aryl, or $R^{14}$-substituted heteroaryl. $R^{14}$ is $R^{15}$-substituted or unsubstituted alkyl, $R^{15}$-substituted or unsubstituted heteroalkyl, $R^{15}$-substituted or unsubstituted cycloalkyl, $R^{15}$-substituted or unsubstituted heterocycloalkyl, $R^{15}$-substituted or unsubstituted aryl, or $R^{15}$-substituted or unsubstituted heteroaryl. In some embodiments, $R^{14}$ is —CN, —NH$_2$, —COOH, —CF$_3$, —OH, —SH, —CONH$_2$, halogen, unsubstituted alkyl, unsubstituted heteroalkyl, unsubstituted cycloalkyl, unsubstituted heterocycloalkyl, unsubstituted aryl, or unsubstituted heteroaryl. In some embodiments, $R^{14}$ is $R^{15}$-substituted alkyl, $R^{15}$-substituted heteroalkyl, $R^{15}$-substituted cycloalkyl, $R^{15}$-substituted heterocycloalkyl, $R^{15}$-substituted aryl, or $R^{15}$-substituted heteroaryl. $R^{15}$ is —CN, —NH$_2$, —COOH, —CF$_3$, —OH, —SH, —CONH$_2$, halogen, unsubstituted alkyl, unsubstituted heteroalkyl, unsubstituted cycloalkyl, unsubstituted heterocycloalkyl, unsubstituted aryl, or unsubstituted heteroaryl.

In some embodiments, $R^3$ is $R^{16}$-substituted cycloalkyl. $R^{16}$ is —CN, —NH$_2$, —COOH, —CF$_3$, —OH, —SH, —CONH$_2$, halogen, $R^{17}$-substituted or unsubstituted alkyl, $R^{17}$-substituted or unsubstituted heteroalkyl, $R^{17}$-substituted or unsubstituted cycloalkyl, $R^{17}$-substituted or unsubstituted heterocycloalkyl, $R^{17}$-substituted or unsubstituted aryl, or $R^{17}$-substituted or unsubstituted heteroaryl. In some embodiments, $R^{16}$ is unsubstituted alkyl, unsubstituted heteroalkyl, unsubstituted cycloalkyl, unsubstituted heterocycloalkyl, unsubstituted aryl, or unsubstituted heteroaryl. In some embodiments, $R^{16}$ is $R^{17}$-substituted alkyl, $R^{17}$-substituted heteroalkyl, $R^{17}$-substituted cycloalkyl, $R^{17}$-substituted heterocycloalkyl, $R^{17}$-substituted aryl, or $R^{17}$-substituted heteroaryl. $R^{17}$ is —CN, —NH$_2$, —COOH, —CF$_3$, —OH, —SH, —CONH$_2$, halogen, $R^{18}$-substituted or unsubstituted alkyl, $R^{18}$-substituted or unsubstituted heteroalkyl, $R^{18}$-substituted or unsubstituted cycloalkyl, $R^{18}$-substituted or unsubstituted heterocycloalkyl, $R^{18}$-substituted or unsubstituted aryl, or $R^{18}$-substituted or unsubstituted heteroaryl. In some embodiments, $R^{17}$ is unsubstituted alkyl, unsubstituted heteroalkyl, unsubstituted cycloalkyl, unsubstituted heterocycloalkyl, unsubstituted aryl, or unsubstituted heteroaryl. In some embodiments, $R^{17}$ is $R^{18}$-substituted alkyl, $R^{18}$-substituted heteroalkyl, $R^{18}$-substituted cycloalkyl, $R^{18}$-substituted heterocycloalkyl, $R^{18}$-substituted aryl, or $R^{18}$-substituted heteroaryl. $R^{18}$ is —CN, —NH$_2$, —COOH, —CF$_3$, —OH, —SH, —CONH$_2$, halogen, unsubstituted alkyl, unsubstituted heteroalkyl, unsubstituted cycloalkyl, unsubstituted heterocycloalkyl, unsubstituted aryl, or unsubstituted heteroaryl.

In some embodiments, $R^3$ is $R^{19}$-substituted aryl. $R^{19}$ is —CN, —NH$_2$, —COOH, —CF$_3$, —OH, —SH, —CONH$_2$, halogen, $R^N$-substituted or unsubstituted alkyl, $R^N$-substituted or unsubstituted heteroalkyl, $R^N$-substituted or unsubstituted cycloalkyl, $R^N$-substituted or unsubstituted heterocycloalkyl, $R^N$-substituted or unsubstituted aryl, or $R^N$-substituted or unsubstituted heteroaryl. In some embodiments, $R^{19}$ is unsubstituted alkyl, unsubstituted heteroalkyl, unsubstituted cycloalkyl, unsubstituted heterocycloalkyl, unsubstituted aryl, or unsubstituted heteroaryl. In some embodiments, $R^{19}$ is $R^N$-substituted alkyl, $R^N$-substituted heteroalkyl, $R^{20}$-substituted cycloalkyl, $R^N$-substituted heterocycloalkyl, $R^N$-substituted aryl, or $R^N$-substituted heteroaryl. $R^{20}$ is —CN, —NH$_2$, —COOH, —CF$_3$, —OH, —SH, —CONH$_2$, halogen, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl. In some embodiments, $R^{20}$ is unsubstituted alkyl, unsubstituted heteroalkyl, unsubstituted cycloalkyl, unsubstituted heterocycloalkyl, unsubstituted aryl, or unsubstituted heteroaryl. In some embodiments, $R^{20}$ is $R^{21}$-substituted alkyl, $R^{21}$-substituted heteroalkyl, $R^{21}$-substituted cycloalkyl, $R^{21}$-substituted heterocycloalkyl, $R^{21}$-substituted aryl, or $R^{21}$-substituted heteroaryl. $R^{21}$ is —CN, —NH$_2$, —COOH, —CF$_3$, —OH, —SH, —CONH$_2$, halogen, unsubstituted alkyl, unsubstituted heteroalkyl, unsubstituted cycloalkyl, unsubstituted heterocycloalkyl, unsubstituted aryl, or unsubstituted heteroaryl.

In some embodiments, $L^2$ is substituted (e.g., $R^{22}$-substituted) or unsubstituted $C_1$-$C_8$ alkylene. In some embodiments, $L^2$ is substituted (e.g., $R^{22}$-substituted) unsubstituted $C_1$, $C_2$, $C_3$, $C_4$, $C_5$, $C_6$, $C_7$, or $C_8$ alkylene.

In some embodiments, $L^2$ is $R^{22}$-substituted alkylene. $R^{22}$ is —CN, —NH$_2$, —COOH, —CF$_3$, —OH, —SH, —CONH$_2$, halogen, $R^{23}$-substituted or unsubstituted alkyl, $R^{23}$-substituted or unsubstituted heteroalkyl, $R^{23}$-substituted or unsubstituted cycloalkyl, $R^{23}$-substituted or unsubstituted heterocycloalkyl, 23-substituted or unsubstituted aryl, or 23-substituted or unsubstituted heteroaryl. In some embodiments, $R^{22}$ is unsubstituted alkyl, unsubstituted heteroalkyl, unsubstituted cycloalkyl, unsubstituted heterocycloalkyl, unsubstituted aryl, or unsubstituted heteroaryl. In some embodiments, $R^{22}$ is $R^{23}$-substituted alkyl, $R^{23}$-substituted heteroalkyl, $R^{23}$-substituted cycloalkyl, $R^{23}$-substituted heterocycloalkyl, $R^{23}$-substituted aryl, or $R^{23}$-substituted heteroaryl. $R^{23}$ is —CN, —NH$_2$, —COOH, —CF$_3$, —OH, —SH, —CONH$_2$, halogen, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl. In some embodiments, $R^{23}$ is unsubstituted alkyl, unsubstituted heteroalkyl, unsubstituted cycloalkyl, unsubstituted heterocycloalkyl, unsubstituted aryl, or unsubstituted heteroaryl. In some embodiments, $R^{23}$ is $R^{24}$-substituted alkyl, $R^{24}$-substituted heteroalkyl, $R^{24}$-substituted cycloalkyl, $R^{24}$-substituted heterocycloalkyl, $R^{24}$-substituted aryl, or $R^{24}$-substituted heteroaryl. $R^{24}$ is —CN, —NH$_2$, —COOH, —CF$_3$, —OH, —SH, —CONH$_2$, halogen, unsubstituted alkyl, unsubstituted heteroalkyl, unsubstituted cycloalkyl, unsubstituted heterocycloalkyl, unsubstituted aryl, or unsubstituted heteroaryl.

In some embodiments, $L^2$ is $R^{25}$-substituted cycloalkylene. $R^{25}$ is —CN, —NH$_2$, —COOH, —CF$_3$, —OH, —SH, —CONH$_2$, halogen, $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl. In some embodiments, $R^{25}$ is unsubstituted alkyl, unsubstituted heteroalkyl, unsubstituted cycloalkyl, unsubstituted heterocycloalkyl, unsubstituted aryl, or unsubstituted heteroaryl. In some embodiments, $R^{25}$ is $R^{26}$-substituted alkyl, $R^{26}$-substituted heteroalkyl, $R^{26}$-substituted cycloalkyl, $R^{26}$-substituted heterocycloalkyl, $R^{26}$-substituted aryl, or $R^{26}$-substituted heteroaryl. $R^{26}$ is —CN, —NH$_2$, —COOH, —CF$_3$, —OH, —SH, —CONH$_2$, halogen, $R^{27}$-substituted or unsubstituted alkyl, $R^{27}$-substituted or unsubstituted heteroalkyl, $R^{27}$-substituted or unsubstituted cycloalkyl, $R^{27}$-substituted or unsubstituted heterocycloalkyl, $R^{27}$-substituted or unsubstituted aryl, or $R^{27}$-substituted or unsubstituted heteroaryl. In some embodiments, $R^{26}$ is unsubstituted alkyl, unsubstituted heteroalkyl, unsubstituted cycloalkyl, unsubstituted heterocycloalkyl, unsubstituted aryl, or unsubstituted heteroaryl. In some embodiments, $R^{26}$ is $R^{27}$-substituted alkyl, $R^{27}$-substituted heteroalkyl, $R^{27}$-substituted cycloalkyl, $R^{27}$-substituted heterocycloalkyl, $R^{27}$-substituted aryl, or $R^{27}$-substituted heteroaryl. $R^{27}$ is —CN, —NH$_2$, —COOH, —CF$_3$, —OH, —SH, —CONH$_2$, halogen, unsubstituted alkyl, unsubstituted heteroalkyl, unsubstituted cycloalkyl, unsubstituted heterocycloalkyl, unsubstituted aryl, or unsubstituted heteroaryl.

In some embodiments, $L^2$ is $R^{28}$-substituted arylene. $R^{28}$ is —CN, —NH$_2$, —COOH, —CF$_3$, —OH, —SH, —CONH$_2$, halogen, $R^{29}$-substituted or unsubstituted alkyl, $R^{29}$-substituted or unsubstituted heteroalkyl, $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl. In some embodiments, $R^{28}$ is unsubstituted alkyl, unsubstituted heteroalkyl, unsubstituted cycloalkyl, unsubstituted heterocycloalkyl, unsubstituted aryl, or unsubstituted heteroaryl. In some embodiments, $R^{28}$ is $R^{29}$-substituted alkyl, $R^{29}$-substituted heteroalkyl, $R^{29}$-substituted cycloalkyl, $R^{29}$-substituted heterocycloalkyl, $R^{29}$-substituted aryl, or $R^{29}$-substituted heteroaryl. $R^{29}$ is —CN, —NH$_2$, —COOH, —CF$_3$, —OH, —SH, —CONH$_2$, halogen, $R^{30}$-substituted or unsubstituted alkyl, $R^N$-substituted or unsubstituted heteroalkyl, $R^N$-substituted or unsubstituted cycloalkyl, $R^N$-substituted or unsubstituted heterocycloalkyl, $R^N$-substituted or unsubstituted aryl, or $R^N$-substituted or unsubstituted heteroaryl. In some embodiments, $R^{29}$ is unsubstituted alkyl, unsubstituted heteroalkyl, unsubstituted cycloalkyl, unsubstituted heterocycloalkyl, unsubstituted aryl, or unsubstituted heteroaryl. In some embodiments, $R^{29}$ is $R^N$-substituted alkyl, $R^N$-substituted heteroalkyl, $R^N$-substituted cycloalkyl, $R^N$-substituted heterocycloalkyl, $R^N$-substituted aryl, or $R^N$-substituted heteroaryl. $R^{30}$ is —CN, —NH$_2$, —COOH, —CF$_3$, —OH, —SH, —CONH$_2$, halogen, unsubstituted alkyl, unsubstituted heteroalkyl, unsubstituted cycloalkyl, unsubstituted heterocycloalkyl, unsubstituted aryl, or unsubstituted heteroaryl.

Further to the compound with the structure of any of Formulae (I), (Ia) or (Ib), or the compound wherein $R^2$ has the structure of Formula (II), in some embodiments, $R^2$ is octadecyloxyethyl, hexadecyloxyethyl, hexadecyloxypropyl, 15-methyl-hexadecyloxypropyl, 15-methyl-hexadecyloxyethyl, 13-methyl-tetradecyloxypropyl, 13-methyl-tetradecyloxyethyl, 14-cyclopropyl-tetradecyloxypropyl, 14-cyclopropyl-tetradecyloxyethyl, or 1-O-octadecyl-2-O-benzyl-sn-glyceryl. In some embodiments, $L^2$ is $C_1$, $C_2$, $C_3$, $C_4$, $C_5$, $C_6$, $C_7$, or $C_8$ alkylene.

It is understood that some compounds described herein can exist as stereoisomeric forms including e.g., R-, S- and racemic (RS-) forms. Unless expressly indicated otherwise, all stereoisomer forms are contemplated herein. Accordingly, further to the compound with the structure of any of Formulae (I), (Ia) or (Ib), wherein $R^2$ has the structure of Formula (II), in some embodiments, the compound has the structure of one of Formulae (Ia1S) to (Ia7S) following. $R^1$ and $R^2$ in Formulae (Ia1S) to (Ia7S) are as defined above.

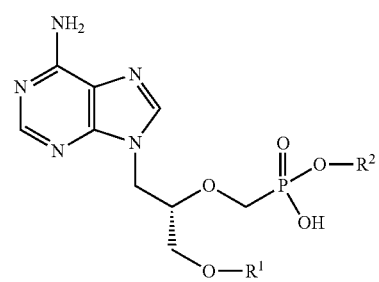
(Ia1S)

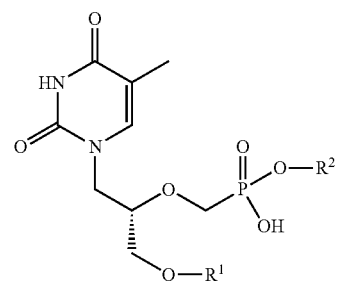
(Ia2S)

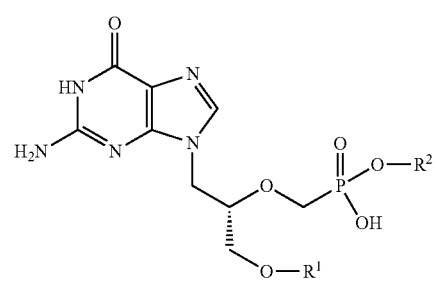
(Ia3S)

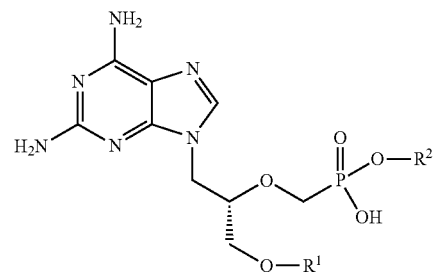
(Ia4S)

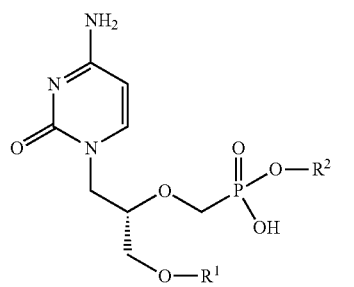
(Ia5S)
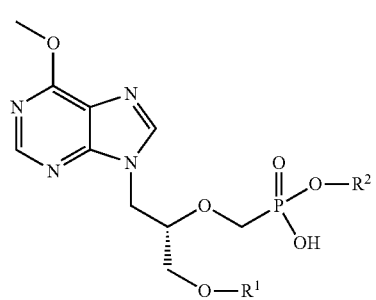
(Ia6S)
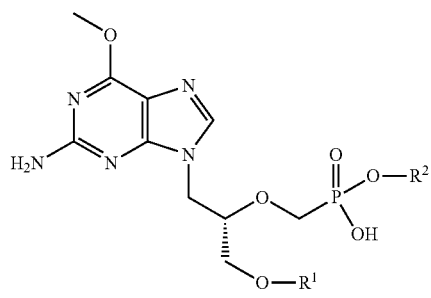
(Ia7S)
In some embodiments, the compound has the structure of one of Formulae (Ia1R) to (Ia7R) following. $R^1$ and $R^2$ in Formulae (Ia1R) to (Ia7R) are as defined above.
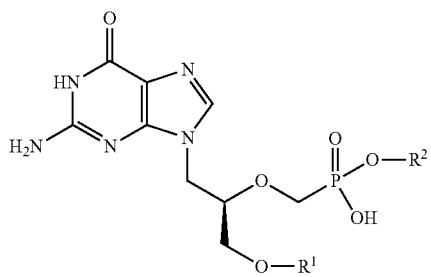
(Ia1R)
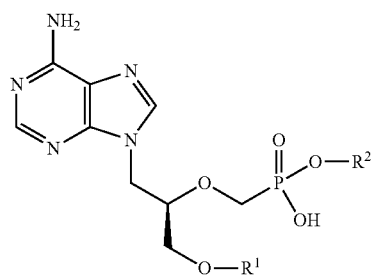
(Ia2R)
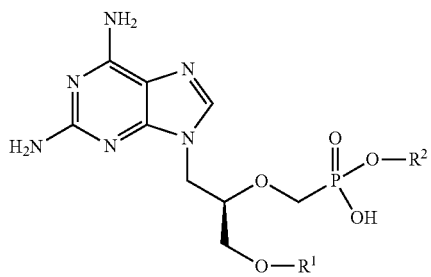
(Ia3R)
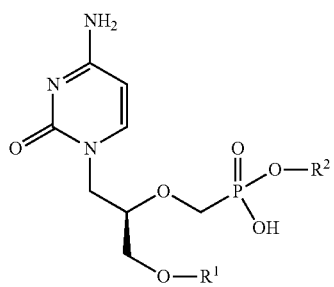
(Ia4R)
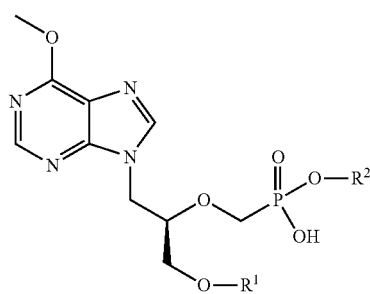
(Ia5R)
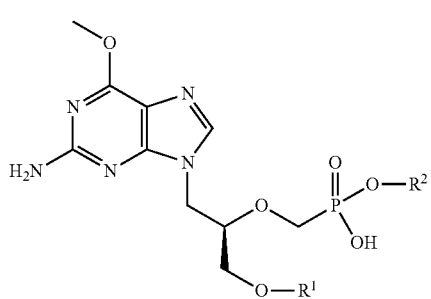
(Ia6R)
(Ia7R)
In some embodiments, the compound has the structure of one of Formulae (Ia1RS) to (Ia7RS) following. $R^1$ and $R^2$ in Formulae (Ia1RS) to (Ia7RS) are as defined above.

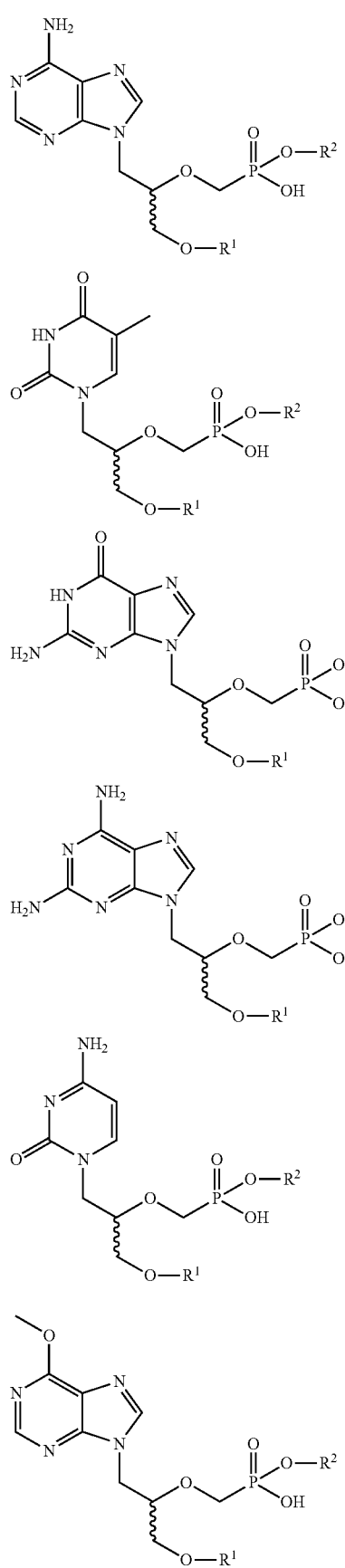
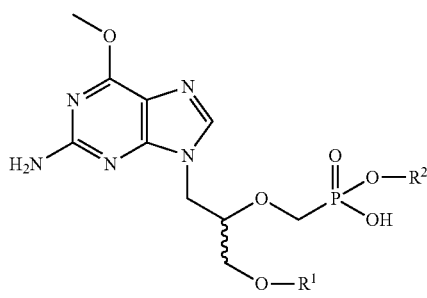
Further to the compound with the structure of Formulae (Ib), in some embodiments, the compound has the structure of one of Formulae (Ib1S) to (Ib7S) following. $R^1$ and $R^2$ in Formulae (Ib1S) to (Ib7S) are as defined above.
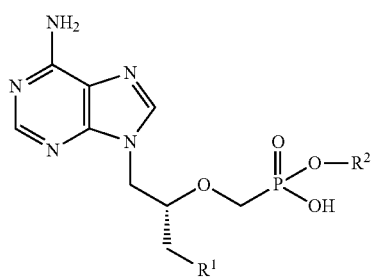
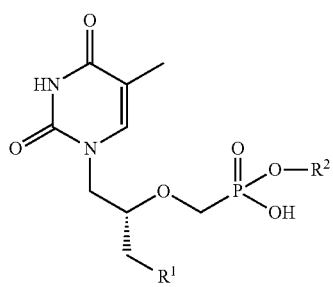
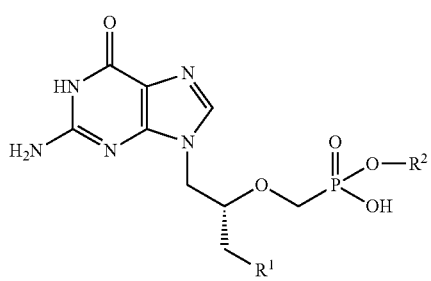
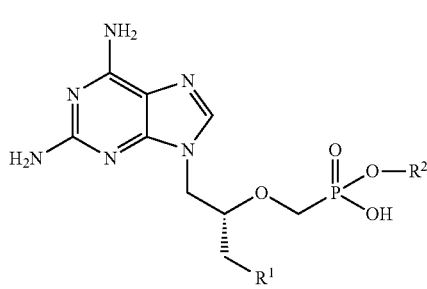

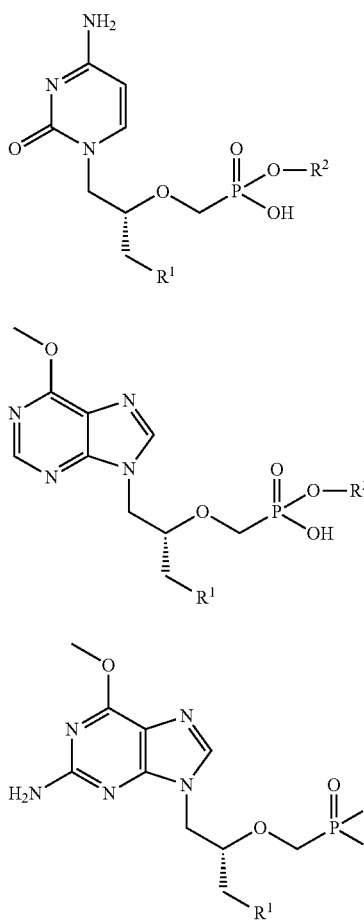
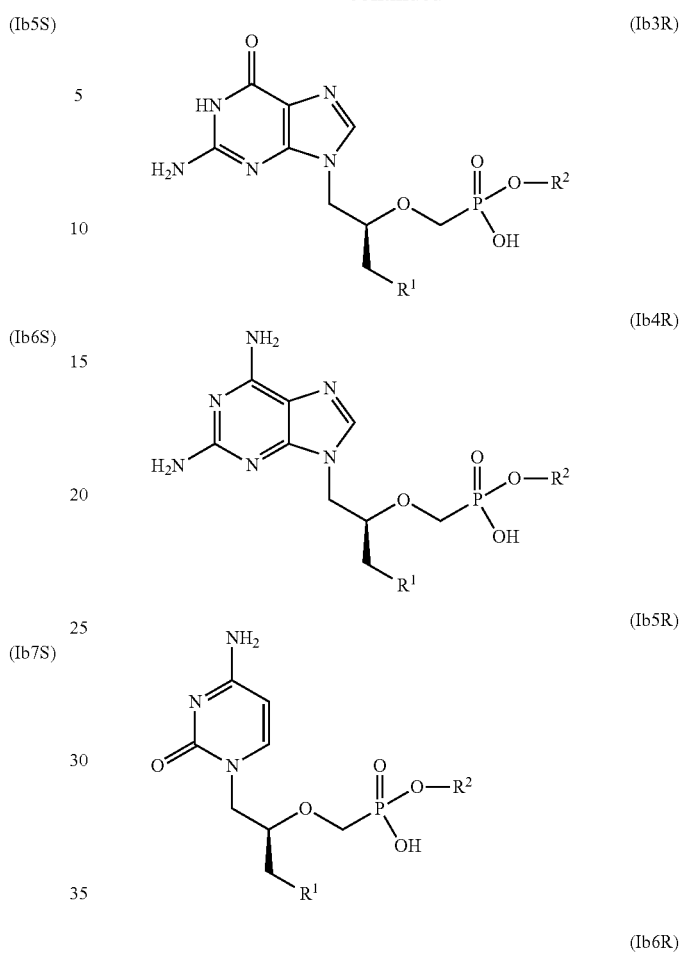
In some embodiments, the compound has the structure of one of Formulae (Ib1R) to (Ib7R) following. $R^1$ and $R^2$ in Formulae (Ib1R) to (Ib7R) are as defined above.
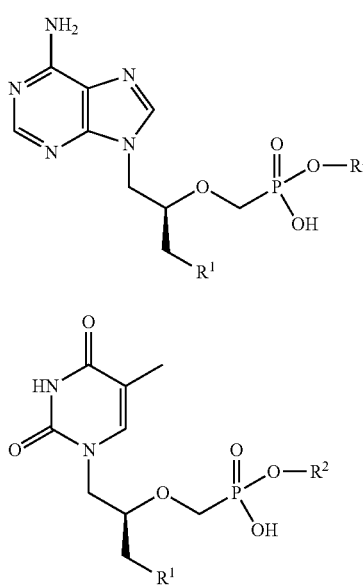
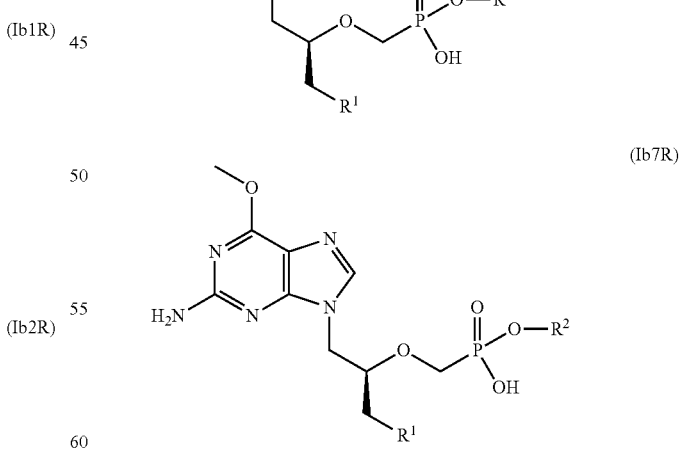
In some embodiments, the compound has the structure of one of Formulae (Ib1RS) to (Ib7RS) following. $R^1$ and $R^2$ in Formulae (Ib1RS) to (Ib7RS) are as defined above.

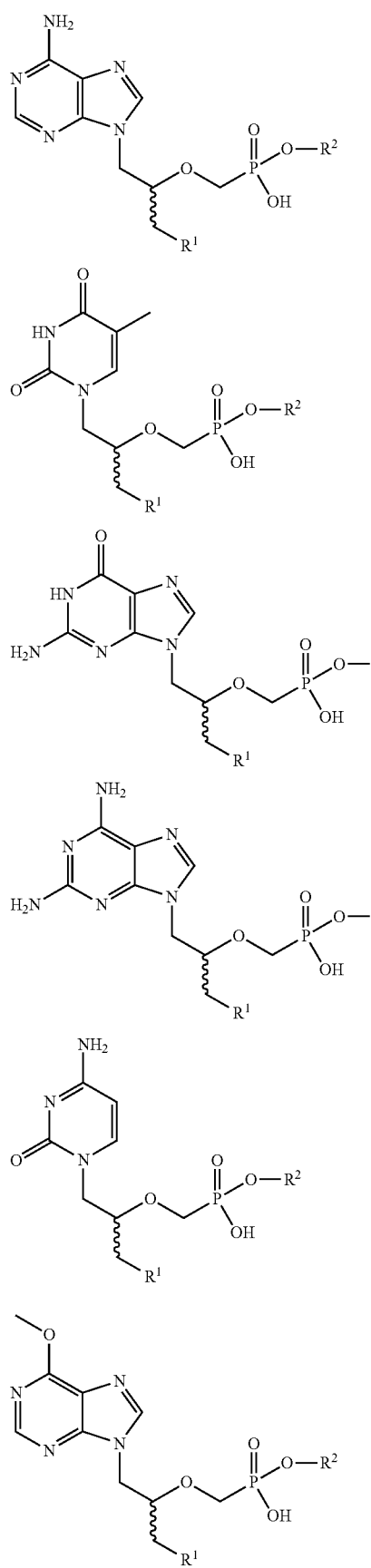
(Ib1RS)
(Ib2RS)
(Ib3RS)
(Ib4RS)
(Ib5RS)
(Ib6RS)

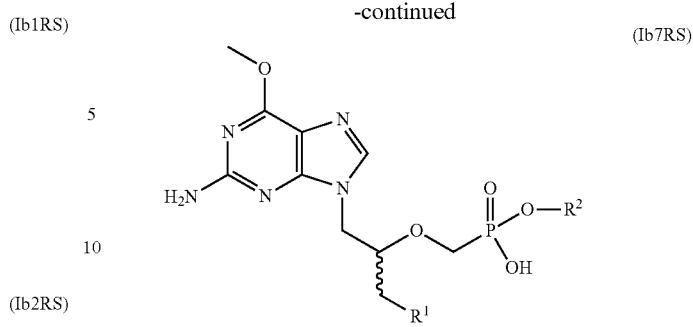
(Ib7RS)

In some embodiments of the compounds of Formulae I, Ia1S-Ia7S, Ia1R-Ia7R, or Ia1RS-Ia7RS, $R_1$ is —$CF_3$, substituted or unsubstituted $C_1$-$C_{10}$ alkyl, substituted or unsubstituted $C_3$-$C_8$ cycloalkyl (e.g. cyclopropyl) or substituted or unsubstituted aryl (e.g. benzyl or phenyl). In some embodiments, $R_1$ is —$CF_3$, unsubstituted $C_1$-$C_{10}$ alkyl, unsubstituted $C_3$-$C_8$ cycloalkyl (e.g. cyclopropyl) or unsubstituted aryl (e.g. benzyl or phenyl).

In some embodiments of the compounds of Formula I, $R^2$ is a permeability enhancing moiety, a phosphate or a diphosphate. In some embodiments, $R^2$ is a permeability enhancing moiety. A "permeability enhancing moiety" as used herein refers to a chemical moiety that forms an ester with the oxygen and phosphorus to which it is attached as shown in Formulae I, Ia1S-Ia7S, Ia1R-Ia7R, Ia1RS-Ia7RS, Ib1S-Ib7S, Ib1R-Ib7R, Ib1RS-Ib7RS, and which increases the cell permeability of the compound relative to compounds in which $R^2$ is hydrogen. In some embodiments, permeability enhancers act to increase drug absorption through either the paracellular or transcellular pathways. See e.g., Ouyang, H., et al., 2002, *J. Med. Chem.*, 45:2857-2866; Lane, M. E. & Corrigan, O. I., 2006, *J. Pharm. Pharmacol.*, 58:271-275.

In some embodiments, $R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^2$ contains 3-24, 6-24, 9-24, 12-24, 15-24, 18-24, or 21-24 carbon atoms. In some embodiments, $R^2$ is substituted or unsubstituted $C_3$ or greater alkyl, or substituted or unsubstituted $C_3$ or greater heteroalkyl. In some embodiments, $R^2$ is unsubstituted alkyl, unsubstituted heteroalkyl, unsubstituted cycloalkyl, unsubstituted heterocycloalkyl, unsubstituted aryl, or unsubstituted heteroaryl. In some embodiments, $R^2$ is unsubstituted $C_3$ or greater alkyl, or unsubstituted $C_3$ or greater heteroalkyl. In some embodiments, $R^2$ is $R^{31}$-substituted alkyl, $R^{31}$-substituted heteroalkyl, $R^{31}$-substituted cycloalkyl, $R^{31}$-substituted heterocycloalkyl, $R^{31}$-substituted aryl, or $R^{31}$-substituted heteroaryl. $R^{31}$ is —CN, —$NH_2$, —COOH, —$CF_3$, —OH, —SH, —$CONH_2$, halogen, $R^{32}$-substituted or unsubstituted alkyl, $R^{32}$-substituted or unsubstituted heteroalkyl, $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl. In some embodiments $R^{31}$ is unsubstituted alkyl, unsubstituted heteroalkyl, unsubstituted cycloalkyl, unsubstituted heterocycloalkyl, unsubstituted aryl, or unsubstituted heteroaryl. In some embodiments, $R^{31}$ is $R^{32}$-substituted alkyl, $R^{32}$-substituted heteroalkyl, R32-substituted cycloalkyl, $R^{32}$-substituted heterocycloalkyl, $R^{32}$-substituted aryl, or $R^{32}$-substituted heteroaryl. $R^{32}$ is —CN, —$NH_2$, —COOH, —$CF_3$, —OH, —SH, —$CONH_2$, halogen, $R^{33}$-substituted or unsubstituted alkyl, $R^{33}$-substituted or unsubstituted heteroalkyl, $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl. In some embodiments, $R^{32}$ is unsubstituted alkyl, unsubstituted heteroalkyl, unsubstituted cycloalkyl, unsubstituted heterocycloalkyl, unsubstituted aryl, or unsubstituted heteroaryl. In some embodiments, $R^{32}$ is $R^{33}$-substituted alkyl, $R^{33}$-substituted heteroalkyl, $R^{33}$-substituted cycloalkyl, $R^{33}$-substituted heterocycloalkyl, $R^{33}$-substituted aryl, or $R^{33}$-substituted heteroaryl. $R^{33}$ is —CN, —NH$_2$, —COOH, —CF$_3$, —OH, —SH, —CONH$_2$, halogen, unsubstituted alkyl, unsubstituted heteroalkyl, unsubstituted cycloalkyl, unsubstituted heterocycloalkyl, unsubstituted aryl, or unsubstituted heteroaryl.

Without wishing to be bound by any theory, it is believed that the lipophilicity of a permeability enhancer can play a major role in permeability enhancement. In some embodiments, the permeability enhancing moiety has the structure of Formula (II), $$-L^2-O-R^3. \tag{II}$$

In some embodiments, $L^2$ is a substituted or unsubstituted alkylene (e.g., substituted or unsubstituted $C_1$-$C_8$ alkylene), substituted or unsubstituted cycloalkylene (substituted or unsubstituted $C_3$-$C_8$ cycloalkylene), or substituted or unsubstituted arylene. In some embodiments, $R^3$ is substituted or unsubstituted alkyl (e.g. substituted or unsubstituted $C_8$-$C_{24}$ alkyl), substituted or unsubstituted cycloalkyl (e.g. a substituted or unsubstituted $C_3$-$C_8$ cycloalkyl), or substituted or unsubstituted aryl. In some embodiments, -$L^2$-O—$R^3$ includes at least 16 atoms. In some embodiments, -$L^2$-O—$R^3$ has 18 to 24 atoms. In certain embodiments, the atoms are linked together in a linear arrangement. The permeability enhancing moiety may be octadecyloxyethyl, hexadecyloxyethyl, hexadecyloxypropyl, 15-methyl-hexadecyloxypropyl, 15-methyl-hexadecyloxyethyl, 13-methyl-tetradecyloxypropyl, 13-methyl-tetradecyloxyethyl, 14-cyclopropyl-tetradecyloxypropyl, 14-cyclopropyl-tetradecyloxyethyl, or 1-O-octadecyl-2-O-benzyl-sn-glyceryl. Additional exemplary permeability enhancing moieties useful in the compounds and methods described herein are described in U.S. Pat. No. 6,716,825 and U.S. Pat. No. 7,749,983, and US Patent Publication No. US2008-0221061, the contents of which are incorporated herein by reference in their entireties and for all purposes.

In some embodiments, the novel phosphonate compounds provided herein are less toxic, more active and selective than previously known candidates such as ODE-(S)-HPMPA (which includes a hydrogen at the corresponding $R^1$ position) against a variety of viruses, including e.g., hepatitis C virus and HIV-1. The retention of antiviral efficacy against HIV and HCV with marked diminution of cellular toxicity caused by the addition of a methyl group to the side chain of HPMPA is quite unexpected and not obvious. Unmodified MPMPA had an EC$_{50}$ of 20 µM and a CC$_{50}$ of 40 µM suggesting no selective antiviral activity. "EC$_{50}$" refers, in the customary sense, to the concentration required to achieve half-maximal effect of a compound. "CC$_{50}$" refers, in the customary sense, to the concentration required to achieve half maximal cytotoxicity.

In some embodiments, each substituted group described above in the compounds of Formula I or embodiments thereof is substituted with at least one substituent group. More specifically, in some embodiments, each substituted alkyl, substituted cycloalkyl, substituted aryl, substituted alkylene substituted cycloalkylene, and/or substituted arylene, described above in the compounds of Formula I or embodiments thereof are substituted with at least one substituent group. In other embodiments, at least one or all of these groups are substituted with at least one size-limited substituent group. In some embodiments, no substituent of Formula I is further substituted.

In some embodiments, a compound is selected from Table 1 following.

TABLE 1

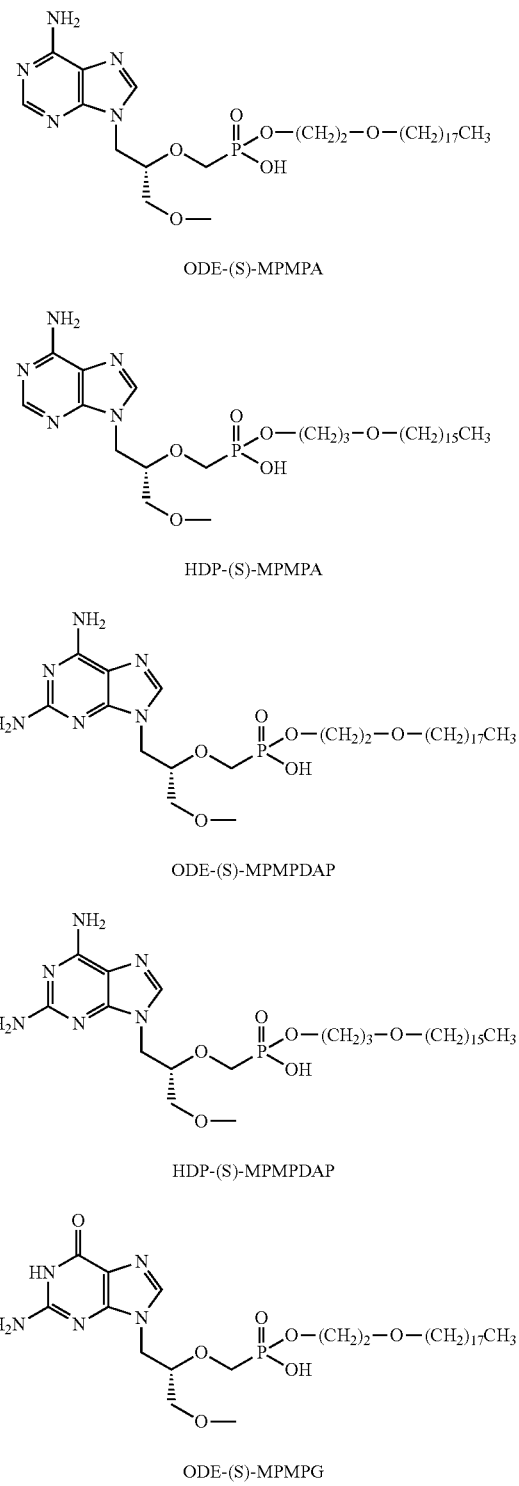

ODE-(S)-MPMPA

HDP-(S)-MPMPA

ODE-(S)-MPMPDAP

HDP-(S)-MPMPDAP

ODE-(S)-MPMPG

TABLE 1-continued
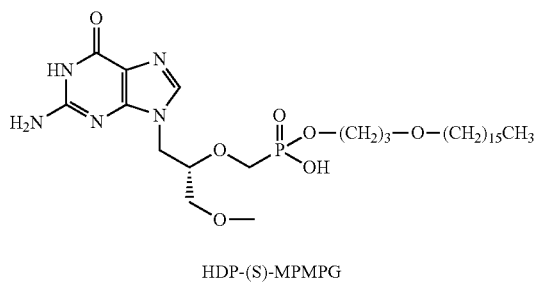
HDP-(S)-MPMPG
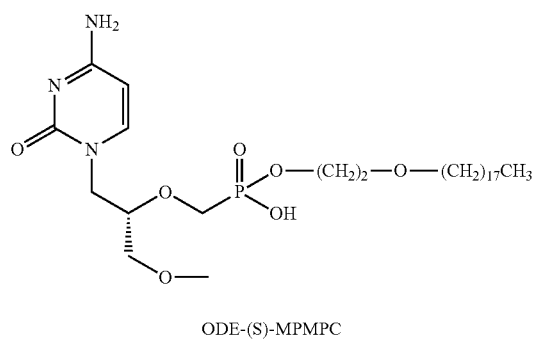
ODE-(S)-MPMPC
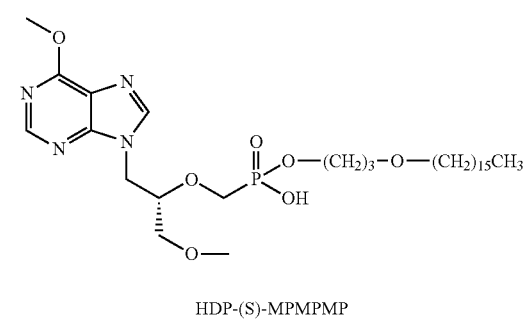
HDP-(S)-MPMPMP
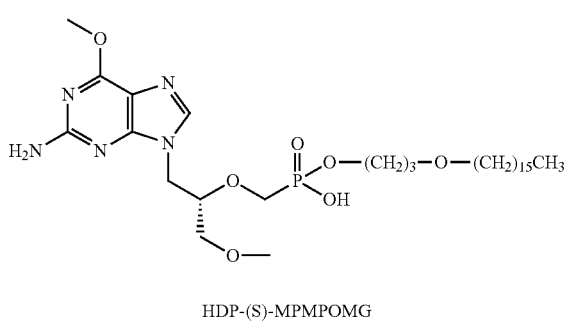
HDP-(S)-MPMPOMG
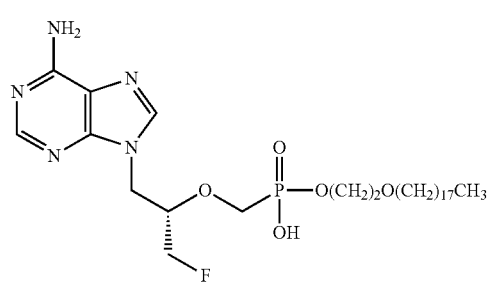
ODE-(S)-FPMPA
TABLE 1-continued
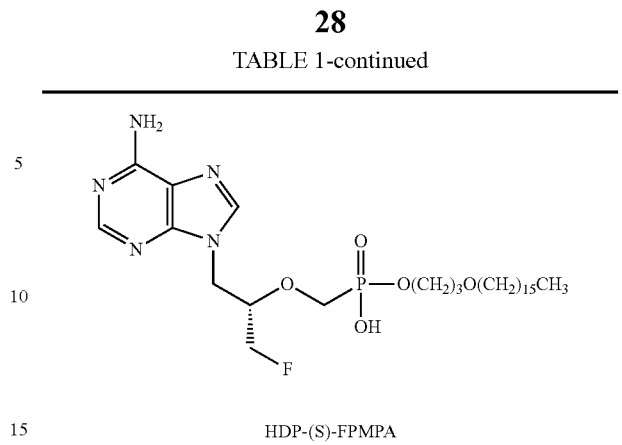
HDP-(S)-FPMPA
In some embodiments, a compound is selected from Table 2 following.
TABLE 2
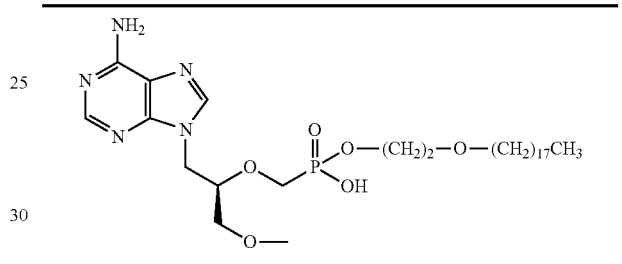
ODE-(R)-MPMPA
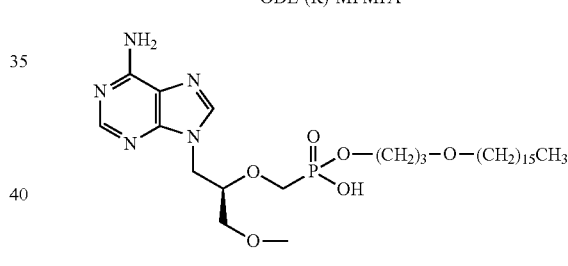
HDP-(R)-MPMPA
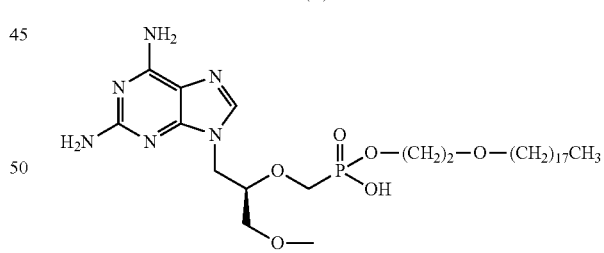
ODE-(R)-MPMPDAP
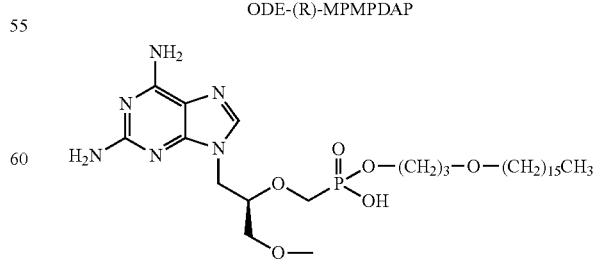
HDP-(R)-MPMPDAP TABLE 2-continued
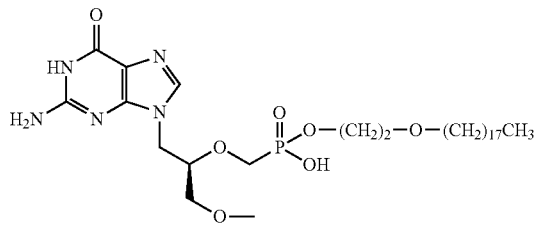
ODE-(R)-MPMPG
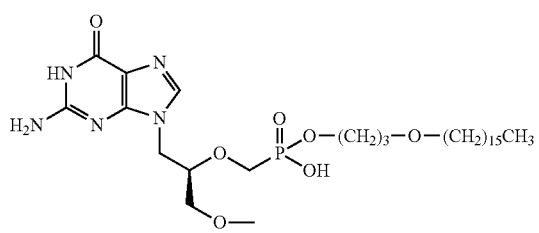
HDP-(R)-MPMPG
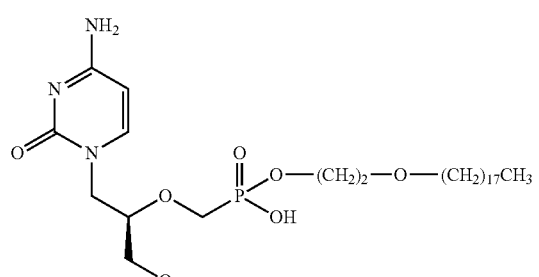
ODE-(R)-MPMPC
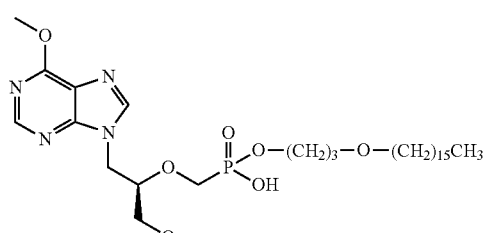
HDP-(R)-MPMPMP
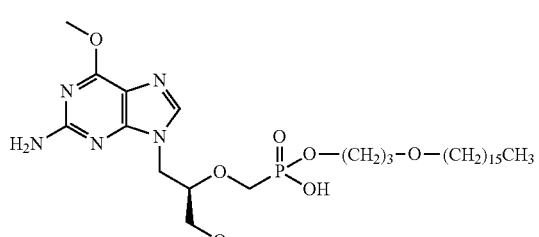
HDP-(R)-MPMPOMG
TABLE 2-continued
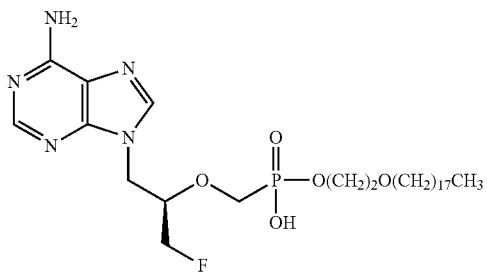
ODE-(R)-FPMPA
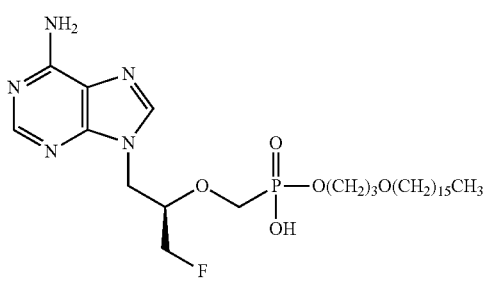
HDP-(R)-FPMPA
In some embodiments, a compound is selected from Table 3 following.
TABLE 3
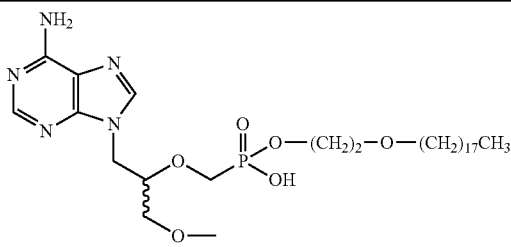
ODE-(RS)-MPMPA
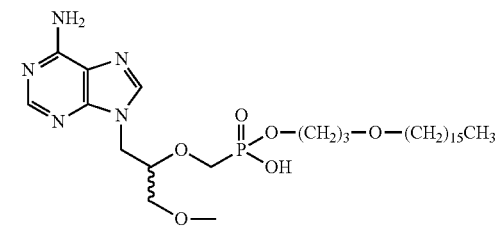
HDP-(RS)-MPMPA
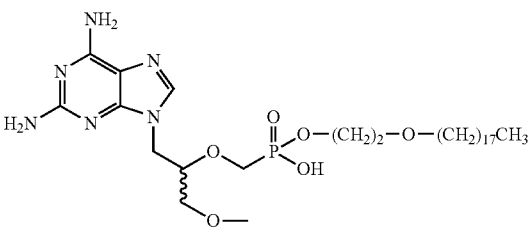
ODE-(RS)-MPMPDAP TABLE 3-continued

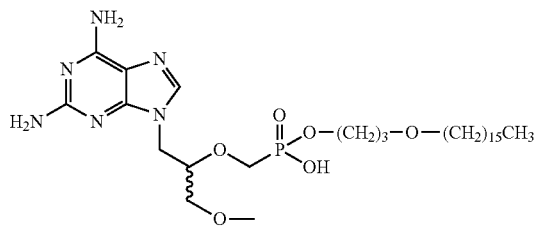

HDP-(RS)-MPMPDAP

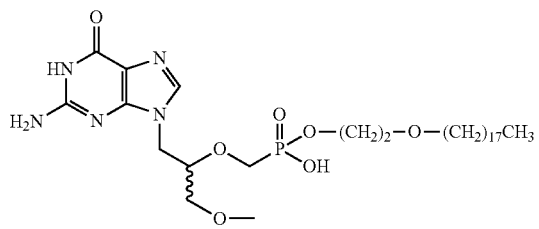

ODE-(RS)-MPMPG

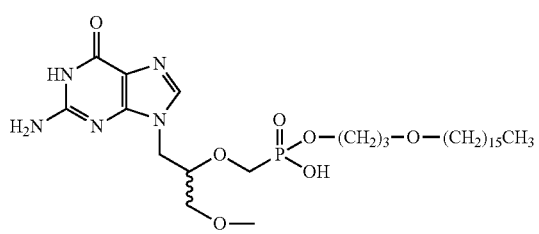

HDP-(RS)-MPMPG

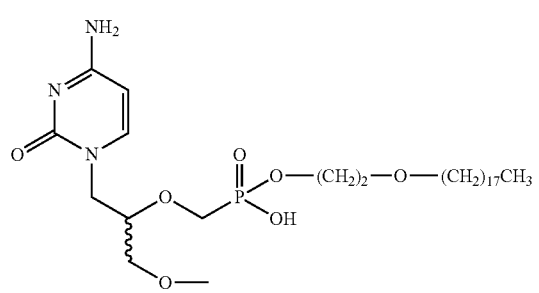

ODE-(RS)-MPMPC

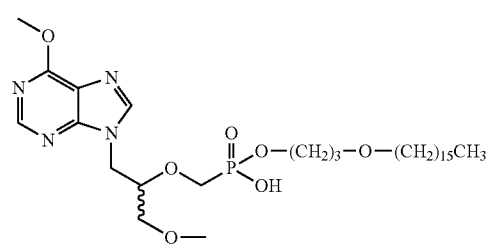

HDP-(RS)-MPMPMP

TABLE 3-continued

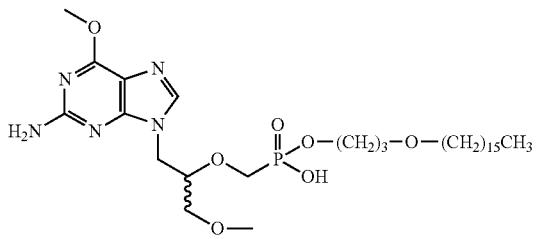

HDP-(RS)-MPMPOMG

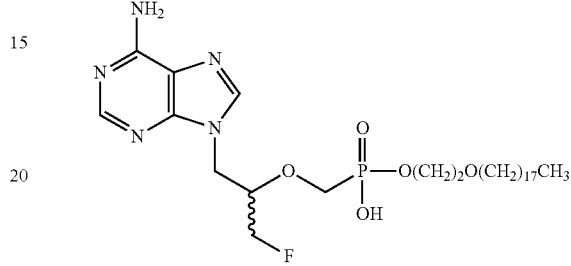

ODE-(RS)-FPMPA

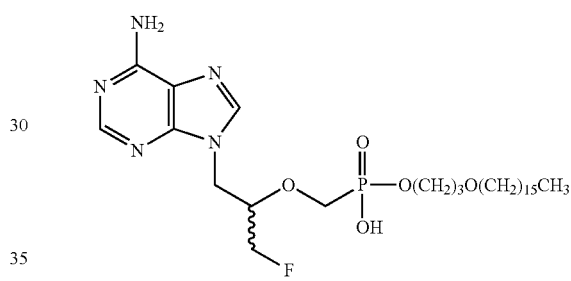

HDP-(RS)-FPMPA

Exemplary Syntheses

Synthesis of the new ANP analogs can be carried out using a synthon approach, e.g., the approach developed for alkoxyalkyl esters of (S)-9-[3-hydroxy-2-(phosphonomethoxy)-propyl]adenine [(S)-HPMPA]. See e.g., Beadle, J. R.; et al., 2006, Id. Exemplary of this approach is Scheme 1 (Example 1), wherein adenine can react with various alkyl glycidyl ethers under basic conditions to give a series of 9-(3-alkoxy-2-hydroxypropyl)adenines, e.g., Cmpds 2-5 (see Examples). After protection of the amino group with monomethoxytrityl, Cmpds 6-9 (see Examples) can be alkylated with octadecyloxyethyl or hexadecyloxypropyl p-toluenesulfonyloxymethyl-phosphonate, then deprotected to provide adenine derivatives Cmpds 15-19 (see Examples). As shown in Schemes 2 and 3 (see Examples), various 3-methoxy-2-phosphonomethoxypropyl (MPMP-) analogs of 2,6-diaminopurine (23-26) and guanine (34-37) can be prepared using similar methods. Additional schemes and experimental details for target Cmpds 40, 43 and 44 are provided in the Examples.

III. Methods of Use

The compounds provided herein are useful, inter alia, in inhibiting viral replication, including hepatitis C viruses. Examples below describe the synthesis of specific compounds of the invention. In particular the compound octadecyloxyethyl (S)-9-[(3-methoxy-2-phosphonomethoxy)propyl]adenine (ODE-(S)-MPMPA) has been tested and found to have potent inhibitory activity in HCV infected cells and in HIV-1 infected MT-2 cells. ODE-(S)-IPPMPA has been synthesized but has low activity against HCV. ODE-(S)-MPMPC has been synthesized and has antiviral activity against HIV-1 infected human peripheral blood mononuclear cells while hexadecyloxypropyl-(S)-MPMPG has submicromolar activity.

In another aspect, diphosphate metabolites of the compound of the invention may inhibit viral RNA-dependent RNA polymerases and thus inhibit the replication of the hepatitis C virus; they also inhibit replication of HIV-1 in vitro possibly due to inhibition of HIV reverse transcriptase.

Compounds described herein may be useful for treating human patients infected with an RNA virus, e.g., rotavirus, coronavirus, picornavirus, calicivirus, flavivirus, togavirus, or hepevirus; a DNA virus, e.g., herpesvirus, adenovirus, asfarvirus, polyomavirus, or poxvirus; or a retrovirus, e.g., alpharetrovirus, betaretrovirus, gammaretrovirus, deltaretrovirus, epsilonretrovus, lentivirus or spumavirus. In particular, compounds described herein may be useful for treating human patients infected with the hepatitis C virus or with a human retrovirus, such as HIV-1.

Compounds described herein may be useful for treating human patients infected with a disease caused by, or associated with, an RNA virus including a retrovirus, or a DNA virus.

In another aspect, the invention also provides processes and novel intermediates disclosed herein which are useful for preparing compounds of the invention. In other aspects, novel methods for synthesis, analysis, separation, isolation, purification, characterization, and testing of the compounds of this invention are provided.

In another aspect, a method of inhibiting a viral RNA-dependent RNA polymerase is provided. The method includes contacting a compound of Formula I or embodiment thereof wherein $R^2$ is a permeability enhancing moiety, or embodiments thereof, with a cell including a viral RNA-dependent RNA polymerase thereby inhibiting said viral RNA-dependent RNA polymerase.

In another aspect, there is provided a method of inhibiting a viral RNA-dependent RNA polymerase. The method includes contacting a viral RNA-dependent RNA polymerase with an effective amount of a compound of Formula (I) thereby inhibiting the viral RNA-dependent RNA polymerase.

In another aspect, there is provided a method of inhibiting a viral reverse transcriptase. The method includes contacting a viral reverse transcriptase with an effective amount of a compound of Formula (I) thereby inhibiting the viral RNA-dependent RNA polymerase.

In another aspect, a method of inhibiting a viral reverse transcriptase is provided. The method includes contacting a compound of Formula I or embodiment thereof wherein $R^2$ is a permeability enhancing moiety, or embodiments thereof, with a cell including a viral RNA-dependent RNA polymerase thereby inhibiting said viral RNA-dependent RNA polymerase.

In another aspect, a method of inhibiting replication of a hepatitis C virus or a human retrovirus is provided. The method includes contacting a compound of Formula I or embodiment thereof wherein $R^2$ is a permeability enhancing moiety, or embodiments thereof, with a cell infected with a hepatitis C virus or a human retrovirus thereby inhibiting replication of said hepatitis C virus or human retrovirus.

In another aspect, a method of inhibiting viral RNA-dependent RNA polymerase is provided. The method includes contacting (e.g. in vitro) a compound of Formula I or embodiment thereof wherein $R_2$ is a phosphate or diphosphate, or embodiments thereof, with a viral RNA-dependent RNA polymerase thereby inhibiting said viral RNA-dependent RNA polymerase.

In another aspect, a method of inhibiting viral reverse transcriptase is provided. The method includes contacting (e.g. in vitro) a compound of Formula I or embodiment thereof wherein $R^2$ is a phosphate or diphosphate, or embodiments thereof, with a reverse transcriptase thereby inhibiting said reverse transcriptase.

IV. Methods of Treating Disease

In another aspect, a method of treating a subject infected with a hepatitis C virus or a human retrovirus is provided. The method includes administering to a subject in need thereof an effective amount of a compound of Formula I or embodiment thereof wherein $R^2$ is a permeability enhancing moiety, or embodiments thereof. Diseases contemplated in the practice of the methods disclosed herein include diseases related to RNA viruses, e.g., SARS, poliomyelitis, the common cold, hepatitis A, yellow fever, West Nile Fever, West Nile meningitis, hepatitis C, Dengue fever, rubella, Ross River fever, sindbis fever, Chikungunya arthralgic disease, hepatitis E, Borna disease, Ebola hemorrhagic fever, Marburg hemorrhagic fever, measles, mumps, rabies, Lassa fever, Crimean-Congo hemorrhagic fever, and influenza. Additional diseases include those related to retroviruses, e.g., HIV, and diseases related to DNA viruses, e.g., herpes simplex, varicella zoster, African swine fever, cowpox, smallpox, hepatitis B, and progressive multifocal leukoencephalopathy, V. Pharmaceutical Compositions In another aspect, the present invention provides pharmaceutical compositions. The pharmaceutical composition includes a pharmaceutically acceptable excipient and a compound of the present invention (e.g. Formula I or embodiments thereof)).

The pharmaceutical compositions described herein are typically used to treat a disorder or condition using known methods of nucleic acid pharmaceutical antiviral therapies.

In an exemplary embodiment, the pharmaceutical composition includes from 1 µg to 2000 mg of a compound disclosed herein, e.g., 1 µg to 1 mg, 1 mg to 10 mg, 1 mg to 100 mg, 1 mg to 1000 mg, 1 mg to 1500 mg, or even 1 mg to 2000 mg.

A. Formulations

The compounds of the present invention can be prepared and administered in a wide variety of oral, parenteral and topical dosage forms. Oral preparations include tablets, pills, powder, dragees, capsules, liquids, lozenges, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. The compounds of the present invention can also be administered by in intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Thus, the pharmaceutical compositions described herein may be adapted for oral administration. In some embodiments, the pharmaceutical composition is in the form of a tablet. Moreover, the present invention provides pharmaceutical compositions including a pharmaceutically acceptable carrier or excipient and either a compound of the present invention, or a pharmaceutically acceptable salt of a compound of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of REMINGTON'S PHARMACEUTICAL SCIENCES, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Suitable solid excipients are carbohydrate or protein fillers include, but are not limited to, sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain compounds of Formulae I or II mixed with a filler or binders such as lactose or starches, lubricants such as talc or magnesium stearate, and, optionally, stabilizers. In soft capsules, the compounds may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending a compound in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compounds can be delivered by transdermally, by a topical route, formulated as applicator sticks, solutions, suspensions, emulsions, gels, creams, ointments, pastes, jellies, paints, powders, and aerosols.

The compounds can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The compounds can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use In another embodiment, the compounds are useful for parenteral administration, such as intravenous (IV) administration or administration into a body cavity or lumen of an organ. The formulations for administration will commonly comprise a solution of the compound dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compound in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the compound can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compound into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Compounds of the invention may be metabolized by cells by phosphatases of the phospholipase C type and then converted by anabolic phosphorylation sequentially to the acyclic nucleoside phosphonate monophosphate (ANPp) and then to the acyclic nucleoside phosphonate diphosphate, (ANPpp), the active antiviral. For example ODE-(S)-MP-MPA is metabolized intracellularly in mammalian cells as shown in Scheme A following, wherein "a" is a phosphatase of the phospholipase or lysophospholipase C type; "b" is a nucleoside monophosphate kinase, and "c" is a nucleoside diphosphate kinase. ODE-(S)-MPMPA, (S)-MPMPAp and (S)-MPMPApp are unique chemical entities and are compounds described herein.

Scheme A.

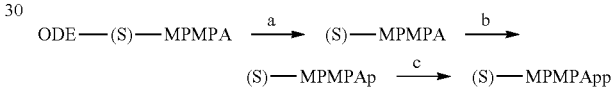

B. Effective Dosages

Pharmaceutical compositions provided herein include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat virus infection, such compositions will contain an amount of active ingredient effective to achieve the desired result (e.g. decreasing the viral titer).

The dosage and frequency (single or multiple doses) of compound administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds described herein.

For any compound described herein, the therapeutically effective amount can be initially determined from cell culture assays. Target concentrations will be those concentrations of active compound(s) that are capable of decreasing viral activity as measured, for example, using the methods described.

Therapeutically effective amounts for use in humans may be determined from animal models. For example, a dose for humans can be formulated to achieve a concentration that has been found to be effective in animals. The dosage in humans can be adjusted by monitoring viral inhibition and adjusting the dosage upwards or downwards, as described above.

Dosages may be varied depending upon the requirements of the patient and the compound being employed. The dose administered to a patient, in the context of the present invention, should be sufficient to affect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In one embodiment of the invention, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

C. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

VI. Examples

The examples below are meant to illustrate certain embodiments of the invention, and not to limit the scope of the invention. Abbreviations: (S)-HPMPA, 9-(S)-[3-hydroxy-2-(phosphonomethoxy)propyl]adenine; (S)-MPMPA, 9-(S)-[3-methoxy-2-(phosphonomethoxy)propyl]adenine; ODE, octadecyloxyethyl; HDP, hexadecyloxypropyl; ODE-(S)-MPMPA, octadecyloxyethyl 9-(S)-[3-methoxy-2-(phosphonomethoxy) propyl]adenine; ODE-(R)-MPMPA, octadecyloxyethyl 9-(R)-[3-methoxy-2-(phosphonomethoxy)propyl]adenine; HDP-(S)-MPMPA, hexadecyloxypropyl 9-(S)-[3-methoxy-2-(phosphonomethoxy)propyl]adenine; HDP-(R,S)-EPMPA, hexadecyloxypropyl 9-(R,S)-[3-ethoxy-2-(phosphonomethoxy)propyl]adenine; HDP-(R,S)-IPPMPA, hexadecyloxypropyl 9-(R,S)-[3-isopropoxy-2-(phosphonomethoxy)propyl]adenine; ODE-(S)-MPMPDAP, octadecyloxyethyl 9-(S)-[3-methoxy-2-(phosphonomethoxy)propyl]2,6-diaminopurine; HDP-(R,S)-EPMPDAP, hexadecyloxypropyl 9-(R,S)-[3-ethoxy-2-(phosphonomethoxy)propyl]2,6-diaminopurine; ODE-(S)-MPMPG, octadecyloxyethyl 9-(S)-[3-methoxy-2-(phosphonomethoxy)propyl]guanine; ODE-(S)-MPMPC, octadecyloxyethyl 1-(S)-[3-methoxy-2-(phosphonmethoxy)propyl]cytosine; HDP-(S)-MPMPMP, hexadecyloxypropyl 9-(S)-[3-methoxy-2-(phosphonomethoxy)propyl]6-methoxypurine; HDP-(S)-MPMPOMG, hexadecyloxypropyl 9-(S)-[3-methoxy-2-(phosphonomethoxy)propyl]6-O-methylguanine General.

All reagents were of commercial quality and used without further purification unless indicated otherwise. Chromatographic purification was done using the flash method with silica gel 60 (EMD Chemicals, Inc., 230-400 mesh). $^1$H NMR spectra were recorded on Varian HG spectrophotometers operating at 400 MHz and are reported in units of parts per million (ppm) relative to internal tetramethylsilane at 0.00 ppm. Assignments of $^1$H NMR signals are made using the numbering system shown in Scheme B following.

Scheme B. Numbering System for NMR Signal Assignment

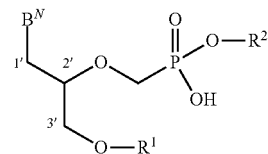

Routine electrospray ionization mass spectra (ESI-MS) were recorded on a Finnigan LCQDECA spectrometer, and high resolution mass spectra (HRMS) on an Agilent 6230 Accurate-Mass TOFMS mass spectrometer in ESI negative mode. Purity of the target compounds was characterized by high performance liquid chromatography (HPLC) using a Beckman Coulter System Gold chromatography system. The analytical column was Phenomenex Synergi™ Polar-RP (4.6×150 mm) equipped with a SecurityGuard™ protection column. Mobile phase A was 95% water/5% methanol and mobile phase B was 95% methanol/5% water. At a flow rate of 0.8 mL/min, gradient elution was as follows: 10% B (0-3 min.); 10% to 95% B (3-20 min.); 95% B (20-25 min.); 95% to 10% B (25-34 min.). Compounds were detected by ultraviolet light (UV) absorption at 274 nm. Purity of compounds was also assessed by thin layer chromatography (TLC) using Analtech silica gel-GF (250 μm) plates and the solvent system: $CHCl_3$/MeOH/con $NH_4OH/H_2O$ (70:30:3:3 v/v). TLC results were visualized with UV light, phospray (Supelco, Bellefonte, Pa., USA) and charring at 400° C. The key synthons, hexadecyloxypropyl- and octadecyloxyethyl p-toluenesulfonyloxymethylphosphonate, were prepared as described previously. See e.g., Beadle, et al., 2006, Id.

Compounds.

Compound numbering as used herein is provided in Table 4 following which sets forth substituents $B^N$, $R^1$ and $R^2$ of Formula (I), structure, and common name abbreviation.

TABLE 4
| Cmpd | B^N | R^1 | R^2 | Structure name, |
|---|---|---|---|---|
| 1 | adenine | H | ODE | 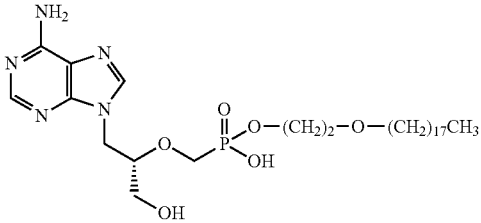 ODE-(S)-HPMPA |
| 15 | | Me | ODE | 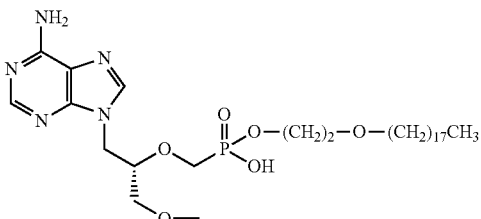 ODE-(S)-MPMPA |
| 16 | | Me | ODE | 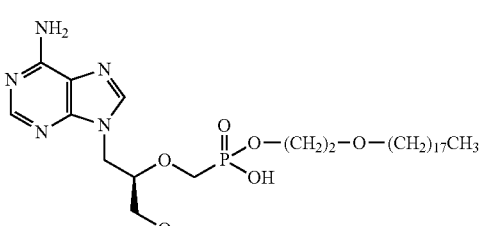 ODE-(R)-MPMPA |
| 17 | | Me | HDP | 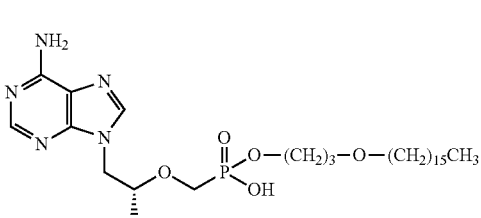 HDP-(S)-MPMPA |
| 18 | | ethyl | HDP | 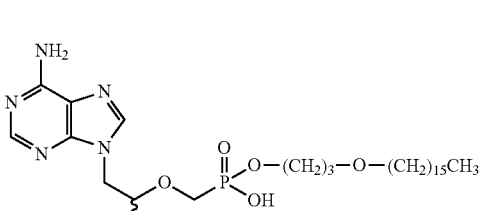 HDP-(R,S)-EPMPA |

TABLE 4-continued
| Cmpd | B^N | R^1 | R^2 | Structure name, |
|---|---|---|---|---|
| 19 | | isopropyl | HDP | 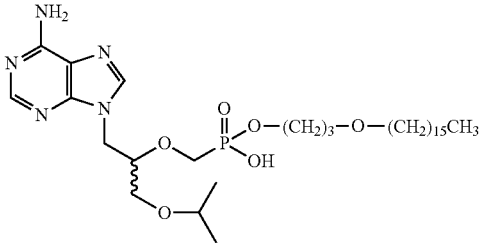 HDP-(R,S)-IPPMPA |
| 23 | 2,6-diamino-purine | Me | ODE | 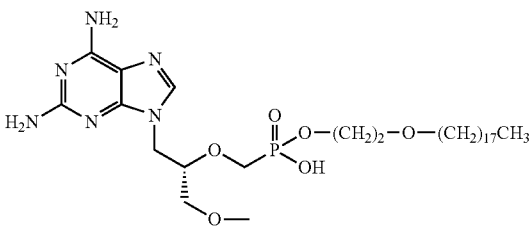 ODE-(S)-MPMPDAP |
| 24 | | Me | ODE | 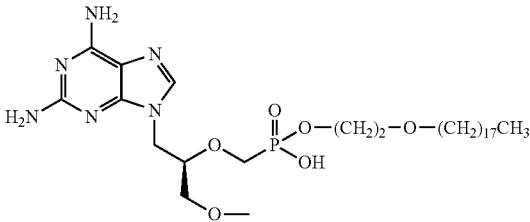 ODE-(R)-MPMPDAP |
| 25 | | Me | HDP | 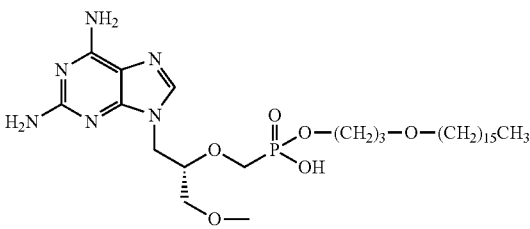 HDP-(S)-MPMPDAP |
| 26 | | ethyl | HDP | 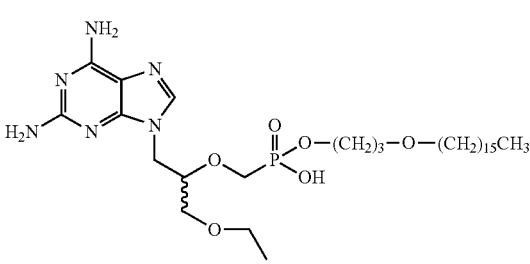 HDP-(R,S)-PMPDAP |

TABLE 4-continued
| Cmpd | B^N | R^1 | R^2 | Structure name, |
|---|---|---|---|---|
| 34 | guanine | Me | ODE | 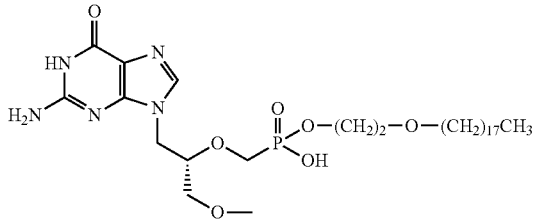 ODE-(S)-MPMPG |
| 35 | | Me | ODE | 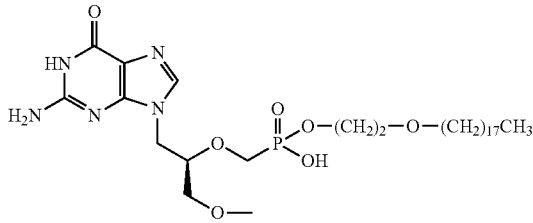 ODE-(R)-MPMPG |
| 36 | | Me | HDP | 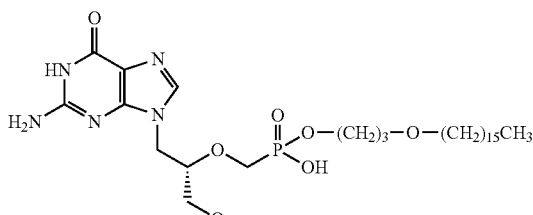 HDP-(S)-MPMPG |
| 37 | | ethyl | HDP | 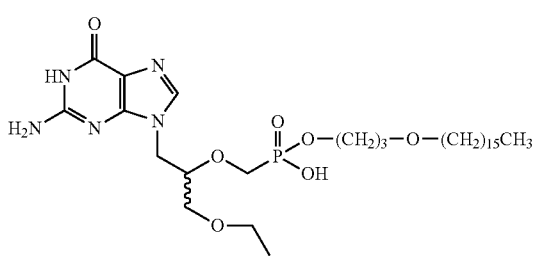 HDP-(R,S)-EPMPG |

TABLE 4-continued

| Cmpd | B$^N$ | R$^1$ | R$^2$ | Structure name, |
|---|---|---|---|---|
| 40 | cytosine | Me | ODE | 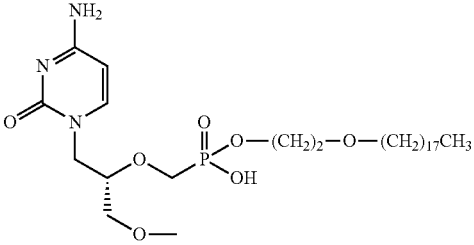 ODE-(S)-MPMPC |
| 43 | 6-methoxy-purine | Me | HDP | 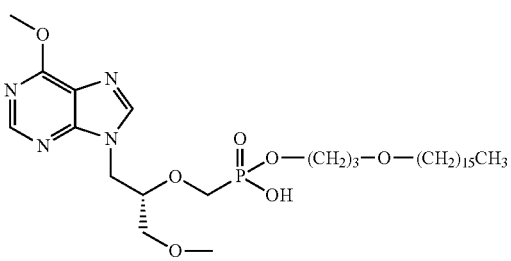 HDP-(S)-MPMPMP |
| 44 | 6-O-methyl-guanine | Me | HDP | 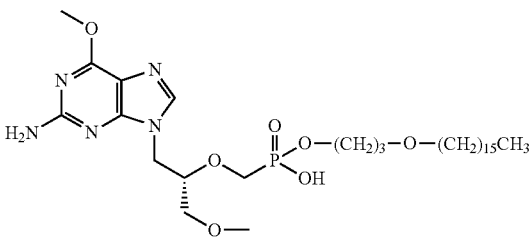 HDP-(S)-MPMPOMG |

Example 1

General Procedure A. Synthesis of 3-alkoxy-2-hydroxypropyl nucleoside analogs

The preparation of 3-alkoxy-2-hydroxypropyl nucleoside analogs was accomplished using the base catalyzed ring-opening reaction of alkyl glycidyl ethers with nucleobases as described by Brodfuehrer et al. See Brodfuehrer, P. R., et al., 1994, *Tetrahedron Lett.* 35:3243-3246. Sodium hydride (2 mmol) was added to a solution of the nucleic acid base (10 mmol) and an alkyl glycidyl ether (10 mmol) in anhydrous N,N-dimethylformamide (50 mL) and the mixture was stirred and heated to 100° C. for 6 hours. After cooling, the reaction was quenched with H$_2$O, the solvent was removed in vacuo and the residue was purified by flash column chromatography on silica gel. Elution of the column with 10% MeOH/CH$_2$Cl$_2$ gave the product.

With reference to Scheme 1 following, reagents were the following: a) NaH, alkyl glycidyl ether, N,N-DMF, 100° C., 6 h; b) bromotrimethylsilane, monomethoxytrityl chloride, pyridine; c) sodium t-butoxide, hexadecyloxypropyl (HDP) or octadecyloxyethyl (ODE) p-toluenesulfonyloxymeth-ylphosphonate, N,N-DMF, 80° C., 16 h; d) 80% aq acetic acid, 60° C., 2 h.

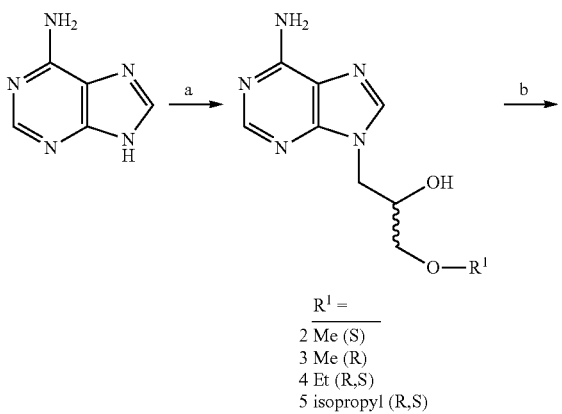

Scheme 1. General procedure A. Exemplary Synthesis of Adenine-Containing Compounds (15-19).

R$^1$ =
2 Me (S)
3 Me (R)
4 Et (R,S)
5 isopropyl (R,S)

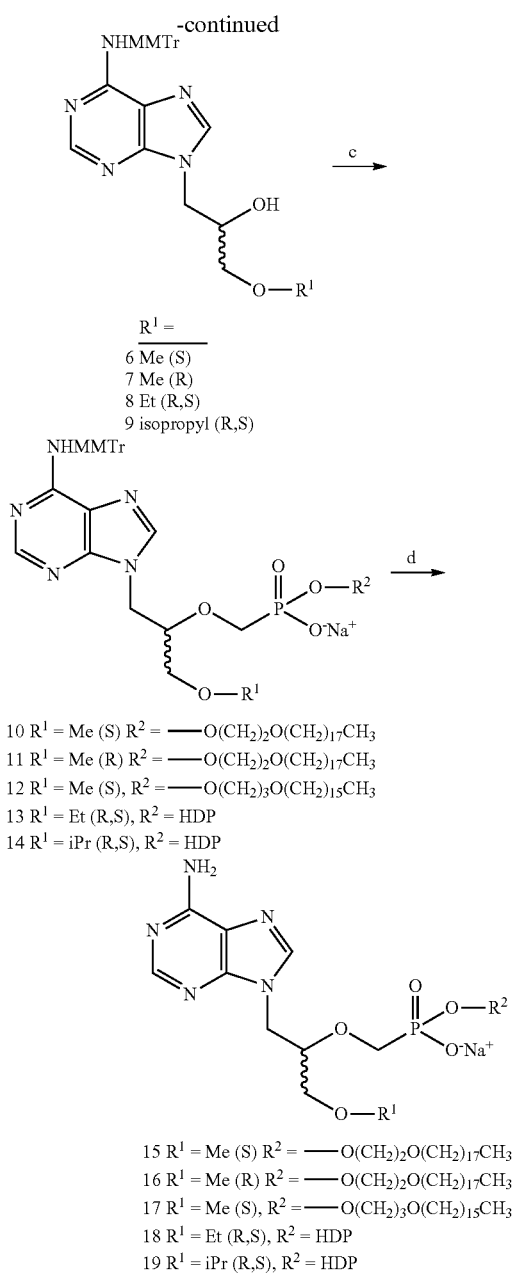

America, Portland, Oreg.). 72% yield. $^1$H NMR (methanol-$d_4$) δ 8.20 (s, 1H, H-8); 8.08 (s, 1H, H-2); 4.39 (dd, 1H, H-1'a, $J_{1'a,240}$=3.4 Hz, $J_{gem}$=14.2 Hz); 4.20 (dd, 1H, H-1'b, $J_{1'b,2'}$=8.0 Hz, $J_{gem}$=14.2 Hz); 4.11 (m, 1H, H-2'); 3.42 (d, 2H, H-3', $J_{3',2'}$=5.2 Hz); 3.37 (s, 3H, —OCH$_3$).

Example 4

(R,S)-9-[(3-ethoxy-2-hydroxy)propyl]adenine (4)

(R,S)-9-[(3-ethoxy-2-hydroxy)propyl]adenine (4) was synthesized from adenine and (R,S)-ethyl glycidyl ether (TCI America) with 59% yield. $^1$H NMR (CDCl$_3$/methanol-$d_4$), δ:8.24 (s, 1H); 8.04 (s, 1H); 4.40-4.65 (m, 1H); 4.20-4.27 (m, 1H); 4.10-4.15 (m, 1H); 3.55-3.57 (m, 2H); 3.46-3.54 (m, 2H); 1.21 (t, J=7 Hz, 3H). MS (ESI): 238.09 [M+H]$^+$.

Example 5

(R,S)-9-[(3-isopropoxy-2-hydroxy)propyl]adenine (5)

(R,S)-9-[(3-isopropoxy-2-hydroxy)propyl]adenine (5) was synthesized from adenine and (R,S) isopropyl glycidyl ether (Aldrich Chem.). 33.8% yield. $^1$H NMR (CDCl$_3$/methanol-$d_4$), δ 8.21 (s, 1H, H-8); 8.08 (s, 1H, H-2); 4.41 (dd, 1H, H-1'a, $J_{1'a,2'}$=3.8, $J_{gem}$=14.2 Hz); 4.23 (dd, 1H, H-1'b, $J_{1'b,2'}$=7.6 Hz, $J_{gem}$=14.4 Hz); 4.10 (m, 1H, H-2'); 3.60 (septet, 1H, —CH(CH$_3$)$_2$, J=6.0 Hz); 1.16 (d, 6H, —CH(CH$_3$)$_2$).

Example 6

General Procedure B. Synthesis of 9-[(3-alkoxy-2-hydroxy)propyl]-N6-monomethoxytrityladenine (6-9)

The monomethoxytrityl group was used to block the exocylic amino group of adenine and was introduced by the transient protection method described by Ti et al.[3] Bromotrimethylsilane (6.3 mmol) was added dropwise to a suspension of 9-[(2-hydroxy-3-alkoxy)propyl]adenine (2-5) (2.8 mmol) in dry pyridine (10 mL). The mixture was stirred 15 min. until it became clear, then monomethoxytrityl chloride (0.99 g, 3.2 mmol) and 4-(dimethylamino)pyridine (20 mg, 0.2 mmol) were added and stirring was continued overnight. The mixture was cooled with an ice bath and H$_2$O (1 mL) was added. Stirring was continued 10 min., then con. NH$_4$OH (1 mL) was added and the reaction was stirred 30 additional min. The mixture was allowed to warm to room temperature and filtered through a pad of Celite®. The filtrate was evaporated in vacuo and the residue was purified by flash column chromatography on silica gel. Gradient elution (100% hexanes to 100% ethyl acetate) afforded the N$^6$-monomethoxytrityl 9-[(2-alkoxy-3-methoxy)propyl]adenines (6-9).

Example 7

(S)-9-[(3-methoxy-2-hydroxy)propyl]-N6-monomethoxytrityladenine (6)

(S)-9-[(3-methoxy-2-hydroxy)propyl]-N$^6$-monomethoxytrityladenine (6) was synthesized from 2. 98% yield. $^1$H NMR (CDCl$_3$/methanol-$d_4$), δ 8.17 (s, 1H, H-8); 8.13 (s, 1H, H-2); 7.39-7.75 (m, 14H, trityl); 4.50-4.59 (m, 1H); 4.31-4.39 (m, 1H); 4.22-4.30 (m, 1H); 3.45 (s, 3H); 3.50-3.60 (m, 2H); 3.55 (s, 3H). MS (ESI): 496.06 [M+H]$^+$, 518.13 [M+Na]$^+$.

Example 2

(S)-9-[(3-methoxy-2-hydroxy)propyl]adenine (2)

(S)-9-[(3-methoxy-2-hydroxy)propyl]adenine (2) was synthesized from adenine and (S)-methyl glycidyl ether (TCI America, Portland, Oreg.). 75% yield. $^1$H NMR (CDCl$_3$/methanol-$d_4$) δ 8.25 (s, 1H); 8.03 (s, 1H); 4.39-4.44 (m, 1H); 4.19-4.25 (m, 1H); 4.08-4.18 (m, 1H); 3.37-3.44 (m, 2H); 3.40 (s, 3H). MS (ESI): 224.14 [M+H]$^+$.

Example 3

(R)-9-[(3-methoxy-2-hydroxy)propyl]adenine (3)

(R)-9-[(3-methoxy-2-hydroxy)propyl]adenine (3) was synthesized from adenine and (R)-methyl glycidyl ether (TCI

Example 8

(R)-9-[(3-methoxy-2-hydroxy)propyl]N6-monomethoxytrityladenine (7)

(R)-9-[(3-methoxy-2-hydroxy)propyl]N$^6$-monomethoxytrityladenine (7) was synthesized from Cmpd 3. 19% yield. $^1$H NMR (CDCl$_3$/methanol-d$_4$), δ 8.03 (s, 1H, H-8); 7.78 (s, 1H, H-2); 7.35-7.33 (m, 4H, trityl); 7.29-7.24 (m, 10H, trityl); 4.61 (d, 1H, H-1'a, J$_{1'a,2'}$=4 Hz); 4.39 (dd, 1H, H-1'b, J$_{1'b,2'}$=2.2 Hz, J$_{gem}$=13.8 Hz); 4.16 (m, 1H, H-2'); 3.78 (s, 3H, Ar—OCH$_3$); 3.41 (dd, 1H, H-3'a, J$_{3'a,2'}$=5.2 Hz, J$_{gem}$=9.2 Hz); 3.36 (s, 3H, CH$_2$—OCH$_3$); 3.33 (dd, 1H, H-3'b, J$_{3'b,2'}$=6.2 Hz, J$_{gem}$=9.8 Hz).

Example 9

(R,S)-9-[(3-ethoxy-2-hydroxy)propyl]N6-monomethoxytrityladenine (8)

(R,S)-9-[(3-ethoxy-2-hydroxy)propyl]N$^6$-monomethoxytrityladenine (8) was synthesized from 4. 78% yield. $^1$H NMR (CDCl$_3$/methanol-d$_4$), δ 7.98 (s, 1H); 7.25-7.34 (m, 14H); 6.82 (s, 1H); 4.35-4.43 (m, 1H); 4.15-4.24 (m, 1H); 4.05-4.15 (m, 1H); 3.78 (s, 3H); 3.52-3.56 (m, 2H); 3.44-3.47 (m, 2H); 1.20 (t, J=7 Hz, 3H). MS (ESI): 509.78 [M+H]$^+$.

Example 10

(R,S)-9-[(3-isopropoxy-2-hydroxy)propyl]N6-monomethoxytrityladenine (9)

(R,S)-9-[(3-isopropoxy-2-hydroxy)propyl]N$^6$-monomethoxytrityladenine (9) was synthesized from Cmpd 5. 32% yield. $^1$H NMR (DMSO-d$_6$) δ 8.10 (s, 1H, H-8); 7.89 (s, 1H, H-2); 7.28-7.26 (m, 10H, trityl); 7.21-7.18 (m, 4H, trityl); 6.83 (d, 1H, —NH—); 5.16 (d, 1H, —OH); 4.23 (dd, 1H, H-1'a, J$_{1'a,2'}$=3.4 Hz, J$_{gem}$=13.8 Hz); 3.98 (dd, 1H, H-1'b, J$_{1'b,2'}$=8.4 Hz, J$_{gem}$=13.6 Hz); 3.92 (m, 1H, H-2'); 3.70 (s, 3H, Ar—OCH$_3$); 3.50 (septet, 1H, —CH(CH$_3$)$_2$); 3.35 (dd, 1H, J$_{3'a,2'}$=4.8 Hz, J$_{gem}$=10 Hz); 3.27 (dd, 1H, H-3'b, J$_{3'b,2'}$=6, J$_{gem}$=9.6); 1.04 (dd, 6H, —CH(CH$_3$)$_2$).

Example 11

General Procedure C. Alkylation of 9-[(3-alkoxy-2-hydroxy)propyl]derivatives (6-9, 20-22, 27-29, 38, 41-42) with alkoxyalkyl p-toluenesulfonyloxymethylphosphonate. Synthesis of (10-14, 23-26, 30-33, 39, 43-44)

Sodium t-butoxide (0.19 g, 2.0 mmol) was added to a solution of the 3-alkoxy-2-hydroxypropyl nucleoside (1.0 mmol) and the alkoxyalkyl p-toluenesulfonyloxymethylphosphonate[1] (2.0 mmol) in anhydrous N,N-DMF (20 mL). The mixture was heated to 80° C. and kept overnight. After cooling, the solvents were evaporated in vacuo and the residue was purified by flash column chromatography on silica gel. The column was eluted with a gradient: chloroform 100%—chloroform-methanol (20%) to give the products.

Example 12

Octadecyloxyethyl (S)-9-[(3-methoxy-2-phosphonomethoxy)propyl]N6-monomethoxytrityladenine, sodium salt (10)

Octadecyloxyethyl (S)-9-[(3-methoxy-2-phosphonomethoxy)propyl]N$^6$-monomethoxytrityladenine, sodium salt (10) was synthesized from (S)-9-[(3-methoxy-2-hydroxy)propyl]-N$^6$-monomethoxytrityladenine (6) and octadecyloxyethyl p-toluenesulfonyloxymethylphosphonate. 60% yield. $^1$H NMR (CDCl$_3$/methanol-d$_4$), δ 8.18 (s, 1H); 7.98 (s, 1H); 7.22-7.55 (m, 14H); 4.38-4.50 (m, 2H); 4.12-4.37 (m, 2H); 4.00-4.08 (m, 1H); 3.82-3.98 (m, 2H); 3.79 (s, 3H); 3.58-3.65 (m, 2H); 3.44-3.48 (m, 2H); 3.38-3.43 (m, 2H); 3.35 (s, 3H); 1.40-1.60 (m, 2H); 1.16-1.38 (m, 30H); 0.88 (t, J=7 Hz, 3H). MS (ESI): 886.48 [M+H]$^+$.

Example 13

Octadecyloxyethyl (R)-9-[(3-methoxy-2-phosphonomethoxy)propyl]N6-monomethoxytrityladenine, sodium salt (11)

Octadecyloxyethyl (R)-9-[(3-methoxy-2-phosphonomethoxy)propyl]N$^6$-monomethoxytrityladenine, sodium salt (11) was synthesized from (R)-9-[(3-methoxy-2-hydroxy)propyl]-N$^6$-monomethoxytrityladenine (7) and octadecyloxyethyl p-toluenesulfonyloxymethylphosphonate. 43% yield. $^1$H NMR (CDCl$_3$/methanol-d$_4$), δ 8.20 (s, 1H); 7.98 (s, 1H); 7.22-7.37 (m, 14H); 4.42-4.50 (m, 1H); 4.28-4.37 (m, 1H); 3.91-3.98 (m, 2H); 3.82-3.90 (m, 2H); 3.79 (s, 3H); 3.60-3.69 (m, 1H); 3.48-3.58 (m, 3H); 3.39-3.46 (m, 2H); 3.35 (s, 3H); 1.45-1.60 (m, 2H); 1.20-1.38 (m, 30H); 0.88 (t, J=7Hz, 3H). MS (ESI): 886.57 [M+H]$^+$.

Example 14

Hexadecyloxypropyl (S)-9-[(3-methoxy-2-phosphonomethoxy)propyl]N6-monomethoxytrityladenine, sodium salt (12)

Hexadecyloxypropyl (S)-9-[(3-methoxy-2-phosphonomethoxy)propyl]N$^6$-monomethoxytrityladenine, sodium salt (12) was synthesized from (S)-9-[(3-methoxy-2-hydroxy)propyl]-N$^6$-monomethoxytrityladenine (6) and hexadecyloxypropyl p-toluenesulfonyloxymethylphosphonate. 77% yield. $^1$H NMR (CDCl$_3$/methanol-d$_4$), δ: 8.17 (s, 1H); 7.94 (s, 1H); 7.22-7.36 (m, 14H); 4.38-4.50 (m, 2H); 4.28-4.37 (m, 2H); 3.82-3.98 (m, 2H); 3.79 (s, 3H); 3.58-3.65 (m, 1H); 3.38-3.58 (m, 6H); 3.34 (s, 3H); 1.78-1.87 (m, 2H); 1.44-1.60 (m, 2H); 1.10-1.40 (m, 26H); 0.88 (t, J=7 Hz, 3H). MS (ESI): 870.33 [M−H]$^−$.

Example 15

Hexadecyloxypropyl (R,S)-9-[(3-ethoxy-2-phosphonomethoxy)propyl]N6-monomethoxytrityladenine, sodium salt (13)

Hexadecyloxypropyl (R,S)-9-[(3-ethoxy-2-phosphonomethoxy)propyl]N$^6$-monomethoxytrityladenine, sodium salt (13) was synthesized from (R,S)-9-[(3-ethoxy-2-hydroxy)propyl]-N$^6$-monomethoxytrityladenine (8) and hexadecyloxypropyl p-toluenesulfonyloxymethylphosphonate. 80% yield. $^1$H NMR (CDCl$_3$/methanol-d$_4$), δ: 8.19 (s, 1H); 7.98 (s, 1H); 7.20-7.36 (m, 14H); 4.42-4.65 (m, 1H); 4.28-4.37 (m, 1H); 3.80-3.95 (m, 3H); 3.78 (s, 3H); 3.48-3.65 (m, 6H); 3.28-3.48 (m, 2H); 1.78-1.87 (m, 2H); 1.44-1.55 (m, 2H); 1.08-1.30 (m, 26H); 1.15 (t, J=7 Hz, 3H); 0.88 (t, J=7 Hz, 3H). MS (EI): 886.42 (M+H)$^−$.

Example 16

Hexadecyloxypropyl (R,S)-9-[(3-isopropoxy-2-phosphonomethoxy)propyl]N6-monomethoxytrityladenine, sodium salt (13)

Hexadecyloxypropyl (R,S)-9-[(3-isopropoxy-2-phosphonomethoxy)propyl]N$^6$-monomethoxytrityladenine, sodium salt (13) was synthesized from (R,S)-9-[(3-isopropoxy-2-hydroxy)propyl]-N$^6$-monomethoxytrityladenine (9) and hexadecyloxypropyl p-toluenesulfonyloxymethylphosphonate. 25% yield. $^1$H NMR (CDCl$_3$/methanol-d$_4$) δ 8.15 (s, 1H, H-8); 7.88 (s, 1H, H-2); 7.30-7.25 (m, 4H, trityl); 7.20-7.12 (m, 10H, trityl); 4.66 (dd, 1H, H-1'a, J$_{1'a,2'}$=3.5 Hz, J$_{gem}$=14.2 Hz); 4.47 (dd, 1H, H-1'b, J$_{1'b,2'}$=6.2 Hz, J$_{gem}$=14.0 Hz); 4.01 (m, 2H, —P—O—CH$_2$—); 3.88 (dd, 1H, —CH$_a$—P—, J$_{P,CHa}$=9.2 Hz, J$_{gem}$=13.6 Hz); 3.71 (dd, 1H, —CH$_b$—P—, J$_{P,CHb}$=9.6 Hz, J$_{gem}$=14.0 Hz); 3.75-3.55 (m, 3H, H-3'+H-2'); 3.51 (t, 2H, —CH$_2$—O—CH$_2$—); 3.45 (t, 2H, —CH$_2$—O—CH$_2$—); 1.83 (pentet, 2H, —O—CH$_2$CH$_2$CH$_2$O—); 1.53 (m, 2H, —CH$_2$(CH$_2$)$_{15}$—); 1.27 (m, 26H, —(CH$_2$)$_{15}$—); 1.10 (d, 6H, —CH(CH$_3$)$_2$); 0.89 (t, 3H, —CH$_3$).

Example 17

General Procedure D. Synthesis of Alkoxyalkyl-9-[(3-alkoxy-2-phosphonomethoxy)propyl]adenine (15-19)

Alkoxyalkyl 9-[(3-alkoxy-2-hydroxy)propyl]-N$^6$-monomethoxytrityladenine (10-14) (0.60 mmol) was added to 80% acetic acid, stirred and heated to 60° C. for 2 hours. After cooling, the solvent was removed in vacuo and the residue purified by flash column chromatography on silica gel. Elution with 20% MeOH/CH$_2$Cl$_2$ gave the products.

Example 18

Octadecyloxyethyl (S)-9-[(3-methoxy-2-phosphonomethoxy)propyl]adenine, sodium salt (ODE-(S)-MPMPA) (15)

Octadecyloxyethyl (S)-9-[(3-methoxy-2-phosphonomethoxy)propyl]adenine, sodium salt (ODE-(S)-MPMPA) (15). Deprotection of Cmpd 10 (procedure D) gave Cmpd 15 in 73% yield as a white powder. $^1$H NMR (CDCl$_3$/methanol-d$_4$) δ 8.35 (s, 1H, H-8); 8.22 (s, 1H, H-2); 4.53 (dd, H, H-1'a, J$_{1'a2'}$=3.3 Hz, J$_{gem}$ 14.3 Hz); 4.37 (dd, 1H, H-1'b, J$_{1'b2'}$=6.6 Hz, J$_{gem}$ 14.7 Hz); 4.01-3.98 (m, 3H, P—O—CH$_2$-+H-2'); 3.87 (dd, 1H, —CH$_a$—P—, J$_{P,CHa}$=9.2 Hz, J$_{gem}$=13.2); 3.70 (dd, 1H, —CH$_b$—P—, J$_{P,CHb}$=9.0 Hz, J$_{gem}$=13.0 Hz); 3.57 (t, 2H, —CH$_2$—O—); 3.44 (t, 2H, —O—CH$_2$—); 1.53 (m, 2H, —O—CH$_2$CH$_2$(CH$_2$)$_{15}$—); 1.26 (m, 30H, —(CH$_2$)$_{15}$CH$_3$); 0.89 (t, 3H, —CH$_3$, J=7 Hz). MS (ESI+): 614.41 [M+H]$^+$; HRMS (ESI−) calcd. for C$_{30}$H$_{55}$N$_5$O$_6$P [M−H]$^-$ 612.3895, found 612.3897 (E=0.3 ppm). HPLC analysis: retention time 22.35 min., purity 96.12%.

Example 19

Octadecyloxyethyl (R)-9-[(3-methoxy-2-phosphonomethoxy)propyl]adenine, sodium salt (ODE-(R)-MPMPA) (16)

Octadecyloxyethyl (R)-9-[(3-methoxy-2-phosphonomethoxy)propyl]adenine, sodium salt (ODE-(R)-MPA) (16). Deprotection of 11 gave 16 in 72% yield. $^1$H NMR (CDCl$_3$/methanol-d$_4$), δ: 8.24 (s, 1H); 8.21 (s, 1H); 4.43-4.54 (s, 1H); 4.25-4.35 (m, 1H); 3.88-3.98 (m, 3H); 3.80-3.88 (m, 1H); 3.50-3.60 (m, 4H); 3.38-3.48 (m, 3H); 3.37 (s, 3H); 1.49-1.56 (m, 2H); 1.20-1.35 (m, 30H); 0.88 (t, J=7Hz, 3H). MS (ESI+): 614.55 [M+H]$^+$, 636.46 [M+Na]$^+$. HRMS (ESI−) calcd. for C$_{30}$H$_{55}$N$_5$O$_6$P [M−H]$^-$ 612.3895, found 612.3900 (E=0.8 ppm). HPLC analysis: retention time 21.82 min., purity 95.24%.

Example 20

Hexadecyloxypropyl (S)-9-[3-methoxy-2-phosphonomethoxy)propyl]adenine, sodium salt (HDP-(S)-MPMPA) (17)

Hexadecyloxypropyl (S)-9-[3-methoxy-2-phosphonomethoxy)propyl]adenine, sodium salt (HDP-(S)-MPMPA) (17). Deprotection of 12 gave 17 in 77% yield. $^1$H NMR (CDCl$_3$/methanol-d$_4$), δ 8.28 (s, 1H); 8.23 (s, 1H); 4.48-4.61 (s, 2H); 4.32-4.37 (m, 2H); 3.91-3.96 (m, 2H); 3.80-3.86 (m, 1H); 3.58-3.64 (m, 1H); 3.41-3.57 (m, 3H); 3.30-3.41 (m, 2H); 3.38 (s, 3H); 1.82-1.90 (m, 2H); 1.49-1.55 (m, 2H); 1.18-1.38 (m, 26H); 0.89 (t, J=7 Hz, 3H). MS (ESI−): 598.29 [M−H]$^-$. HRMS (ESI−) calcd. for C$_{29}$H$_{53}$N$_5$O$_6$P [M−H]$^-$ 598.3739, found 598.3737 (E=−0.3 ppm). HPLC analysis: retention time 22.43 min., purity 93.0%.

Example 21

Hexadecyloxyethyl (R,S)-9-[(3-ethoxy-2-phosphonomethoxy)propyl]adenine, sodium salt (HDP-(R,S)-EPMPA) (18)

Hexadecyloxyethyl (R,S)-9-[(3-ethoxy-2-phosphonomethoxy)propyl]adenine, sodium salt (HDP-(R,S)-EPMPA) (18). Deprotection of 13 gave 18 in 92% yield. $^1$H NMR (CDCl$_3$/methanol-d$_4$), δ 8.28 (s, 1H); 8.21 (s, 1H); 4.48-4.53 (s, 1H); 4.34-4.39 (m, 1H); 3.90-4.00 (m, 3H); 3.80-3.86 (m, 1H); 3.58-3.64 (m, 1H); 3.44-3.58 (m, 6H); 3.35-3.41 (m, 2H); 1.82-1.90 (m, 2H); 1.49-1.58 (m, 2H); 1.22-1.38 (m, 26H); 1.20 (t, J=7Hz, 3H); 0.89 (t, J=7Hz, 3H). MS (ESI): 612.44 (M−H)$^-$. HRMS (ESI−) calcd. for C$_{30}$H$_{55}$N$_5$O$_6$P [M−H]$^-$ 612.3895, found 612.3898 (E=0.5 ppm). HPLC analysis: retention time 22.60 min., purity 91.8%

Example 22

Hexadecyloxyethyl (S)-9-[(3-isopropoxy-2-phosphonomethoxy)propyl]adenine, sodium salt (HDP-(R,S)-IPPMPA) (19)

Hexadecyloxyethyl (S)-9-[(3-isopropoxy-2-phosphonomethoxy)propyl]adenine, sodium salt (HDP-(R,S)-IPPMPA) (19). Deprotection of 14 gave 19 in 75% yield. $^1$H NMR (methanol-d$_4$) δ 8.35 (s, 1H, H-8), 8.25 (s, 1H, H-2), 4.53, (dd, 1H, H-1'a, J$_{1'a2'}$=3.4 Hz, J$_{gem}$=14.6 Hz), 4.39 (dd, 1H, H-1'b, J$_{1'b,2'}$=6.6 Hz, J$_{gem}$=14.6 Hz), 3.93 (t, 2H, P—O—CH$_a$, J=6.8 Hz), 3.91 (t, 1H, P—O—CH$_b$, J=6.4 Hz); 3.85 (dd, —CH$_a$—P—, J$_{P,CHa}$=9.0 Hz, J$_{gem}$=13 Hz), 3.66 (dd, 1H, —CH$_b$—P—, J$_{P,Hb}$=9.6 Hz, J$_{gem}$=13.2 Hz); 3.59-3.48 (m, 3H, H-3'+H-2'), 3.46 (t, 2H, —CH$_2$—O—CH$_2$), 3.37 (t, 2H, —CH$_2$—O—CH$_2$—), 1.80 (pentet, 2H, —O—CH$_2$CH$_2$CH$_2$—O—), 1.51 (m, 2H, —O—CH$_2$CH$_2$—(CH$_2$)$_{13}$—), 1.27 (m, 26H, —(CH$_2$)$_{13}$—), 1.13 (d, 6H, —CH(CH$_3$)$_2$), 0.89 (t, 3H, —CH$_3$); MS (ESI−): 626.69 [M−H]$^-$. HRMS (ESI−)

calcd. for $C_{31}H_{57}N_5O_6P$ [M–H]⁻ 626.4052, found 626.4053 (E=0.2 ppm). HPLC analysis: retention time 21.95 min., purity 97.1%.

Example 23

Diaminopurine Derivatives (23-26)

A scheme useful for synthesis of diaminopurine compounds described herein is provided in Scheme 2 following, with reagents and conditions as following: a) NaH, alkyl glycidyl ether, N,N-DMF, 100° C., 6H; b) sodium t-butoxide, alkoxyalkyl p-toluenesulfonyloxymethylphosphonate, N,N-DMF, 80° C.

Scheme 2. Exemplary Synthesis of Diaminopurine Derivatives (23-26)

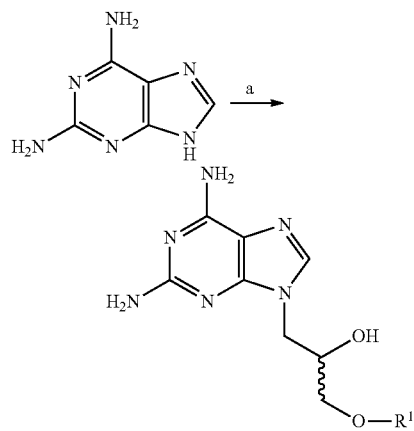

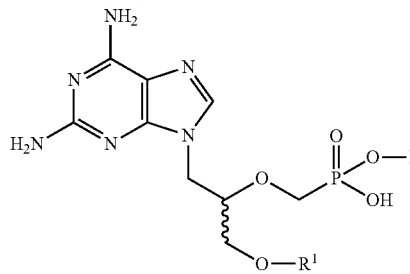

23 $R^1$ = Me (S), $R^2$ = —O(CH$_2$)$_2$O(CH$_2$)$_{17}$CH$_3$
24 $R^1$ = Me (R), $R^2$ = —O(CH$_2$)$_2$O(CH$_2$)$_{17}$CH$_3$
25 $R^1$ = Me (S), $R^2$ = —O(CH$_2$)$_3$O(CH$_2$)$_{15}$CH$_3$
26 $R^1$ = Et (R,S), $R^2$ = HDP

Example 24

(S)-9-[(3-methoxy-2-hydroxy)propyl]-2,6-diaminopurine (20)

(S)-9-[(3-methoxy-2-hydroxy)propyl]-2,6-diaminopurine (20) was synthesized from 2,6-diaminopurine (TCI America) and (S)-methyl glycidyl ether (procedure A). 27% yield (0.65 g). ¹H NMR (CDCl$_3$/methanol-d$_4$), δ 7.68 (s, 1H, H-8); 4.20-4.30 (m, 1H); 4.05-4.12 (m, 2H); 3.32-3.47 (m, 2H); 3.39 (s, 3H).

Example 25

(R)-9-[(3-methoxy-2-hydroxy)propyl]-2,6-diaminopurine (21)

(R)-9-[(3-methoxy-2-hydroxy)propyl]-2,6-diaminopurine (21) was synthesized from 2,6-diaminopurine and (R)-methyl glycidyl ether (procedure A). 41% yield. ¹H NMR (CDCl$_3$/methanol-d$_4$), δ 7.73 (s, 1H, H-8); 4.22 (d, 1H, H-1'a, $J_{gem}$=12.4 Hz), 4.06-4.02 (m, 2H, H-1'b+H-2'); 3.39 (d, 2H, J=3.2 Hz); 3.36 (s, 3H, —OCH$_3$).

Example 26

(R,S)-9-[(3-ethoxy-2-hydroxy)propyl]-2,6-diaminopurine (22)

(R,S)-9-[(3-ethoxy-2-hydroxy)propyl]-2,6-diaminopurine (22) was synthesized from 2,6-diaminopurine and (R,S)-ethyl glycidyl ether (procedure A). 71% yield. ¹H NMR (CDCl$_3$/methanol-d$_4$) δ 7.77 (s, 1H, H-8); 4.22 (dd, 1H, $J_{1'a,2'}$=3.6 Hz, $J_{gem}$=12.4 Hz, H-1'a); 4.06-4.02 (m, 2H, H-1'b+H-2'); 3.88 (q, 2H, —OCH$_2$CH$_3$); 3.39 (d, 2H, J=3.2 Hz); 1.16 (t, 3H, —OCH$_2$CH$_3$).

Example 27

Octadecyloxyethyl (S)-9-[(3-methoxy-2-phosphonomethoxy)propyl]2,6-diaminopurine, sodium salt (ODE-(S)-MPMPDAP) (23)

Octadecyloxyethyl (S)-9-[(3-methoxy-2-phosphonomethoxy)propyl]2,6-diaminopurine, sodium salt (ODE-(S)-MPMPDAP) (23) was synthesized (procedure C) from (S)-9-[(3-methoxy-2-hydroxy)propyl]2,6-diaminopurine and octadecyloxyethyl p-toluenesulfonyloxymethylphosphonate. 50% yield. ¹H NMR (CDCl$_3$/methanol-d$_4$), δ 7.72 (s, 1H); 4.00-4.20 (m, 5H); 3.80-3.90 (m, 1H); 3.58-3.65 (m, 2H); 3.50-3.58 (m, 2H); 3.40-3.50 (m, 1H); 3.44 (s, 3H); 3.30-3.38 (m, 2H); 1.50-1.60 (m, 2H); 1.18-1.38 (m, 30H); 0.88 (t, J=7 Hz, 3H). MS (ESI): 627.48 [M–H]⁻, 629.47 [M+H]⁺. HRMS (ESI–) calcd. for $C_{30}H_{56}N_6O_6P$ [M–H]⁻ 627.4004, found 627.4007 (E=0.5 ppm). HPLC analysis: retention time 23.67 min., purity 91.9%.

Example 28

Octadecyloxyethyl (R)-9-[(3-methoxy-2-phosphonomethoxy)propyl]2,6-diaminopurine, sodium salt (ODE-(R)-MPMPDAP) (24)

Octadecyloxyethyl (R)-9-[(3-methoxy-2-phosphonomethoxy)propyl]2,6-diaminopurine, sodium salt (ODE-(R)-MPMPDAP) (24) was synthesized (procedure C)from (R)-9-[(3-methoxy-2-hydroxy)propyl]2,6-diaminopurine and octadecyloxyethyl p-toluenesulfonyloxymethylphosphonate with 49% yield. ¹H NMR (CDCl$_3$/methanol-d$_4$), δ: 7.75 (s, 1H); 4.42-4.51 (m, 1H); 4.00-4.20 (m, 4H); 3.80-3.90 (m, 1H); 3.60-3.65 (m, 2H); 3.50-3.58 (m, 2H); 3.40-3.50 (m, 1H) 3.49 (s, 3H); 3.30-3.38 (m, 2H); 1.50-1.62 (m, 2H); 1.20-1.38 (m, 30H); 0.88 (t, J=7 Hz, 3H). MS (ESI+): 629.55 [M+H]⁺. HRMS (ESI–) calcd. for $C_{30}H_{56}N_6O_6P$ [M–H]⁻

627.4004, found 627.4007 (E=0.5 ppm). HPLC analysis: retention time 23.67, purity 98.4%.

Example 29

Hexadecyloxypropyl (S)-9-[3-methoxy-2-phosphonomethoxy)propyl]-2,6-diaminopurine, sodium salt (HDP-(S)-MPMPDAP) (25)

Hexadecyloxypropyl (S)-9-[3-methoxy-2-phosphonomethoxy)propyl]-2,6-diaminopurine, sodium salt (HDP-(S)-MPMPDAP) (25) was synthesized (procedure C) from (S)-9-[(3-methoxy-2-hydroxy)propyl]2,6-diaminopurine and hexadecyloxypropyl p-toluenesulfonyloxymethylphosphonate with 30% yield. $^1$H NMR (CDCl$_3$/methanol-d$_4$), δ: 7.72 (s, 1H); 4.02-4.20 (m, 3H); 3.95-4.02 (m, 2H); 3.78-3.85 (m, 2H); 3.45-3.60 (m, 3H); 3.38-3.45 (m, 6H); 1.82-1.95 (m, 2H); 1.45-1.60 (m, 2H); 1.20-1.38 (m, 26H); 0.88 (t, J=7 Hz, 3H). MS (ESI+): 615.50 [M+H]$^+$, 637.45 [M+Na]$^+$. HRMS (ESI−) calcd. for C$_{29}$H$_{54}$N$_6$O$_6$P [M−H]$^-$ 613.3848, found 613.3854 (E=1.0 ppm). HPLC analysis: retention time 22.98 min., purity 90.3%.

Example 30

Hexadecyloxypropyl (R,S)-9-[3-ethoxy-2-phosphonomethoxy)propyl-2,6-diaminopurine, sodium salt (HDP-(R,S)-EPMPDAP) (26)

Hexadecyloxypropyl (R,S)-9-[3-ethoxy-2-phosphonomethoxy)propyl-2,6-diaminopurine, sodium salt (HDP-(R,S)-EPMPDAP) (26) was synthesized (procedure C) from (R,S)-9-[(3-ethoxy-2-hydroxy)propyl]2,6-diaminopurine and hexadecyloxypropyl p-toluenesulfonyloxymethylphosphonate with 22% yield. $^1$H NMR (CDCl$_3$/methanol-d$_4$), δ: 7.40 (s, 1H); 4.44-4.52 (m, 1H); 4.18-2.28(m, 1H); 3.91-4.10 (m, 3H); 3.80-3.90 (m, 1H); 3.45-3.60 (m, 5H); 3.38-3.45 (m, 4H); 1.82-1.95 (m, 2H); 1.45-1.60 (m, 2H); 1.15-1.38 (m, 28H); 0.88 (t, J=7 Hz, 3H). MS (ESI−): 627.53 [M−H]$^-$. HRMS (ESI−) calcd. for C$_{30}$H$_{56}$N$_6$O$_6$P [M−H]$^-$ 627.4004, found 627.4008 (E=0.6 ppm). HPLC analysis: retention time 23.37 min., purity 96.4%.

Example 31

Guanine Derivatives (34-37)

A scheme useful for synthesis of guanine containing compounds described herein is provided in Scheme 3 following, with reagents and conditions as following: a) NaH, alkyl glycidyl ether, N,N-DMF, 100° C., 6 h; b) sodium t-butoxide, hexadecyloxypropyl (HDP) or octadecyloxyethyl (ODE) p-toluenesulfonyloxymethylphosphonate, N,N-DMF, 80° C.; c) 10% CF$_3$COOH/CH$_2$Cl$_2$, rt, 2 days.

Scheme 3. Exemplary Synthesis of Guanine Derivatives (34-37)

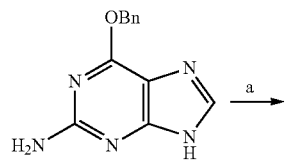

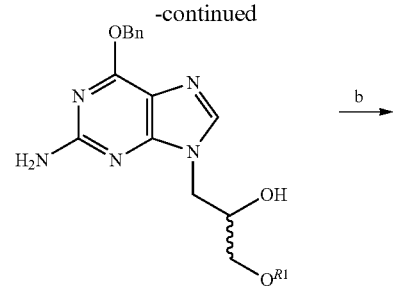

R$^1$ =
27 Me (S)
28 Me (R)
29 Et (R,S)

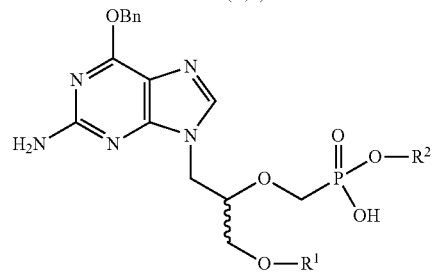

| R$^1$ = | R$^2$ = |
|---|---|
| 30 Me (S) | ODE |
| 31 Me (R) | ODE |
| 32 Me (S) | HDP |
| 33 Et (R,S) | HDP |

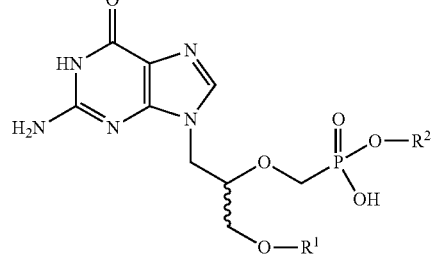

| R$^1$ = | R$^2$ = |
|---|---|
| 34 Me (S) | ODE |
| 35 Me (R) | ODE |
| 36 Me (S) | HDP |
| 37 Et (R,S) | HDP |

Example 32

(S)-9-[(3-methoxy-2-hydroxy)propyl]-6-O-benzylguanine (27)

(S)-9-[(3-methoxy-2-hydroxy)propyl]-6-O-benzylguanine (27) was synthesized from 6-O-benzylguanine (APAC Pharmaceutical LLC, Columbia, Md.) and (S)-methyl glycidyl ether (procedure A). 49% yield. $^1$H NMR (CDCl$_3$/methanol-d$_4$), δ 7.75 (s, 1H); 7.49-7.51 (m, 2H); 7.29-7.40 (m, 3H); 5.55 (s, 2H); 4.23-4.32 (m, 1H); 4.05-4.14 (m, 2H); 3.39-3.41 (m, 2H); 3.39 (s, 3H).

Example 33

(R)-9-[(3-methoxy-2-hydroxy)propyl]-6-O-benzylguanine (28)

(R)-9-[(3-methoxy-2-hydroxy)propyl]-6-O-benzylguanine (28) was synthesized from 6-O-benzylguanine and (R)- methyl glycidyl ether (procedure A). 44% yield. $^1$H NMR (CDCl$_3$/methanol-d$_4$), δ 7.74 (s, 1H); 7.47-7.51 (m, 2H); 7.29-7.40 (m, 3H); 5.55 (s, 2H); 4.40-4.60 (m, 1H); 4.05-4.14 (m, 2H); 3.32-3.45 (m, 2H); 3.39 (s, 3H).

Example 34

(R,S)-9-[(3-ethoxy-2-hydroxy)propyl]-6-O-benzylguanine (29)

(R,S)-9-[(3-ethoxy-2-hydroxy)propyl]-6-O-benzylguanine (29) was synthesized from 6-O-benzylguanine and (R,S) ethyl glycidyl ether (procedure A). 51% yield. $^1$H NMR (CDCl$_3$/methanol-d$_4$), δ 7.76 (s, 1H); 7.50-7.52 (m, 2H); 7.32-7.40 (m, 3H); 5.52 (s, 2H); 4.17-4.21 (m, 1H); 3.95-4.00 (m, 2H); 3.44-3.50 (m, 2H); 3.34-3.38 (m, 2H); 1.16 (t, J=7 Hz, 3H).

Example 35

Octadecyloxyethyl (S)-9-[(3-methoxy-2-phosphonomethoxy)propyl]-6-O-benzylguanine (30)

Octadecyloxyethyl (S)-9-[(3-methoxy-2-phosphonomethoxy)propyl]-6-O-benzylguanine (30) was synthesized (procedure C) from (S)-9-[(3-methoxy-2-hydroxy)propyl]-6-O-benzylguanine and octadecyloxyethyl p-toluenesulfonyloxymethylphosphonate. 26% yield. $^1$H NMR (CDCl$_3$/methanol-d$_4$), δ 7.93 (s, 1H); 7.50-7.56 (m, 2H); 7.31-7.40 (m, 3H); 5.55 (s, 2H); 4.24-4.36 (m, 1H); 3.93-4.22 (m, 1H); 3.75-3.98 (m, 4H); 3.60-3.70 (m, 4H); 3.30-3.60 (m, 8H); 1.42-1.60 (m, 2H); 1.18-1.38 (m, 30H); 0.89 (t, J=7 Hz, 3H). MS (ESI): 720.51 [M+H]$^+$.

Example 36

Octadecyloxyethyl (R)-9-[(3-methoxy-2-phosphonomethoxy)propyl]-6-O-benzylguanine (31)

Octadecyloxyethyl (R)-9-[(3-methoxy-2-phosphonomethoxy)propyl]-6-O-benzylguanine (31) was synthesized (procedure C) from (R)-9-[(3-methoxy-2-hydroxy)propyl]-6-O-benzylguanine and octadecyloxyethyl p-toluenesulfonyloxymethylphosphonate. 83% yield. $^1$H NMR (CDCl$_3$/methanol-d$_4$), δ 7.93 (s, 1H); 7.52-7.47 (m, 2H); 7.23-7.38 (m, 3H); 5.55 (s, 2H); 4.18-4.38 (m, 1H); 3.75-3.98 (m, 4H); 3.55-3.65 (m, 1H); 3.43-3.50 (m, 3H); 3.30-3.43 (m, 8H); 1.45-1.60 (m, 2H); 1.18-1.38 (m, 30H); 0.89 (t, J=7 Hz, 3H). MS (ESI): 718.54 [M−H]$^-$.

Example 37

Hexadecyloxypropyl (S)-9-[3-methoxy-2-phosphonomethoxy)propyl]-6-O-benzylguanine (32)

Hexadecyloxypropyl (S)-9-[3-methoxy-2-phosphonomethoxy)propyl]-6-O-benzylguanine (32) was synthesized (procedure C) from (S)-9-[(3-methoxy-2-hydroxy)propyl]-6-O-benzylguanine and hexadecyloxypropyl p-toluenesulfonyloxymethylphosphonate. 71% yield. $^1$H NMR (CDCl$_3$/methanol-d$_4$), δ:7.94 (s, 1H); 7.49-7.55 (m, 2H); 7.24-7.40 (m, 3H); 5.55 (s, 2H); 4.30-4.40 (m, 1H); 4.17-4.22 (m, 1H); 3.80-3.92 (m, 4H); 3.72-3.92 (m, 1H); 3.55-3.62 (m, 1H); 3.40-3.52 (m, 4H); 3.28-3.40 (m, 2H); 3.37 (s, 3H); 1.75-1.85 (m, 2H); 1.44-1.60 (m, 2H); 1.16-1.38 (m, 26H); 0.89 (t, J=7 Hz, 3H). MS (ESI): 706.50 [M+H]$^+$.

Example 38

Hexadecyloxypropyl (R,S)-9-[3-ethoxy-2-phosphonomethoxy)propyl]-6-O-benzylguanine (33)

Hexadecyloxypropyl (R,S)-9-[3-ethoxy-2-phosphonomethoxy)propyl]-6-O-benzylguanine (33) was synthesized (procedure C) from (R,S)-9-[(3-methoxy-2-hydroxy)propyl]-6-O-benzylguanine and hexadecyloxypropyl p-toluenesulfonyloxymethylphosphonate. 42% yield. $^1$H NMR (CDCl$_3$/methanol-d$_4$), δ 7.95 (s, 1H); 7.48-7.52 (m, 2H); 7.30-7.40 (m, 3H); 5.56 (s, 2H); 4.34-4.40 (m, 1H); 4.19-4.26 (m, 1H); 3.77-3.93 (m, 4H); 3.58-3.66 (m, 1H); 3.47-3.55 (m, 5H); 3.35-3.45 (m, 3H); 1.78-1.85 (m, 2H); 1.48-1.55 (m, 2H); 1.17-1.28 (m, 29H); 0.89 (t, J=7 Hz, 3H). MS (ESI): 718.46 [M−H]$^-$.

Example 39

General procedure E. Synthesis of Alkoxyalkyl-9-[(3-alkoxy-2-phosphonomethoxy)propyl]guanine (34-37)

The protected guanine compounds (30-33) (0.71 mmol) were added to 10% trifluoroacetic acid/CH$_2$Cl$_2$ and the mixture was stirred at room temperature for 2 days. The solvent was removed in vacuo and the residue purified by flash column chromatography on silica gel. The column was eluted with 20% MeOH/CH$_2$Cl$_2$ and the crude products were recrystallized from water to give the alkoxyalkyl 9-[(3-alkoxy-2-phosphonomethoxy)propyl]guanine derivatives (34-37).

Example 40

Octadecyloxyethyl (S)-9-[(3-methoxy-2-phosphonomethoxy)propyl]guanine (ODE-(S)-MPMPG) (34)

Octadecyloxyethyl (S)-9-[(3-methoxy-2-phosphonomethoxy)propyl]guanine (ODE-(S)-MPMPG) (34). Deprotection of 30 gave 34 as a white powder. 93% yield. $^1$H NMR (CDCl$_3$/methanol-d$_4$), 7.82 (s, 1H); 4.24-4.36 (m, 1H); 4.10-4.28 (m, 1H); 3.95-4.05 (m, 2H); 3.78-3.90 (m, 2H); 3.62-3.73 (m, 1H); 3.52-3.60 (m, 2H); 3.40-3.50 (m, 2H); 3.25-3.40 (m, 3H); 1.45-1.60 (m, 2H); 1.18-1.38 (m, 30H); 0.89 (t, J=7 Hz, 3H). MS (ESI): 628.44 [M−H]$^-$. HRMS (ESI−) calcd. for C$_{30}$H$_{55}$N$_5$O$_7$P [M−H]$^-$ 628.3845, found 628.3846 (E=0.2 ppm). HPLC analysis: retention time 21.10, purity 96.2%.

Example 41

Octadecyloxyethyl (R)-9-[(3-methoxy-2-phosphonomethoxy)propyl]guanine (ODE-(R)-MPMPG) (35)

Octadecyloxyethyl (R)-9-[(3-methoxy-2-phosphonomethoxy)propyl]guanine (ODE-(R)-MPMPG) (35). Deprotection of 31 gave 35 as a white powder. 67% yield. $^1$H NMR (CDCl$_3$/methanol-d$_4$), 8.07 (s, 1H, H-8); 7.51 (s, 2H, —NH$_2$); 4.34 (dd, 1H, H-1'a, J$_{1'a2'}$=3.9 Hz, J$_{gem}$=14.6 Hz); 4.13 (dd, 1H, H-1'b, J$_{1'b2'}$=6.4 Hz, J$_{gem}$=14.3 Hz); 4.00 (m, 2H, —P—O—CH$_2$—); 3.87 (dd, 1H, —CH$_a$—P—, J$_{P,CHa}$=8.7 Hz, J$_{gem}$=12.9 Hz); 3.68 (dd, 1H, —CH$_b$—P—, J$_{P,CHb}$=9.6 Hz, J$_{gem}$=12.8 Hz); 3.59 (t, 2H, —CH$_2$—O—CH$_2$); 3.46 (d+t, 4H, —CH$_2$—O—CH$_2$+H-3'); 3.38 (s, 3H, —OCH$_3$); 1.50-1.62 (m, 2H, —O—CH$_2$CH$_2$(CH$_2$)$_{15}$—); 1.27 (m, 30H, —(CH$_2$)$_{15}$—); 0.89 (t, J=7 Hz, 3H, —CH$_3$).

MS (ESI+): 630.29 [M+H]⁺; HRMS (ESI−) calcd. for $C_{30}H_{55}N_5O_7P$ [M−H]⁻ 628.3845, found 628.3843 (E=−0.3 ppm). HPLC analysis: retention time 22.33 min., purity 92.9%.

Example 42

Hexadecyloxypropyl (S)-9-[3-methoxy-2-phosphonomethoxy)propyl]guanine (HDP-(S)-MPMPG) (36)

Hexadecyloxypropyl (S)-9-[3-methoxy-2-phosphonomethoxy)propyl]guanine (HDP-(S)-MPMPG) (36) Deprotection of 32 gave 36 as a white powder. 93% yield. ¹H NMR (CDCl₃/methanol-d₄), 7.83 (s, 1H); 4.26-4.31 (m, 1H); 4.06-4.11 (m, 1H); 3.93-3.98 (m, 2H); 3.81-3.86 (m, 2H); 3.60-3.63 (m, 2H); 3.48-3.57 (m, 3H); 3.35-3.44 (m, 2H); 3.37 (s, 3H); 1.84-1.89 (m, 2H); 1.52-1.58 (m, 2H); 1.15-1.40 (m, 26H); 0.88 (t, J=7Hz, 3H). MS (ESI): 616.45 [M+H]⁺, 638.40 [M+Na]⁺. HRMS (ESI−) calcd. for $C_{29}H_{53}N_5O_7P$ [M−H]⁻ 614.3688, found 614.3687 (E=−0.2 ppm). HPLC analysis: retention time 20.55 min., purity 93.6%.

Example 43

Hexadecyloxypropyl (R,S)-9-[3-ethoxy-2-phosphonomethoxy)propyl]guanine (HDP-(R,S)-EPMPG) (37)

Hexadecyloxypropyl (R,S)-9-[3-ethoxy-2-phosphonomethoxy)propyl]guanine (HDP-(R,S)-EPMPG) (37). Deprotection of 33 gave 37. 88% yield. ¹H NMR (CDCl₃/methanol-d₄), 7.85 (s, 1H); 4.28-4.33 (m, 1H); 4.11-4.17 (m, 1H); 3.92-3.97 (m, 2H); 3.79-3.86 (m, 2H); 3.63-3.92 (m, 1H); 3.47-3.56 (m, 5H); 3.34-3.42 (m, 3H); 1.83-1.90 (m, 2H); 1.52-1.57 (m, 2H); 1.22-1.40 (m, 26H); 1.20 (t, J=7 Hz, 3H); 0.88 (t, J=7 Hz, 3H). MS (EI): 628.40 [M−H]⁻. HRMS (ESI−) calcd. for $C_{30}H_{55}N_5O_7P$ [M−H]⁻ 628.3845, found 628.3848 (E=0.5 ppm). HPLC analysis: retention time 20.92 min., purity 95.1%.

Example 44

Cytosine Derivative (40)

A scheme useful for synthesis of cytosine containing compounds described herein is provided in Scheme 4 following, with reagents and conditions as follows: a) NaH, (S)-methyl glycidyl ether, N,N-DMF, 100° C., 6 h; b) octadecyloxyethyl (ODE) p-toluenesulfonyloxymethylphosphonate; c) 80% aq acetic acid, 60° C., 2 h.

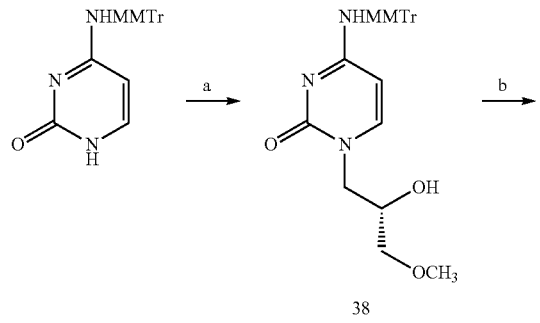

Scheme 4. Exemplary Synthesis of Cytosine Derivative (40)

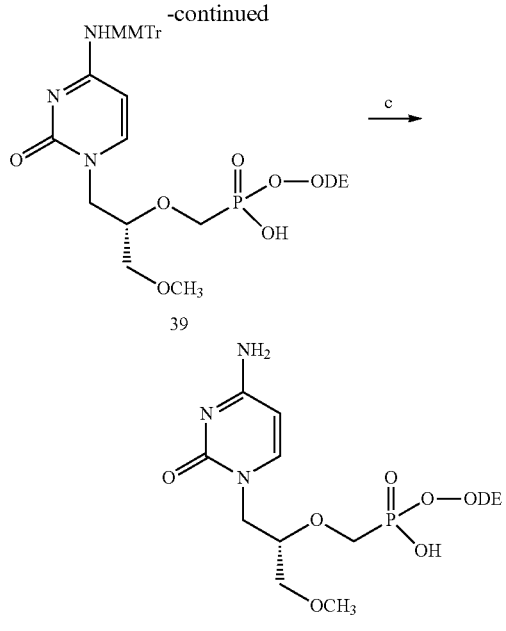

Example 45

(S)-1-[(3-methoxy-2-hydroxy)propyl]-N4-monomethoxytritylcytosine (38)

(S)-1-[(3-methoxy-2-hydroxy)propyl]-N⁴-monomethoxytritylcytosine (38) was synthesized from N⁴-monomethoxytritylcytosine⁴ and (S)-methyl glycidyl ether (procedure A). 91% yield. ¹H NMR (CDCl₃/methanol-d₄), δ 7.45-7.67 (m, 14H); 7.17 (d, J=6 Hz, 1H); 5.82 (d, J=6 Hz, 1H); 4.30-4.40 (m, 2H); 4.12 (s, 3H); 3.80-3.92 (m, 1H); 3.65-3.75 (m, 2H); 3.65 (s, 3H).

Example 46

Octadecyloxyethyl (S)-1-[(3-methoxy-2-phosphonomethoxy)propyl]-N4-monomethoxytritylcytosine (39)

Octadecyloxyethyl (S)-1-[(3-methoxy-2-phosphonomethoxy)propyl]-N⁴-monomethoxytritylcytosine (39) was synthesized from (S)-9-[(3-methoxy-2-hydroxy)propyl]-N⁴-monomethoxytritylcytosine (38) and octadecyloxyethyl p-toluenesulfonyloxymethylphosphonate (procedure C). 45% yield ¹H NMR (CDCl₃/methanol-d₄), δ 7.10-7.40 (m, 14H); 6.85 (d, J=6 Hz, 1H); 5.52 (d, J=6 Hz, 1H); 4.20-4.39 (m, 2H); 3.77-4.02 (m, 4H); 3.55-3.65 (m, 1H); 3.43-3.52 (m, 3H); 3.30-3.45 (m, 8H); 1.45-1.65 (m, 2H); 1.18-1.40 (m, 30H); 0.89 (t, J=7 Hz, 3H). MS (ESI): 860.55 [M−H]⁻.

Example 47

Octadecyloxyethyl (S)-1-[(3-methoxy-2-phosphonomethoxy)propyl]cytosine, sodium salt (40) (ODE-(S)-MPMPC)

Octadecyloxyethyl (S)-1-[(3-methoxy-2-phosphonomethoxy)propyl]cytosine, sodium salt (40) (ODE-(S)-MPMPC) Octadecyloxyethyl (S)-1-[(3-methoxy-2-phosphonomethoxy)propyl]-N⁴-monomethoxytritylcytosine (39)

(0.26 g, 0.60 mmol) was added to 80% aq acetic acid and heated to 60° C. for 2 hours. After cooling, the solvent was removed in vacuo and the residue purified by flash column chromatography on silica gel. Elution with 20% MeOH/CH$_2$Cl$_2$ gave the product (0.1 g, 55%). $^1$H NMR (CDCl$_3$/methanol-d$_4$) δ 7.80 (d, J=6 Hz, 1H); 6.00 (d, J=6 Hz, 1H); 4.04-4.15 (m, 4H); 3.55-3.68 (m, 3H); 3.42-3.53 (m, 2H); 3.35-3.42 (m, 4H); 1.50-1.65 (m, 2H); 1.18-1.38 (m, 30H); 0.88 (t, J=7 Hz, 3H). MS (ESI+): 590.33 [M+H]$^+$, 612.34 [M+Na]$^+$. HRMS (ESI−) calcd. for C$_{29}$H$_{55}$N$_3$O$_7$P [M−H]$^-$ 588.3783, found 588.3784 (E=−0.2 ppm). HPLC analysis: retention time 22.75 min., purity 90.9%.

Example 48

Methoxypurine Derivatives (43-44)

A scheme useful for synthesis of methoxypurine containing compounds described herein is provided in Scheme 5 following, with reagents and conditions as follows: a) NaH, (S)-methyl glycidyl ether, N,N-DMF, 100° C., 6 h; b) sodium t-butoxide, hexadecyloxypropyl (HDP) p-toluenesulfonyloxymethylphosphonate, N,N-DMF, 80° C.

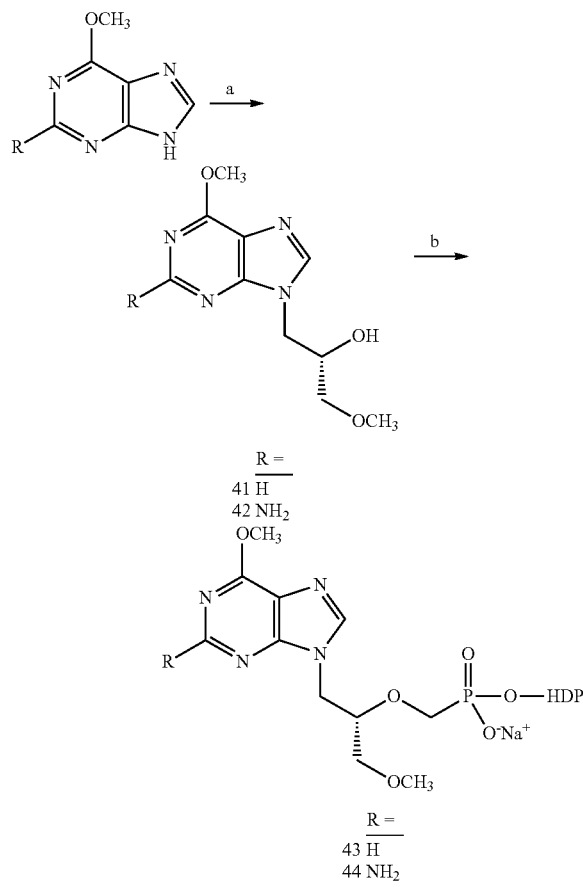

Scheme 5. Exemplary Synthesis of Methoxypurine Derivatives (43-44)

Example 49

(S)-9-[(3-methoxy-2-hydroxy)propyl]-6-methoxypurine (41)

(S)-9-[(3-methoxy-2-hydroxy)propyl]-6-methoxypurine (41) Reaction of 6-methoxypurine (TCI America, Portland, Oreg.) with (S)-methyl glycidyl ether according to procedure A gave compound 41. 67% yield. $^1$H NMR (methanol-d$_4$) δ 8.51 (s, 1H, H-8), 8.24 (s, 1H, H-2), 4.74 (dd, 1H, J$_{1'a2}$=3.8 Hz, J$_{gem}$=14.2 Hz), 4.28 (dd, 1H, J$_{1'b2}$=8 Hz, J$_{gem}$=14.2 Hz), 4.18 (s, 3H, Ar—OCH$_3$), 4.14 (m, 1H, H-2'), 3.42 (d, 2H, J$_{3'2'}$=5.2 Hz), 3.37 (s, 3H, —CH$_2$—OCH$_3$).

Example 50

(S)-9-[(3-methoxy-2-hydroxy)propyl]-6-O-methylguanine (42)

(S)-9-[(3-methoxy-2-hydroxy)propyl]-6-O-methylguanine (42) Reaction of 6-O-methylguanine (Aldrich Chem.) with (S)-methylglycidyl ether (Procedure A) gave compound 42. 78% yield. $^1$H NMR (methanol-d$_4$) δ 7.81 (s, 1H, H-8); 4.35 (dd, 2H, H-1'); 4.15 (m, 1H, H-2'); 4.05 (s, 3H, Ar—OCH$_3$); 3.39 (d, 2H, H-3'); 3.35 (s, 3H, —OCH$_3$). MS (ESI): m/z 254.08 [M+H]$^+$.

Example 51

Hexadecyloxypropyl (S)-9-[(3-methoxy-2-phosphonomethoxy)propyl]-6-methoxypurine (HDP-(S)-MPMPMP) (43)

Hexadecyloxypropyl (S)-9-[(3-methoxy-2-phosphonomethoxy)propyl]-6-methoxypurine (HDP-(S)-MPMPMP) (43) Reaction of compound 41 with hexadecyloxypropyl p-toluenesulfonyloxymethylphosphonate according to procedure C afforded compound 43. 29% yield. $^1$H NMR (methanol-d$_4$) δ 8.51 (s, 1H, H-8); 8.44 (s, 1H, H-2); 4.56 (dd, 1H, H-1'$_a$, J$_{1'a,2'}$=3.6 Hz, J$_{gem}$=14.0 Hz); 4.44 (dd, 1H, H-1'$_b$, J$_{1'b,2'}$=6.6 Hz, J$_{gem}$=14.6 Hz); 4.17 (s, 3H, Ar—OCH$_3$); 3.96 (m, 1H, H-2'); 3.86 (t, 1H, P—O—CH$_a$, J=6.4 Hz); 3.84 (t, 1H, P—O—CH$_b$, J=6.4 Hz); 3.78 (dd, 1H, —CH$_a$—P—, J$_{P,CH}$=9.2 Hz, J$_{gem}$=12.8 Hz); 3.60 (dd, 1H, —CH$_b$—P—, J$_{P,CH}$=9.6 Hz, J$_{gem}$=12.8 Hz); 3.44 (m, 1H, H-2'); 3.43 (t, 2H, —CH$_2$—O—CH$_2$—); 3.36 (t, 2H, —CH$_2$—O—CH2-); 3.32 (s, 3H, —OCH$_3$); 1.76 (pentet, 2H, —O—CH$_2$CH$_2$CH$_2$—O—); 1.49 (m, 2H, —CH$_2$—O—CH$_2$CH$_2$(CH$_2$)$_{13}$—); 1.28 (m, 26H, —(CH$_2$)$_{13}$—); 0.89 (t, 3H, —CH$_3$). MS (ESI−) m/z 613.46 [M−H]$^-$. HRMS (ESI−) calcd. for C$_{30}$H$_{54}$N$_4$O$_7$P [M−H]$^-$ 613.3736, found 613.3739 (E=0.5 ppm).

Example 52

Hexadecyloxypropyl (S)-9-[(3-methoxy-2-phosphonomethoxy)propyl]-6-O-methylguanine (HDP-(S)-MPMPOMG) (44)

Hexadecyloxypropyl (S)-9-[(3-methoxy-2-phosphonomethoxy)propyl]-6-O-methylguanine (HDP-(S)-MPMPOMG) (44). Reaction of compound 42 with hexadecyloxypropyl p-toluenesulfonyloxymethylphosphonate according to procedure C afforded compound 44. 34% yield. $^1$H NMR (methanol-d$_4$) δ 7.95 (s, 1H, H-8), 4.34 (dd, 1H, H-1'a, J$_{1'a2'}$=4 Hz, J$_{gem}$=14.4 Hz); 4.22 (dd, 1H, H-1'b, J$_{1'b2'}$=6.4 Hz, J$_{gem}$=14.4 Hz); 4.04 (s, 3H, Ar—OCH$_3$); 3.91 (m, 1H, H-2'); 3.87 (t, 1H, P—O—CH$_a$—, J=6.4 Hz); 3.86 (t, 1H, P—O—CH$_b$—, J=6.4 Hz); 3.75 (dd, 1H, —CH$_a$—P—, J$_{CH,P}$=9.4 Hz, J$_{gem}$=13 Hz); 3.64 (dd, 1H, —CH$_b$—P—, J$_{CH,P}$=9.2 Hz, J$_{gem}$=12.8 Hz); 3.44 (t, 2H, —CH$_2$—O—); 3.43 (d, 2H, H-3'); 3.35 (t, 2H, —O—CH$_2$); 3.34 (s, 3H, —OCH$_3$); 1.78 (pentet, 2H, —O—CH$_2$CH$_2$CH$_2$—O—); 1.50 (m, 2H, —OCH$_2$CH$_2$(CH$_2$)$_{13}$—); 1.27 (m, 26H, (CH$_2$)$_{13}$); 0.89 (t, 3H, —CH$_3$). MS (ESI) m/z 630.35 [M+H]$^+$; 628.37 [M−H]$^-$. HRMS (ESI−)

calcd. for $C_{30}H_{55}N_5O_7P$ [M−H]⁻ 628.3845, found 628.3847 (E=0.3 ppm). HPLC analysis: retention time 21.60 min., purity 97.0%.

Example 53

Hexadecyloxypropyl (R,S)-9-[(3-fluoro-2-phosphonomethoxy)propyl]adenine (HDP-(R,S)-FPMPA)

Sodium hydride (0.10 g, 4.37 mmol) was added to a solution of adenine (1.78 g, 13.1 mmol) in anhydrous N,N-DMF (60 mL), then (R,S)-epifluorohydrin (1.0 g, 13.1 mmol) was added to the mixture that was stirred and heated to 100° C. for 6 hours. After cooling, the solvent was removed in vacuo and the residue was purified by flash column chromatography on silica gel. Elution of the column with 10% MeOH/CH₂Cl₂ gave (R,S)-9-[(3-fluoro-2-hydroxy)propyl]adenine in 56% yield (1.58 g). ¹H NMR (CDCl₃/methanol-d₄), δ: 8.25 (s, 1H); 8.06 (s, 1H); 4.35-4.55 (m, 3H); 4.15-4-30 (m, 2H).

Bromotrimethylsilane (2.10 mL, 16.60 mmol) was added dropwise to a suspension of (R,S)-9-[(3-fluoro-2-hydroxy)propyl]adenine (1.56 g, 7.38 mmol) in dry pyridine (30 mL). The mixture was stirred 15 min until it became clear, then monomethoxytrityl chloride (2.60 g, 8.4 mmol) and 4-(dimethylamino)-pyridine (0.06 g, 0.50 mmol) were added and stirring was continued overnight. The mixture was cooled with an ice bath and H₂O (1 mL) was added. Stirring was continued 10 min., then con. NH₄OH (1 mL) was added and the reaction was stirred 30 additional min. The mixture was allowed to warm up to room temperature and filtered through a pad of Celite®. The filtrate was evaporated in vacuo and the residue was purified by flash column chromatography on silica gel. Gradient elution 100% hexanes to 100% ethyl acetate afforded N⁶-monomethoxytrityl (R,S)-9-[(3-fluoro-2-hydroxy)propyl]adenine (2.15 g, 60% yield) ¹H NMR (CDCl₃/methanol-d₄), δ: 7.99 (s, 1H); 7.98 (s, 1H); 7.15-7.37 (m, 12H); 6.75-6.83(m, 2H); 4.40-4.54 (m, 2H); 4.19-4.25 (m, 3H); 3.79 (s, 3H).

Sodium t-butoxide (0.20 g, 2.0 mmol) was added to a solution of N⁶-monomethoxytrityl (R,S)-9-[(3-fluoro-2-hydroxy)propyl]adenine (0.48 g, 1.0 mmol) and hexadecyloxypropyl p-toluenesulfonyloxymethylphosphonate (0.82 g, 1.5 mmol, prepared as described by Beadle, et al., 2006, Id.) in N,N-DMF (20 mL). in N,N-DMF (100 mL). The mixture was heated to 80° C. and kept overnight. After cooling, the solvents were evaporated in vacuo and the residue was purified by flash column chromatography on silica gel. The column was eluted with gradient chloroform 100%—chloroform-methanol (20%) to give hexadecyloxypropyl (R,S)-9-[(3-fluoro-2-phosphonomethoxy)propyl]N⁶-monomethoxytrityl adenine (0.26 g, 30% yield). ¹H NMR (CDCl₃/methanol-d₄), δ: 8.18 (s, 1H); 7.98 (s, 1H); 7.18-7.38 (m, 12H); 6.79-6.81 (m, 2H); 4.40-4.68 (m, 3H); 4.22-4.40 (m, 2H); 3.85-4.05 (m, 2H); 3.79 (s, 3H); 3.58-3.65 (m, 2H); 3.21-3.25 (m, 2H); 3.15-3.19 (m, 2H); 1.79-1.87 (m, 2H); 1.43-1.59 (m, 2H); 1.20-1.38 (m, 26H); 0.88 (t, J=7 Hz, 3H). MS (EI): 858.59 (M−H)⁻.

The product (0.26 g, 0.30 mmol) was added to 80% acetic acid and heated to 60° C. overnight. After cooling, the solvent was removed in vacuo and the residue purified by flash column chromatography on silica gel. Elution with 20% MeOH/CH₂Cl₂ gave hexadecyloxypropyl (R,S)-9-[(3-fluoro-2-phosphonomethoxy)propyl]adenine (0.15 g, 88% yield). ¹H NMR (CDCl₃/methanol-d₄), δ: 8.30 (s, 1H); 8.25 (s, 1H); 4.45-4.68 (m, 3H); 4.35-4.42 (m, 2H); 3.78-4.08 (m, 4H); 3.43-3.55 (m, 2H); 3.17-3.23 (m, 2H); 1.81-1.87 (m, 2H); 1.43-1.62 (m, 2H); 1.18-1.40 (m, 26H); 0.89 (t, J=7 Hz, 3H). MS (EI): 586.35 (M−H)⁻.

Example 54

Octadecyloxyethyl (S)-9-[(3-fluoro-2-phosphonomethoxy)propyl]adenine (ODE-(S)-FPMPA)

Sodium hydride (0.08 g, 2.0 mmol) was added to a solution of adenine (1.35 g, 10 mmol) in anhydrous N,N-DMF (60 mL), then (5)-trityl glycidyl ether (3.16 g, 10 mmol) was added to the mixture that was stirred and heated to 100° C. for 6 hours. After cooling, the solvent was removed in vacuo and the residue was purified by flash column chromatography on silica gel. Elution of the column with 10% MeOH/CH₂Cl₂ gave 9-[(3-trityloxy-2-hydroxy)propyl]adenine in 75% yield (3.4 g). ¹H NMR (CDCl₃/methanol-d₄), δ: 8.20 (s, 1H); 7.90 (s, 1H); 7.42-7.54 (m, 6H); 7.24-7.32 (m, 9H); 4.43-4.64 (m, 1H); 4.29-4-33 (m, 1H); 4.15-4.18 (m, 1H); 3.19-3.35 (m, 1H); 3.09-3.13 (m, 1H).

Bromotrimethylsilane (1.90 mL, 14.65 mmol) was added dropwise to a suspension of (S)-9-[(3-trityloxy-2-hydroxy)propyl]adenine (2.94 g, 6.5 mmol) in dry pyridine (30 mL). The mixture was stirred 15 min. until it became clear, then monomethoxytrityl chloride (2.30 g, 7.4 mmol) and 4-(dimethylamino)-pyridine (0.05 g, 0.46 mmol) were added and stirring was continued overnight. The mixture was cooled with an ice bath and H₂O (1 mL) was added. Stirring was continued 10 min., then con. NH₄OH (1 mL) was added and the reaction was stirred 30 additional min. The mixture was allowed to warm up to room temperature and filtered through a pad of Celite®. The filtrate was evaporated in vacuo and the residue was purified by flash column chromatography on silica gel. Gradient elution 100% hexanes to 100% ethyl acetate afforded (S)-9-[(3-trityloxy-2-hydroxy)propyl]N⁶-monomethoxytrityl-adenine (4.37 g, 93% yield) ¹H NMR (CDCl₃/methanol-d₄), δ: 8.14 (s, 1H); 7.99 (s, 1H); 7.44-7.61 (m, 27H); 6.99-7.03(m, 2H); 4.52-4.69 (m, 1H); 4.40-4.52 (m, 1H); 4.25-4.40 (m, 1H); 3.99 (s, 3H); 3.35-3.45 (m, 1H); 3.25-3.35 (m, 1H).

Sodium t-butoxide (0.96 g, 10.0 mmol) was added to a solution of (S)-9-[(3-trityloxy-2-hydroxy)propyl]N⁶-monomethoxytrityl-adenine (3.6 g, 5.0 mmol) and diethyl p-toluenesulfonyloxymethylphosphonate (3.2 g, 10.0 mmol,) in N,N-DMF (100 mL). The mixture was heated to 80° C. and kept overnight. After cooling, the solvents were evaporated in vacuo and the residue was purified by flash column chromatography on silica gel. The column was eluted with gradient chloroform 100%—chloroform-methanol (20%) to give diethyl (S)-9-[(3-trityloxy-2-phosphonomethoxy)propyl] N⁶-monomethoxytrityl-adenine (2.53 g, 57% yield). ¹H NMR (CDCl₃/methanol-d₄), δ: 7.94 (s, 1H); 7.92 (s, 1H); 7.41-7.50 (m, 7H); 7.21-7.35(m, 20H); 6.79-6.81 (m, 2H); 4.37-4.51 (m, 2H); 3.89-4.12 (m, 6H); 3.79 (s, 3H); 3.34-3.38 (m, 2H); 3.15-3.19 (m, 1H); 1.29 (t, J=7 Hz, 3H); 1.23 (t, J=7 Hz, 3H).

The product (2.52 g, 2.88 mmol) was added to 80% acetic acid and heated to 60° C. overnight. After cooling, the solvent was removed in vacuo and the residue purified by flash column chromatography on silica gel. Elution with 20% MeOH/CH₂Cl₂ gave diethyl (S)-9-[3-hydroxy-2-phosphonomethoxy)propyl]adenine (0.84 mg, 82% yield). ¹H NMR (CDCl₃/methanol-d₄), δ: 8.26 (s, 1H); 8.04 (s, 1H); 4.37-4.50 (m, 2H); 4.05-4.11 (m, 4H); 3.88-4.00 (m, 1H); 3.75-3.84 (m, 2H); 3.59-3.70 (m, 2H); 1.33 (t, J=7 Hz, 3H); 1.29 (t, J=7 Hz, 3H). MS (EI): 360.35 (M+H)⁺, 382.32 (M+Na)⁺.

Diethyl (S)-9-[3-hydroxy-2-phosphonomethoxy)propyl] adenine (0.45 g, 1.25 mmol) was dissolved in dry pyridine (10 mL) and treated with methanesulfonyl chloride (0.12 mL, 1.50 mmol). After 1 hour. An additional equivalent of methanesulfonyl chloride was added, followed an hour later by a third equivalent. The pyridine was evaporated. The residue was purified by column chromatography on silica gel. Eluent: ethyl acetate 100%, ethyl acetate (80%)—10% ammonium hydroxide in ethanol—20%. The yield was 0.40 g (89%). $^1$H NMR (CDCl$_3$/methanol-d$_4$), δ: 8.26 (s, 1H); 8.08 (s, 1H); 4.48-4.56 (m, 2H); 4.37-4.44 (m, 1H); 4.25-4.30 (m, 1H); 3.99-4.18 (m, 6H); 3.76-3.83 (m, 1H); 3.16 (s, 3H); 1.33 (t, J=7 Hz, 3H); 1.28 (t, J=7 Hz, 3H). MS (EI): 438.26 (M+H)$^+$, 460.03 (M+Na)$^+$.

Obtained methansulfonate (0.40 g, 0.91 mmol) was suspended in the mixture acetonitrile-toluene 1:1 (30 mL) and treated with tetramethylammonium bifluoride (0.26 g, 2.73 mmol) and heated at about 100° C. for 1 hour. The solvent were evaporated. The residue was purified by column chromatography on silica gel. Eluent: ethyl acetate 100%, ethyl acetate (80%)—10% ammonium hydroxide in ethanol— 20%. The yield was 0.33 g (100%). $^1$H NMR (CDCl$_3$/methanol-d$_4$), δ: 8.26 (s, 1H); 8.06 (s, 1H); 4.37-4.77 (m, 4H); 3.99-4.17 (m, 6H); 3.76-3.83 (m, 1H); 1.32 (t, J=7 Hz, 3H); 1.28 (t, J=7 Hz, 3H). MS (EI): 362.06 (M+H)$^+$.

Diethyl (S)-9-[(3-fluoro-2-phosphonomethoxy)propyl] adenine (0.33 g, 0.91 mmol) was dissolved in dry N,N-DMF (5 ml), and bromotrimethylsilane (0.26 mL, 1.90 mmol) was added to the solution. The mixture was stirred at room temperature overnight. The solvents were evaporated and coevaporated with toluene (20 mL). Methanol-water 1:1 (20 mL) were added to the residue. The mixture was stirred at room temperature for 30 min, the solvents were evaporated; the residue was purified by ion-exchange chromatography on DEAE Sephadex A-25 (HCOO$^-$ form). Eluent: gradient water –1M formic acid. The yield was 0.18 g (65%). $^1$H NMR (D$_2$O/methanol-d$_4$), δ: 8.45 (s, 1H); 8.38 (s, 1H); 4.40-4.74 (m, 4H); 4.04-4.19 (m, 1H); 3.78-3.83 (m, 1H); 3.62-3.72 (m, 1H). MS (EI): 304.00 (M+H)$^+$.

To the solution of (S)-9-[(3-fluoro-2-phosphonomethoxy) propyl]adenine (0.09 g, 0.29 mmol) and octadecyloxyethanol (0.11 g, 0.35 mmol) in dry pyridine (20 mL) N,N-dicyclohexylcarbodiimide (0.14 g, 0.70 mmol) was added. The mixture was stirred at 80° C. for 5 hours. The solvents were evaporated and then the residue was purified by column chromatography on silica gel. Elution with 20% MeOH/CH$_2$Cl$_2$ gave octadecyloxyethyl (S)-9-[3-fluoro-2-phosphonomethoxy)propyl]adenine (0.04 g, 23% yield). $^1$H NMR (CDCl$_3$/methanol-d$_4$), δ: 8.31 (s, 1H); 8.18 (s, 1H); 4.50-4.75 (m, 2H); 4.43-4.49 (m, 1H); 4.07-4.16 (m, 1H); 3.98-4.17 (m, 2H); 3.84-3.72 (m, 1H); 3.56-3.60 (m, 2H); 3.42-3.48 (m, 2H); 3.35-3.37 (m, 1H); 1.52-1.60 (m, 2H); 1.20-1.34 (m, 30H); 0.88 (t, J=7 Hz, 3H). MS (EI): 600.30 (M–H)$^-$.

Example 55

Octadecyloxyethyl (R)-9-[(3-fluoro-2-phosphonomethoxy)propyl]adenine (ODE-(R)-FPMPA)

Sodium hydride (0.16 g, 4.0 mmol) was added to a solution of adenine (2.70 g, 20 mmol) in anhydrous N,N-DMF (60 mL), then (R)-trityl glycidyl ether (6.18 g, 19.5 mmol) was added to the mixture that was stirred and heated to 100° C. for 6 hours. After cooling, the solvent was removed in vacuo and the residue was purified by flash column chromatography on silica gel. Elution of the column with 10% MeOH/CH$_2$Cl$_2$ gave (R) 9-[(3-trityloxy-2-hydroxy)propyl]adenine in 82% yield (7.2 g). $^1$H NMR (CDCl$_3$/methanol-d$_4$), δ: 8.20 (s, 1H); 7.91 (s, 1H); 7.42-7.56 (m, 6H); 7.22-7.32 (m, 9H); 4.48-4.50 (m, 1H); 4.50-4.63 (m, 1H); 4.15-4.18 (m, 1H); 3.20-3.25 (m, 1H); 3.09-3.13 (m, 1H).

Bromotrimethylsilane (4.50 mL, 35.0 mmol) was added dropwise to a suspension of (R) 9-[(3-trityloxy-2-hydroxy) propyl]adenine (7.20 g, 15.95 mmol) in dry pyridine (60 mL). The mixture was stirred 15 min. until it became clear, then monomethoxytrityl chloride (5.60 g, 18.0 mmol) and 4-(dimethylamino)-pyridine (0.13 g, 1.1 mmol) were added and stirring was continued overnight. The mixture was cooled with an ice bath and H$_2$O (1 mL) was added. Stirring was continued 10 min., then con. NH$_4$OH (1 mL) was added and the reaction was stirred 30 additional min. The mixture was allowed to warm up to room temperature and filtered through a pad of Celite®. The filtrate was evaporated in vacuo and the residue was purified by flash column chromatography on silica gel. Gradient elution 100% hexanes to 100% ethyl acetate afforded (R) 9-[(3-trityloxy-2-hydroxy)propyl]N$^6$-monomethoxytrityl adenine (5.97 g, 52% yield) $^1$H NMR (CDCl$_3$/methanol-d$_4$), δ: 7.93 (s, 1H); 7.83 (s, 1H); 7.41-7.47 (m, 5H); 7.20-7.03(m, 20H); 6.79-6.82 (m, 2H); 4.37-4.41 (m, 1H); 4.23-4.29 (m, 1H); 4.10-4.17 (m, 1H); 3.79 (s, 3H); 3.18-3.21 (m, 1H); 3.10-3.13 (m, 1H).

Sodium t-butoxide (1.05 g, 11.0 mmol) was added to a solution of (R)-9-[(3-trityloxy-2-hydroxy)propyl]N$^6$-monomethoxytrityl-adenine (5.45 g, 7.23 mmol) and diethyl p-toluenesulfonyloxymethylphosphonate (4.80 g, 15.0 mmol,) in N,N-DMF (100 mL). The mixture was heated to 80° C. and kept overnight. After cooling, the solvents were evaporated in vacuo and the residue was purified by flash column chromatography on silica gel. The column was eluted with gradient chloroform 100%—chloroform-methanol (20%) to give diethyl (R)—N$^6$-monomethoxytrityl-9-[3-tityloxy-2-phosphonomethoxy)propyl]adenine (6.28 g, 99% yield). $^1$H NMR (CDCl$_3$/methanol-d$_4$), δ: 7.95 (s, 1H); 7.92 (s, 1H); 7.41-7.48 (m, 7H); 7.21-7.35(m, 20H); 6.79-6.81 (m, 2H); 4.37-4.49 (m, 2H); 3.83-4.25 (m, 6H); 3.78 (s, 3H); 3.36-3.40 (m, 2H); 3.15-3.20 (m, 1H); 1.28 (t, J=7 Hz, 3H); 1.23 (t, J=7 Hz, 3H).

The product (6.30 g, 7.23 mmol) was added to 80% acetic acid and heated to 60° C. overnight. After cooling, the solvent was removed in vacuo and the residue purified by flash column chromatography on silica gel. Elution with 20% MeOH/ CH$_2$Cl$_2$ gave diethyl (R)-9-[3-hydroxy-2-phosphonomethoxy)propyl]adenine (1.85 g, 71% yield). $^1$H NMR (CDCl$_3$/methanol-d$_4$), δ: 8.25 (s, 1H); 8.08 (s, 1H); 4.42-4.50 (m, 1H); 4.36-4.40(m, 1H); 3.95-4.15 (m, 5H); 3.78-3.90 (m, 2H); 3.60-3.77 (m, 2H); 1.31 (t, J=7 Hz, 3H); 1.27 (t, J=7 Hz, 3H).

Diethyl (R)-9-[3-hydroxy-2-phosphonomethoxy)propyl] adenine (1.83 g, 5.10 mmol) was dissolved in dry pyridine (50mL) and treated with methanesulfonyl chloride (0.47 mL, 6.10 mmol). After 1 hour. An additional equivalent of methanesulfonyl chloride was added, followed an hour later by a third equivalent. The pyridine was evaporated. The residue was purified by column chromatography on silica gel. Eluent: ethyl acetate 100%, ethyl acetate (80%)—10% ammonium hydroxide in ethanol—20%. The yield was 1.94 g (88%). $^1$H NMR (CDCl$_3$/methanol-d$_4$), δ: 8.26 (s, 1H); 8.08 (s, 1H); 4.48-4.56 (m, 2H); 4.37-4.44 (m, 1H); 4.25-4.32 (m, 1H); 4.00-4.18 (m, 6H); 3.78-3.82 (m, 1H); 3.16 (s, 3H); 1.32 (t, J=7 Hz, 3H); 1.28 (t, J=7 Hz, 3H).

Obtained methansulfonate (0.44 g, 1.00 mmol) was suspended in the mixture acetonitrile-toluene 1:1 (30 mL) and treated with tetramethylammonium bifluoride (0.28 g, 2.80 mmol) and heated at about 100° C. for 1 hour. The solvents were evaporated. The residue was purified by column chromatography on silica gel. Eluent: ethyl acetate 100%, ethyl acetate (80%)—10% ammonium hydroxide in ethanol –20%. The yield was 0.36 g (100%). $^1$H NMR (CDCl$_3$/methanol-d$_4$), δ: 8.26 (s, 1H); 8.07 (s, 1H); 4.37-4.80 (m, 4H); 4.00-4.17 (m, 6H); 3.76-3.83 (m, 1H); 1.32 (t, J=7 Hz, 3H); 1.28 (t, J=7 Hz, 3H). MS (EI): 362.05 (M+H)$^+$; 383.96 (M+Na)$^+$.

Diethyl (R)-9-[(3-fluoro-2-phosphonomethoxy)propyl]adenine (0.36 g, 1.00 mmol) was dissolved in dry N,N-DMF (5 ml), and bromotrimethylsilane (0.40 mL, 3.00 mmol) was added to the solution. The mixture was stirred at room temperature overnight. The solvents were evaporated and coevaporated with toluene (20 mL). Methanol-water 1:1 (20 mL) were added to the residue. The mixture was stirred at room temperature for 30 min, the solvents were evaporated; the residue was purified by ion-exchange chromatography on DEAE Sephadex A-25 (HCOO$^-$ form). Eluent: gradient water –1M formic acid. The yield was 0.18 mg (60%). $^1$H NMR (D$_2$O), δ: 8.33 (s, 1H); 8.23 (s, 1H); 4.65-4.74 (m, 1H); 4.38-4.60 (m, 3H); 4.05-4.15 (m, 1H); 3.50-3.65 (m, 2H). MS (EI): 303.99 (M+H)$^+$.

To the solution of (R)-9-[(3-fluoro-2-phosphonomethoxy)propyl]adenine (0.09 g, 0.29 mmol) and octadecyloxyethanol (0.11 g, 0.35 mmol) in dry pyridine (20 mL) N,N-dicylcohexylcarbodiimide (0.14 g, 0.70 mmol) was added. The mixture was stirred at 50° C. for 2 hours. The solvents were evaporated and the residue was purified by column chromatography on silica gel. Elution with 20% MeOH/CH$_2$Cl$_2$ gave octadecyloxyethyl (R)-9-[3-hydroxy-2-phosphonomethoxy)propyl]adenine (0.11 g, 65% yield). $^1$H NMR (CDCl$_3$/methanol-d4), δ: 8.31 (s, 1H); 8.22 (s, 1H); 4.44-4.77 (m, 2H); 4.34-4.42 (m, 1H); 3.97-4.16 (m, 1H); 3.98-4.17 (m, 2H); 3.84-3.72 (m, 1H); 3.56-3.60 (m, 2H); 3.42-3.48 (m, 2H); 3.35-3.37 (m, 1H); 1.50-1.60 (m, 2H); 1.20-1.38 (m, 30H); 0.88 (t, J=7 Hz, 3H). MS (EI): 600.29 (M–H)$^-$.

Example 56

Synthesis of (S)-MPMPA diphosphate

To a stirred suspension of 9-(S)-[3-methoxy-2-(phosphonomethoxy)propyl]adenine ((S)-MPMPA, 770 mg, 2.4 mmol) in pyridine-H$_2$O (10;1, 10 mL) was added tri-n-butylamine (926 mg, 5 mmol). The solution was stirred at room temp 10 min until a clear solution was obtained, then the solvents were evaporated under vacuum. The residue was dissolved in hexamethylphosphoramide (HMPA, 10 mL) and to this was added 1,1'-carbonyldiimidazole (810 mg, 5 mmol) and the solution was stirred for 1 h at 22° C. Methanol was added (270 μL) and after stirring additional 0.5 h a solution of bis(tri-n-butylammonium) pyrophosphate (1.1 g, 3 mmol) in HMPA (6 mL) was added and the mixture stirred for 18 h. The precipitated inorganic pyrophosphate was removed by filtration and washed with a small volume of HMPA. The HMPA solutions were combined, diluted with cold water (25 mL) and chromatographed on a column of DEAE cellulose (HCO$_3$— form) using a linear gradient of triethylammonium hydrogen carbonate (0-0.4 M). UV active fractions containing MPMPA diphosphate were combined and lyophilized to give (S)-MPMPA diphosphate triethylammonium salt as a white powder (1.2 g, 72% yield).

Example 57

Antiviral Activity

Determination of the 50% Effective Concentration (EC$_{50}$) in HCV Genotype 1b and 2a Replicons.

Compounds of the invention were tested for anti-HCV activity as previously described using 10,000 replicon cells per well on 96-well plates. See Wyles, D. L. et al., 2009, Antimicrob. Agents Chemother. 53:2660-2662. Values for 50% effective concentration (EC$_{50}$) and for the minimal concentration required to induce 50% cleavage (CC$_{50}$) were calculated for each test compound by linear regression analysis, using data combined for all treated cultures. Antiviral and toxicity assays utilized triplicate cultures for each drug concentration; 12 untreated cultures were included in each assay.

Example 58

Anti-HCV Activity

Compounds were tested for anti-HCV activity in genotype 1b and 2a replicons as previously described, and their activity was compared with that of ODE-(S)-HPMPA and HDP-(S)-HPMPA (Table 5 following). See Wyles, D. L., et al., 2007, J Virol, 81:3005-3008. ODE-(S)-MPMPA (15) retained full activity against genotype 1b and 2a replicons with EC$_{50}$ values of 1.43±0.38 and 2.38±1.09 μM while the (R) isomer (16) was slightly less active with EC$_{50}$s of 4.65 and 5.33 μM. HDP-(S)-MPMPA (17) was slightly less active than the corresponding ODE ester with EC$_{50}$s of 2.36 (1b) and 4.64 μM (2a). When ethyl or isopropyl substitutions were made at the 3'-hydroxyl instead of methyl, the anti-HCV activity dropped slightly with HDP-(R,S)-EPMPA (18) to EC$_{50}$s of 7.59 (1b) and 8.87 μM (2a). Without wishing to be bound by any theory, these data suggest that larger substitutions are not favored. Cytotoxicity of ODE-(S)-MPMPA was substantially lower than that observed with ODE-(S)-HPMPA, CC$_{50}$>150 versus 35.6 μM. Of the various adenine analogs, ODE-(S)-MPMPA had the greatest selectivity index, >105 with genotype 1b and >63 with genotype 2a replicons. The BM4-5 and JFH-1 replicons have been described. See e.g., Wyles, D. L., et al., 2007, Id.; Date, T., et al., 2004, J. Biol. Chem., 279:22371-22376.

TABLE 5

| | EC$_{50}$ (μM) | | CC$_{50}$ | Selectivity Index BM4-5 | Selectivity Index JFH-1 |
|---|---|---|---|---|---|
| Cmpd | BM4-5(1b) | JFH-1 (2a) | (μM) | (1b) | (2a) |
| 1 | 1.55 ± 0.50 | 1.65 ± 0.33 | 35.6 ± 6.8 | 22.9 | 21.6 |
| 15 | 1.43 ± 0.38 | 2.38 ± 1.09 | >150 | >105 | >63 |
| 16 | 4.65 ± 0.88 | 5.33 ± 0.92 | >150 | >32.3 | >28.1 |
| 17 | 2.36 ± 0.37 | 4.64 ± 1.26 | >150 | >63.6 | >32.3 |
| 18 | 7.59 ± 1.31 | 8.87 ± 2.05 | 99 ± 0.5 | 13.0 | 11.1 |
| 19 | 51.2 ± 38.2 | 98.8 ± 20.8 | 100 ± 20.8 | 3.14 | NM |
| 23 | 20.1 ± 1.98 | 21.4 ± 1.30 | 99.0 ± 13.4 | 4.94 | 4.62 |
| 24 | 25.6 ± 4.23 | 25.8 ± 6.10 | >150 | >5.86 | >5.81 |
| 25 | 21.3 ± 3.10 | 23.6 ± 2.70 | 91.5 ± 17.8 | 4.30 | 3.87 |
| 26 | 18.2 ± 7.09 | 19.5 ± 1.48 | >150 | >8.2 | >7.69 |
| 34 | 8.26 ± 1.30 | 10.7 ± 1.33 | >150 | >18.2 | >14.0 |
| 35 | 12.6 ± 1.67 | 12.4 ± 3.45 | >150 | >11.9 | >12.1 |
| 36 | 22.0 ± 4.97 | 24.8 ± 7.00 | >150 | >6.82 | >6.04 |
| 37 | 25.5 ± 10.4 | 13.2 ± 3.45 | >150 | >5.88 | >11.4 |
| 40 | >150 | >150 | >150 | NM | NM |
| 43 | 8.90 ± 1.22 | 12.5 ± 3.36 | >150 | 8.04 | 5.72 |
| 44 | 18.1 ± 0.27 | 17.4 ± 0.30 | >150 | 4.98 | 5.18 |

Example 58

Alkoxyalkyl MPMP esters of cytosine, guanine, 2,6-diaminopurine, 6-methoxypurine and 6-O-methylguanine Also prepared were alkoxyalkyl MPMP esters of cytosine, guanine, 2,6-diaminopurine, 6-methoxypurine and 6-O-methylguanine. The most active anti-HCV compound was ODE- (S)-MPMPG (34) with $EC_{50}$ values of 8.26 and 10.7 µM against genotype 1b and 2a, respectively; the (R) isomer (35) was slightly less active with $EC_{50}$s of 12.6 and 12.4 µM. These compounds also had low cytotoxicity with $CC_{50}$ values>150 µM. HDP-(S)-MPMPMP (43) also exhibited significant activity in the 8.9 to 12.5 µM range. HDP-(S)-MPM-POMG (44) and the ODE and HDP esters of both (R) and (S)-MPMPDAP (23-25) were less active with $EC_{50}$ values ranging from 18 to 26 µM while ODE-(S)-MPMPC (40) was inactive.

Example 59

Evaluation in MT-2 Cells

We also evaluated compounds described herein in MT-2 cells infected with HIV-1. See Table 6 following. ODE-(S)-HPMPA (1) was highly active with an $EC_{50}$ of 0.0001 µM. However, the $CC_{50}$ was 0.033 µM making it the most cytotoxic compound in the series. ODE-(S)-MPMPA (15) retained substantial antiviral activity with an $EC_{50}$ of 0.03 µM and a $CC_{50}$ of 22 µM (selectivity index 733) while HDP-(S)-MPMPA (17) was less active and ODE-(R)-MPMPA (16) was considerably less active and selective. Introduction of an ethoxy or isopropoxy at the 3'-hydroxyl position of the acyclic moiety (compounds 18, 19) resulted in a loss of antiviral activity (Table 6).

same pattern was observed with ODE-(R)-MPMPDAP (24) which was more active ($EC_{50}$=0.4 µM) than the (S) isomer (23). As noted before with the adenine analogs, the HDP esters (25, 36) were less active. Again, introduction of larger ethyl groups at the 3'-hydroxyl of the acyclic chain of these compounds (26, 37) caused a large loss of anti-HIV activity. ODE-(S)-MPMPC (40) was not highly active ($EC_{50}$=12.7 µM) and HDP-(S)-MPMPMP (43) and HDP-(S)-MPMPOMG (44) were not highly active against HIV ($EC_{50}$>10 µM).

Example 61

ODE-(S)-MPMPA Against HCMV and HSV-1

ODE-(S)-MPMPA was also tested against HCMV and HSV-1 using our previous methods. See Prichard, M. N., et al., 2008, *Antimicrob. Agents Chemother.*, 52:4326-4330. We reported previously that ODE-(S)-HPMPA is a powerful inhibitor of the replication of orthopoxviruses, including variola, vaccinia and cowpox, and ectromelia, as well as other dsDNA viruses including human cytomegalovirus (HCMV) and herpes simplex virus, type 1 (HSV-1). See e.g., Beadle, et al., 2006, Id.; Huggins, J. W., 2002, *Antiviral Res.*, 53:A66

TABLE 6

| | Compound | $EC_{50}$ (µM) | $CC_{50}$ (µM) | Selectivity Index |
|---|---|---|---|---|
| 1 | ODE-(S)-HPMPA | 0.0001 ± 0.000 (6) | 0.033 ± 0.02 (3) | 330 |
| 15 | ODE-(S)-MPMPA | 0.03 ± 0.015 (3) | 22 ± 5 (3) | 733 |
| 16 | ODE-(R)-MPMPA | 4.8 ± 3.0 (3) | 26.7 ± 11.2 (3) | 5.6 |
| 17 | HDP-(S)-MPMPA | 0.20 ± 0.26 (4) | 32 ± 11 (3) | 160 |
| 18 | HDP-(R,S)-EPMPA | >10 | 23.6 ± 7.1 (3) | NM |
| 19 | HDP-(R,S)-IPPMPA | >10 | 30.3 ± 12.5 (3) | NM |
| 23 | ODE-(S)-MPMPDAP | 0.23 ± 0.15 | 18.0 ± 5.3 (3) | 78 |
| 24 | ODE-(R)-MPMPDAP | 0.04 ± 0.06 (4) | 19.7 ± 9.5 (3) | 493 |
| 25 | HDP-(S)-MPMPDAP | 4.6 ± 1.8 (3) | 22.7 ± 6.8 (3) | 4.9 |
| 26 | HDP-(R,S)-EPMPDAP | >10 | 30.7 ± 11.7 (3) | NM |
| 34 | ODE-(S)-MPMPG | 0.20 ± 0.22 (4) | 25 ± 13 (3) | 125 |
| 35 | ODE-(R)-MPMPG | <1 × 10$^{-5}$ (3) | 44 ± 5.6 (3) | >4.4 × 10$^6$ |
| 36 | HDP-(S)-MPMPG | 2.03 ± 0.95 (4) | 29.3 ± 3.1 (3) | 14.4 |
| 37 | HDP-(R,S)-EPMPG | >10 | 14.9 ± 6.7 (3) | NM |
| 40 | ODE-(S)-MPMPC | 12.7 ± 4.0 (3) | 60.7 ± 16 (3) | 4.8 |
| 43 | HDP-(S)-MPMPMP | >10 | 22.0 ± 3.5 (3) | NM |
| 44 | HDP-(S)-MPMPOMG | >10 | 34.3 ± 7.6 (3) | NM |

Example 60

ODE-(R)-MPMPG

Surprisingly, the most active compound was ODE-(R)-MPMPG (35), $EC_{50}$<1×10$^{-5}$ µM and a selectivity index of >4.4 million. See Table 6. Interestingly, the (S) isomer (34) was substantially less active with an $EC_{50}$ of 0.2 µM. The (abstract 104); Kern, E. R., et al., 2002, *Antimicrob. Agents Chemother.* 46:991-995; Buller, R. M., et al., 2004, *Virology*, 318:474-481; Magee, W. C. et al., 2008, *Antimicrob. Agents Chemother.* 52:586-597. We examined the effect of blocking the 3'-hydroxyl of HPMPA with 3'-methoxy on the compound's antiviral activity against dsDNA viruses including vaccinia, cowpox, HCMV and HSV-1. See Table 7 following.

TABLE 7

| Comparative Antiviral Activity of ODE-(S)-HPMPA versus ODE-(S)-MPMPA Against dsDNA Viruses in vitro | | | | | |
|---|---|---|---|---|---|
| | | $EC_{50}$ (µM) | | | |
| | Compound | Vaccinia | Cowpox | HCMV | HSV-1 |
| 1 | ODE-(S)-HPMPA | 0.02 ± 0.01[a] | 0.05 ± 0.04[a] | 0.003 ± 0.001[a] | <0.0001 |
| 15 | ODE-(S)-MPMPA | 18.3 ± 2.4 | >20 0 | 1.55 ± 0.4[b] | 45.7 ± 10.1[b] |
| | Fold change | 915 | >400 | 516 | >45 million |

[a]Data and methods from Beadle et al. (Id.)
[b]Data for ODE-(S)-MPMPA vs. HCMV and HSV-1 were obtained by plaque reduction assay in HFF cells as previously described by Prichard et al. (Id.)

As we reported previously, ODE-(S)-HPMPA had potent antiviral activity against these viruses with $EC_{50}$ values ranging from <0.1 to 20 nanomolar. However, ODE-(S)-MPMPA (15) exhibited a dramatic loss of antiviral activity with $EC_{50}$ values >400 to >45 million times higher than those of ODE-(S)-HPMPA (Table 7). We reported previously that inhibition of vaccinia virus replication occurs by a unique mechanism in which (S)-HPMPA diphosphate is incorporated into DNA by the viral E9L polymerase. However, the vaccinia polymerase cannot copy across the drug lesion in HPMPA containing templates. See Magee, et al., 2008, Id. The $EC_{50}$ for vaccinia inhibition by ODE-(S)-HPMPA is 20 nanomolar versus 18,300 nanomolar for ODE-(S)-MPMPA, a reduction of 915-fold. See Table 7. These findings generally support the principal mechanism which we described previously because incorporation of HPMPA into viral DNA, blocking further copying of the drug-containing chain is not possible with ODE-(S)-MPMPA, and any residual antiviral activity with the latter compound is due to obligatory chain termination. Without wishing to be bound by any theory, it is believed that this is presumably also the mechanism of action in cowpox which has a closely related DNA polymerase.

Example 62

Activity in Human Peripheral Blood Mononuclear Cells

Compound ODE-(S)-MPMPA was tested in Human Peripheral Blood Mononuclear Cells (PBMCs) infected with HIV-1$_{NL43}$. The resulting $EC_{50}$ was about 5 nM, and the CC50 was >10 uM, giving a selectivity of >2000. HDP-esters of MPMPA and MPMPG were also active against HIV-1 with $EC_{50}$ values of 0.2 and 2.0 µM. Thus, ODE-(S)-HPMPA was highly active and selective in HIV-1 infected human PBMCs; HDP-(S)-MPMPA and HDP-(S)-MPMPG were also active and selective. See Table 8 following.

TABLE 8

Effect of ODE-(S)-MPMPA and Related Compounds on HIV-1 Replication in Human Peripheral Blood Mononuclear Cells (PBMCs)

| | HIV-1$_{NL43}$ | | |
|---|---|---|---|
| Compound | $EC_{50}$ (µM) | $CC_{50}$ (µM) | Selectivity ($CC_{50}/EC_{50}$) |
| ODE-(S)-MPMPA | 0.005 | >10 | >2000 |
| HDP-(S)-MPMPA | 0.10 | >10 | >100 |
| HDP-(S)-MPMPG | 0.17 | >100 | >590 |

Example 63

Cytotoxicity Studies

Table 9 following provides comparative cytotoxicity data for ODE-(S)-HPMPA and ODE-(S)-MPMPA using previously reported methods. In liver cells (Huh 7.5), fibroblasts (HFF) and lymphoblasts (MT-2), ODE-(S)-MPMPA was remarkably less cytotoxic than the corresponding ODE-(S)-HPMPA compound.

TABLE 9

Reduced Cytotoxicty of ODE-(S)-MPMPA versus ODE-(S)-HPMPA in Various Cell Lines

| | $CC_{50}$ (µM) | | |
|---|---|---|---|
| Cell type | ODE-(S)-HPMPA | ODE-(S)-MPMPA (µM) | fold change |
| Huh 7.5[a] | 35.6 | >150 | >4.2 |
| HFF[b] | 0.58 ± 0.3 | 23.8 ± 2.6 | 41 |
| MT-2[c] | 0.03 ± 0.02 | 22.0 ± 5.0 | 733 |

[a,b,c]Descriptions of cytotoxicity methods: Huh 7.5 cells (Brown, N. A., *Expert Opin. Investig. Drugs* 18: 709-725 (2009)); HFF cells (U.S. Pat. No. 7,044,772); MT-2 cells (U.S. Pat. No. 7,452,898).

As is generally known, ODE-(S)-HPMPA is highly active against double stranded DNA viruses such as vaccinia, cowpox, human cytomegalovirus and herpes simplex virus (1) as summarized in Table 7. Surprisingly, ODE-(S)-MPMPA shows a dramatic loss of antiviral activity against double stranded-DNA viruses representing several orders of magnitude when compared with ODE-(S)-HPMPA.

Example 64

Inhibition of HIV Reverse Transcriptase by (S)-MPMPA Diphosphate

Chemicals.

(S)-MPMPA diphosphate was prepared as described in Example 56. Radiolabeled [γ-$^{32}$P]ATP and cordycepin triphosphate ([α-$^{32}$P]3'-deoxyATP) was purchased from PerkinElmer, and unlabeled deoxynucleoside triphosphates (dNTPs) were from Fermentas. RNA oligonucleotides were purchased from Sigma.

Assays:

Oligonucleotide primer-template pairs were used as substrates for reverse transcriptase assays. Reverse transcriptase assays utilized RNA oligonucleotide templates. The primers were first end-labeled by using [γ-$^{32}$P]ATP and T4 polynucleotide kinase prior to annealing to the template strand. Various combinations of dNTPs and (S)-MPMPApp were added. HIV-1 reverse transcriptase (from the NIH AIDS Research and Reference Reagent Program) was used at a final concentration of 50 nM in a solution containing 50 mM Tris.HCl, pH 7.8; 50 mM NaCl; and 6 mM MgCl$_2$. After incubation of controls and (S)-MPMPA at 37° C. for 5 min, reaction mixtures were stopped by the addition of gel loading buffer [80% (v/v) formamide, 10 mM EDTA (pH 8.0), 1 mg/ml xylene cyanol FF, 1 mg/ml bromophenol blue]. Reaction products were resolved on 10% polyacrylamide gels and analyzed by phosphorimager analysis as previously described (Magee et al., 2005) using a Typhoon 9400 phosphorimager.).

Result:

(S)-MPMPA diphosphate inhibited HIV reverse transcriptase activity by chain termination.

Reference:

Magee, W. C. et al., *Antimicrob. Agents Chemother.* 49: 3153-3162 (2005).

VII. References

References cited herein are incorporated in their entireties and for all purposes. Thus, the following documents are herein incorporated by reference in their entirety and for all purposes:

1. Rosenberg, I. et al., *Coll. Czech. Chem. Comm.* 53:2753-2777 (1988).

2. Tokota, T. et al, *Antiviral Chem. Chemotherap.* 5:57-63 (1999).
3. Kern, E. R. et al., *Antimicrob Agents Chemother.* 46:991-995 (2002).
4. Beadle, J. R. et al., *Antimicrob. Agents Chemother.* 46:2381-2386 (2002).
5. Beadle, J. R. et al., *J. Med. Chem.* 49:2010-2015 (2006).
6. Hostetler, K. Y., Beadle, J. R. and Kini, G. D., U.S. Pat. No. 6,716,825, "Phosphonate Compounds," Apr. 6, 2004.
7. Hostetler, K. Y., Beadle, J. R. and Kini, G. D., U.S. Pat. No. 7,034,014, "Phosphonate Compounds," Apr. 25, 2006.
8. Hostetler, K. Y., Beadle, J. R. and Kini, G. D., U.S. Pat. No. 7,044,772, "Phosphonate Compounds," Aug. 22, 2006.
9. Hostetler, K. Y., Beadle, J. R. and Kini, G. D., U.S. Pat. No. 7,098,197, "Phosphonate Compounds," Aug. 29, 2006.
10. Hostetler, K. Y., Beadle, J. R. and Kini, G. D., U.S. Pat. No. 7,452,898, "Phosphonate Compounds," Nov. 18, 2008.
11. Brown, N. A., *Expert Opin. Investig. Drugs* 18:709-725 (2009)
12. De Clercq, E., *Biochem. Pharmacol.* 73:911-922 (2007)
13. Holý, A., *Antiviral Res.* 71:248-253 (2006)
14. Koh, Y., et al *J. Med. Chem.* 48:2867 (2005)
15. Mackman, Synthesis and antiviral activity of 4'-modified carbocyclic nucleoside phosphonates (CNPs). *Collection Symposium Series* 10:191 (2008)
16. Prichard, M. N. et al., *Antimicrob. Agents Chemother.* 52:4326-4330 (2008)
17. Sheng, X. C. et al., *Bioorg. Med. Chem. Lett.* 19:3453-3457 (2009)
18. Valiaeva, N. et al., *Antiviral Res.* 72:10-19 (2006)
19. Wyles, D. L. et al., *Antimicrob. Agents Chemother.* 53:2660-2662 (2009)
20. Hostetler, K. Y. et al., *Antimicrob. Agents Chemother.,* 50:2857-2859 (2006)
21. Magee, W. C. et al., *Antimicrob. Agents Chemother.* 49:3153-3162 (2005).
22. Hostetler, K. Y., Beadle, J. R. and Kini, G. D., U.S. Pat. No. 7,687,480, "Phosphonate Compounds," Mar. 30, 2010.

What is claimed is:

1. A compound having the structure of Formula (I):

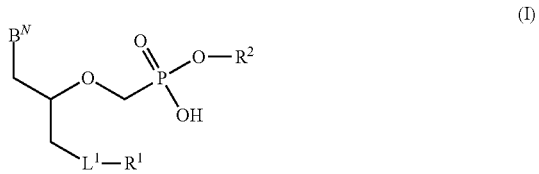

(I)

wherein
$B^N$ is a substituted or unsubstituted nucleobase;
$L^1$ is a bond or —O—;
$R^1$ is halogen, —$CF_3$, unsubstituted alkyl, substituted or unsubstituted cycloalkyl, or substituted or unsubstituted aryl;
provided that, if $L^1$ is a bond, then $R^1$ is halogen, and if $L^1$ is —O—, then $R^1$ is —$CF_3$, unsubstituted alkyl, substituted or unsubstituted cycloalkyl, or substituted or unsubstituted aryl;
$R^2$ is $L^2$-O-$R^3$ (II), wherein $L^2$ is a substituted or unsubstituted alkylene, substituted or unsubstituted cycloalkylene, or substituted or unsubstituted arylene; and
$R^3$ is substituted or unsubstituted alkyl, substituted or unsubstituted cycloalkyl, or substituted or unsubstituted aryl;
or pharmaceutically accepted salt or solvate thereof.

2. The compound of claim 1, wherein $B^N$ is unsubstituted adenine, substituted adenine, unsubstituted thymine, substituted thymine, unsubstituted guanine, substituted guanine, unsubstituted cytosine, substituted cytosine, unsubstituted uracil, substituted uracil, 2,6-diaminopurine, 6-methoxypurine, or 6-O-methylguanine.

3. The compound of claim 1, with structure of Formula (Ia):

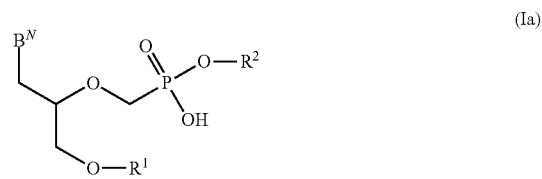

(Ia)

wherein
$R^1$ is —$CF_3$, unsubstituted alkyl, substituted or unsubstituted cycloalkyl, or substituted or unsubstituted aryl.

4. The compound of claim 1, wherein $R^1$ is unsubstituted alkyl, unsubstituted cycloalkyl, or unsubstituted aryl.

5. The compound of claim 1, wherein $R^1$ is unsubstituted $C_1$-$C_{10}$ alkyl.

6. The compound of claim 5, wherein $R^1$ is methyl, ethyl or isopropyl.

7. The compound of claim 1, wherein $R^1$ is unsubstituted cycloalkyl.

8. The compound of claim 1, wherein $R^1$ is unsubstituted aryl.

9. The compound of claim 8, wherein $R^1$ is phenyl.

10. The compound of claim 1, wherein $R^1$ is unsubstituted alkyl, substituted cycloalkyl, or substituted aryl.

11. The compound of claim 1, with structure of Formula (Ib):

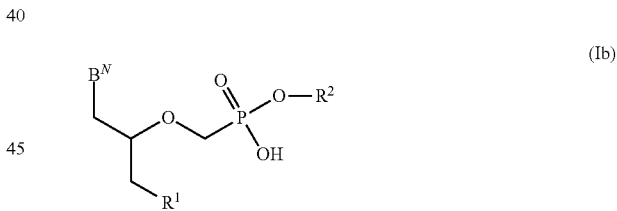

(Ib)

wherein $L^1$ is a bond, and $R^1$ is halogen.

12. The compound of claim 11, wherein $R^1$ is fluoro.

13. The compound of claim 1, with the structure of Formulae (Ia1) to (Ia7):

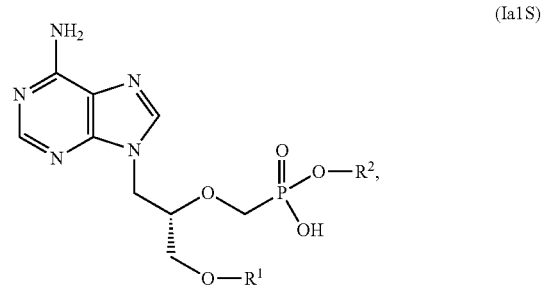

(Ia1S)

-continued
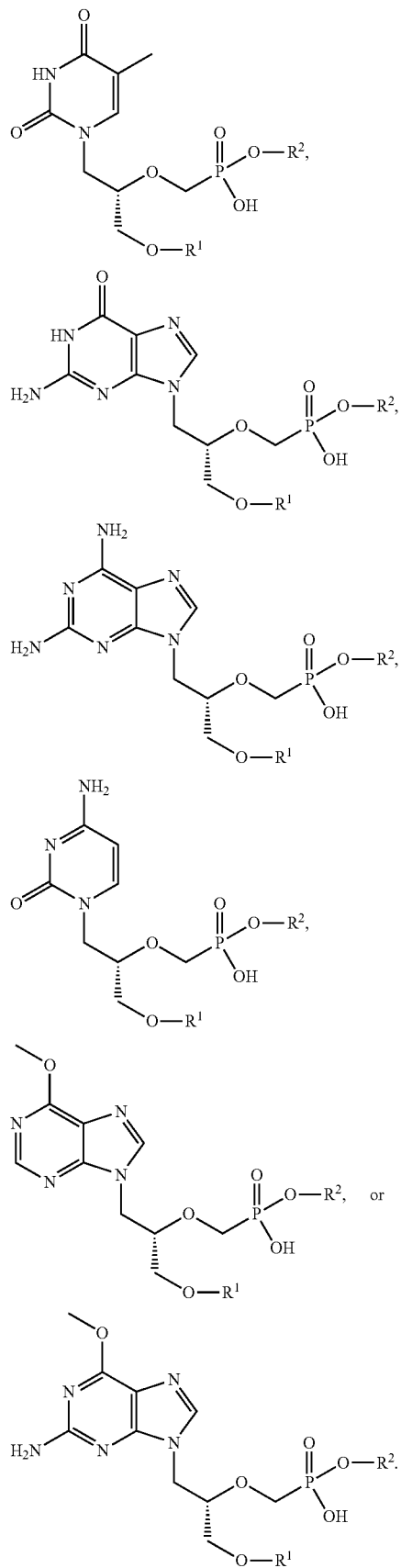
14. The compound of claim 1, wherein $R^2$ is octadecyloxyethyl, hexadecyloxyethyl, hexadecyloxypropyl, 15-methyl-hexadecyloxypropyl, 15-methyl-hexadecyloxyethyl, 14-methyl-tetradecyloxypropyl, 14-methyl-tetradecyloxyethyl, 14-cyclopropyl-tetradecyloxypropyl, 14-cyclopropyl-tetradecyloxyethyl, or 1-O-octadecyl-2-O-benzyl-sn-glyceryl.
15. A compound with structure:
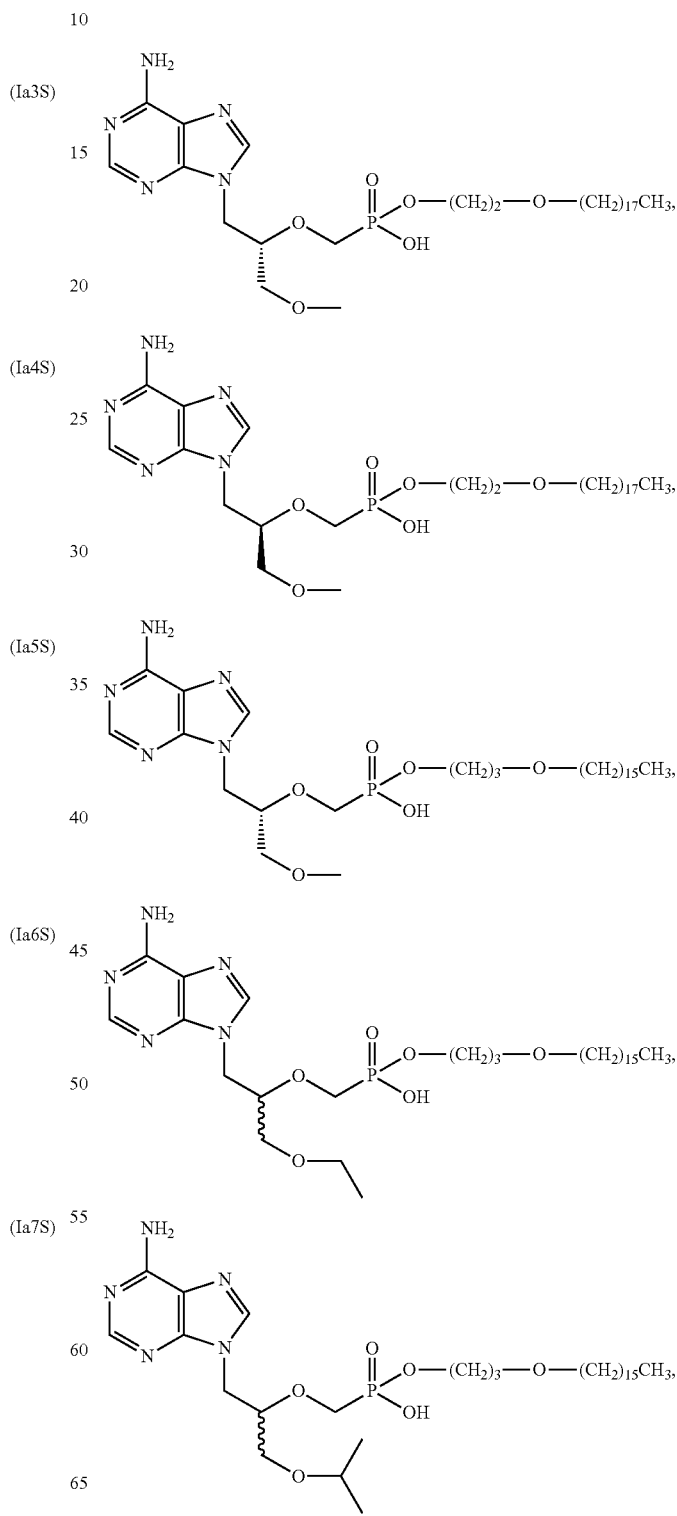

79
-continued
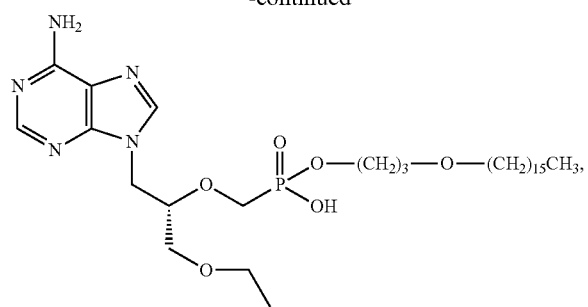
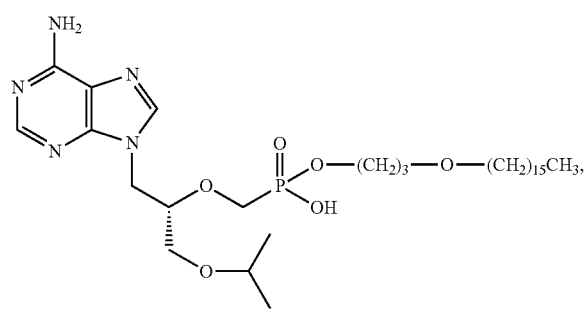
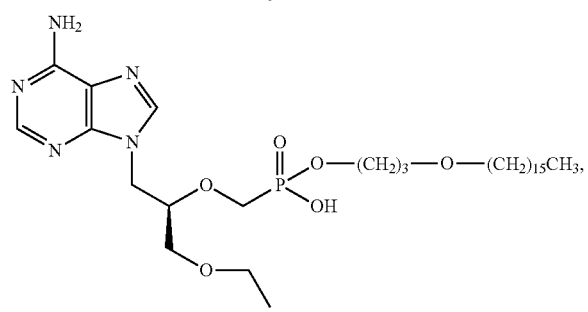
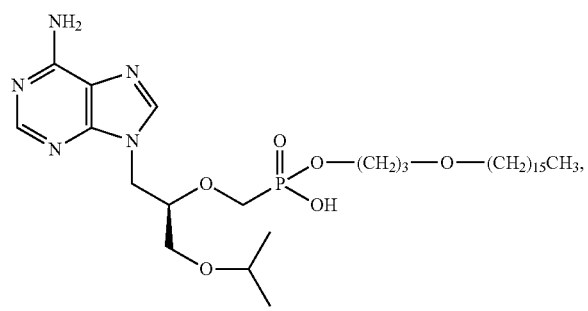
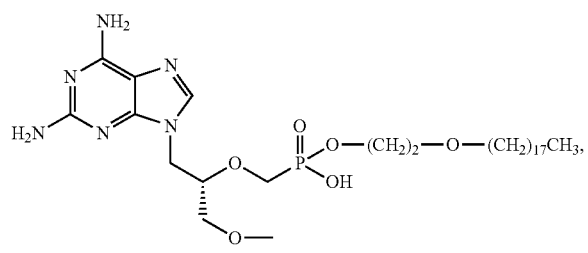
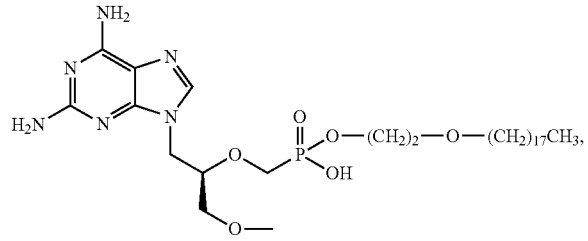
80
-continued
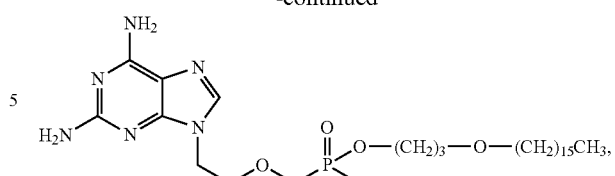
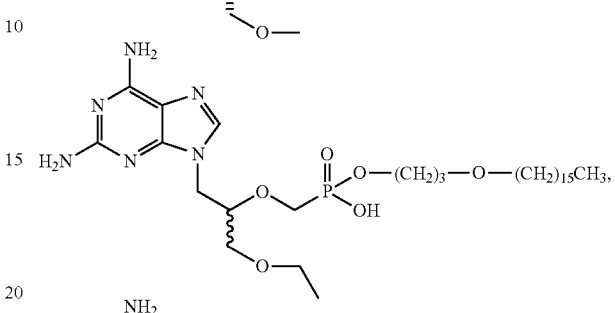
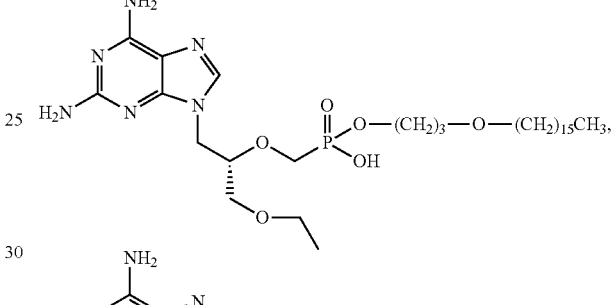
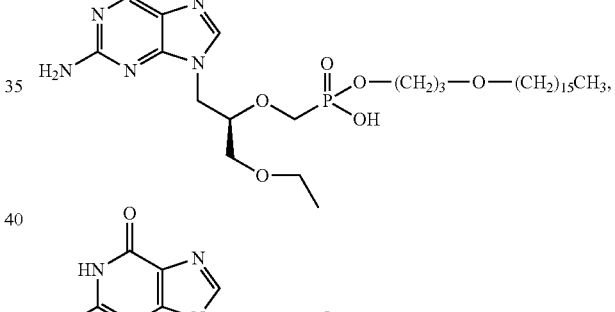
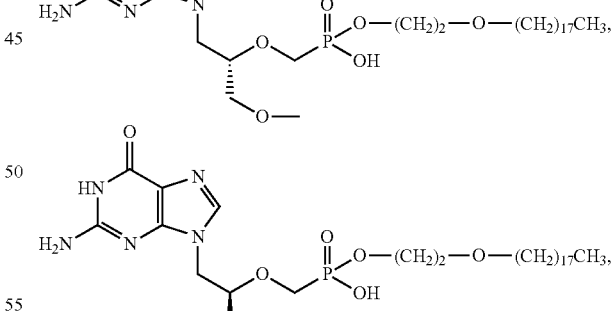
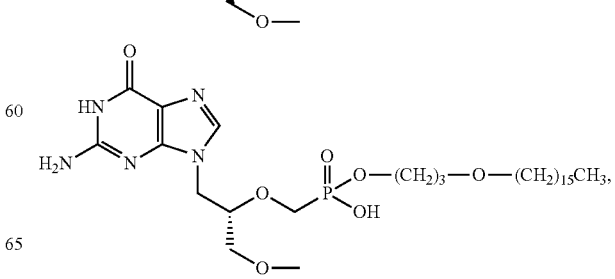

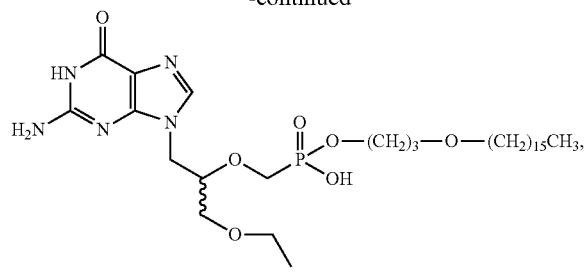

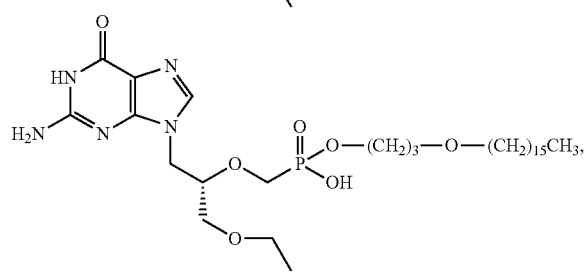

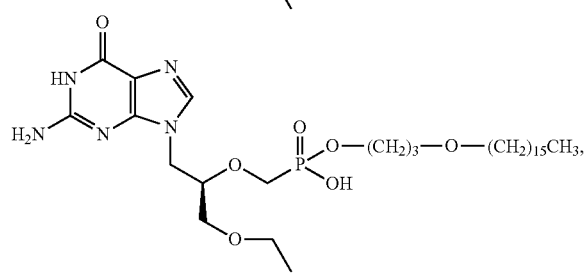

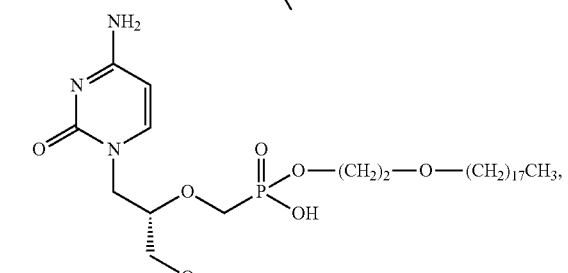

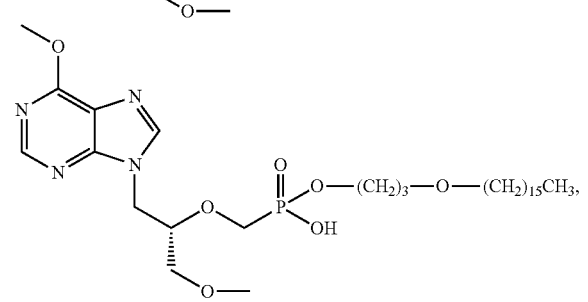

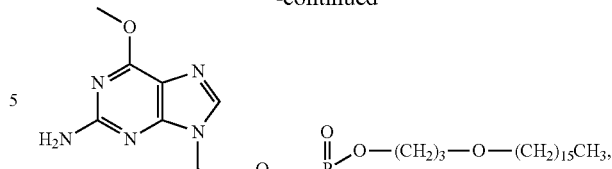

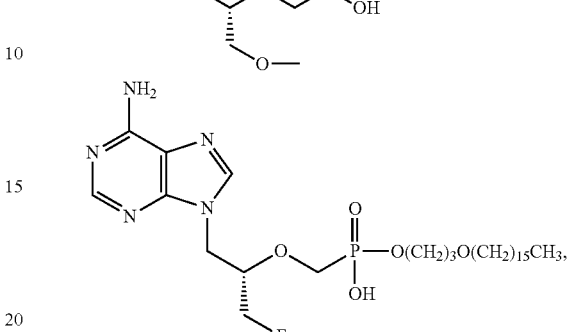

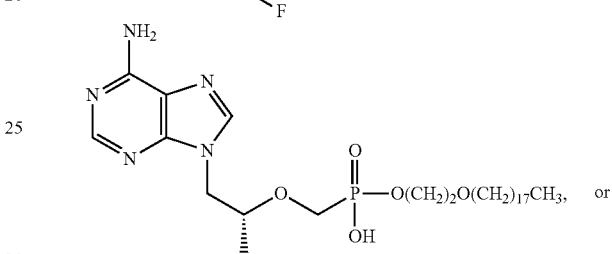

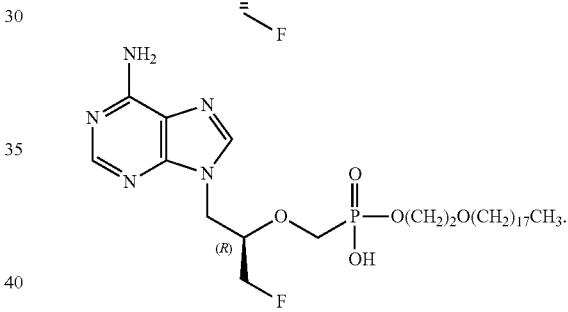

16. A pharmaceutical composition comprising a compound of claim 1 and a pharmaceutically acceptable excipient.

17. A method of inhibiting a viral reverse transcriptase comprising contacting a cell comprising a viral reverse transcriptase with an effective amount of a compound of claim 1, thereby inhibiting said viral reverse transcriptase, wherein said viral reverse transcriptase is an HIV reverse transcriptase.

* * * * *